United States Patent
Scheidt et al.

(10) Patent No.: US 12,410,149 B2
(45) Date of Patent: Sep. 9, 2025

(54) SUBSTITUTED CHROMANES, ANALOGS THEREOF, AND METHODS OF USE AND SYNTHESIS

(71) Applicant: Northwestern University, Evanston, IL (US)

(72) Inventors: Karl A. Scheidt, Evanston, IL (US); Rick C. Betori, Gurnee, IL (US); Benjamin R. McDonald, Somerville, MA (US)

(73) Assignee: Northwestern University, Evanston, IL (US)

( * ) Notice: Subject to any disclaimer, the term of this patent is extended or adjusted under 35 U.S.C. 154(b) by 128 days.

(21) Appl. No.: 18/187,380

(22) Filed: Mar. 21, 2023

(65) Prior Publication Data

US 2023/0339879 A1 Oct. 26, 2023

Related U.S. Application Data

(62) Division of application No. 16/923,843, filed on Jul. 8, 2020, now Pat. No. 11,639,340.

(60) Provisional application No. 62/871,673, filed on Jul. 8, 2019.

(51) Int. Cl.
| | | |
|---|---|---|
| C07D 311/58 | (2006.01) | |
| C07C 67/303 | (2006.01) | |
| C07D 215/14 | (2006.01) | |
| C07D 215/58 | (2006.01) | |
| C07D 307/80 | (2006.01) | |
| C07D 311/64 | (2006.01) | |
| C07D 311/92 | (2006.01) | |

(52) U.S. Cl.
CPC .......... *C07D 311/58* (2013.01); *C07C 67/303* (2013.01); *C07D 215/14* (2013.01); *C07D 215/58* (2013.01); *C07D 307/80* (2013.01); *C07D 311/64* (2013.01); *C07D 311/92* (2013.01)

(58) Field of Classification Search
CPC ... C07C 311/38; C07C 215/58; C07C 307/80; C07C 311/64; C07C 311/92; C07C 311/58
See application file for complete search history.

(56) References Cited

U.S. PATENT DOCUMENTS

| | | | |
|---|---|---|---|
| 7,851,640 B2 | 12/2010 | Scheidt | |
| 8,481,760 B2 | 7/2013 | Bergan | |
| 8,742,141 B2 | 6/2014 | Bergan | |
| 8,912,341 B2 | 12/2014 | Scheidt | |
| 9,090,634 B2 | 7/2015 | Scheidt | |
| 9,260,564 B2 | 2/2016 | Lombardo | |
| 9,309,217 B2 | 4/2016 | Scheidt | |
| 9,334,297 B2 | 5/2016 | Scheidt | |
| 9,512,146 B2 | 12/2016 | Scheidt | |
| 9,527,812 B2 | 12/2016 | Scheidt | |
| 9,624,190 B2 | 4/2017 | Scheidt | |
| 9,643,947 B2 | 5/2017 | Scheidt | |
| 9,839,625 B2 | 12/2017 | Bergan | |
| 9,840,487 B2 | 12/2017 | Scheidt | |
| 9,981,968 B2 | 5/2018 | Schiltz | |
| 10,231,949 B2 | 3/2019 | Bergan | |
| 10,308,624 B2 | 6/2019 | Scheidt | |
| 10,323,039 B2 | 6/2019 | Scheidt | |
| 10,654,865 B2 | 5/2020 | Scheidt | |
| 10,780,076 B2 | 9/2020 | Bergan | |
| 10,781,172 B2 | 9/2020 | Scheidt | |
| 2009/0124569 A1 | 5/2009 | Bergan | |
| 2010/0137425 A1 | 6/2010 | Bergan | |
| 2012/0283313 A1 | 11/2012 | Bergan | |
| 2013/0296582 A1 | 11/2013 | Bergan | |
| 2014/0206886 A1 | 7/2014 | Scheidt | |
| 2015/0065703 A1 | 3/2015 | Scheidt | |
| 2015/0247004 A1 | 9/2015 | Lombardo | |
| 2015/0315143 A1 | 11/2015 | Scheidt | |
| 2015/0315168 A1 | 11/2015 | Scheidt | |
| 2016/0002252 A1 | 1/2016 | Schiltz | |
| 2016/0024120 A1 | 1/2016 | Scheidt | |
| 2016/0075728 A1 | 3/2016 | Schedit | |
| 2016/0128973 A1 | 5/2016 | Bergan | |
| 2016/0326183 A1 | 11/2016 | Scheidt | |
| 2018/0153853 A1 | 6/2018 | Bergan | |
| 2019/0201373 A1 | 7/2019 | Bergan | |
| 2019/0276458 A1 | 9/2019 | Schiltz | |
| 2019/0300540 A1 | 10/2019 | Scheidt | |
| 2019/0389798 A1 | 12/2019 | Scheidt | |
| 2020/0181106 A1 | 6/2020 | Scheidt | |
| 2020/0399241 A1 | 12/2020 | Scheidt | |
| 2021/0002221 A1 | 1/2021 | Scheidt | |
| 2021/0009547 A1 | 1/2021 | Scheidt | |
| 2021/0009603 A1 | 1/2021 | Scheidt | |

(Continued)

OTHER PUBLICATIONS

Akalay, D., et al. "Synthesis of C 2-Symmetric Bisamidines: A New Type of Chiral Metal-Free Lewis Acid Analogue Interacting with Carbonyl Groups." The Journal of organic chemistry 72.15 (2007): 5618-5624.

Akhtar, T., et al. "In vitro antitumor and antiviral activities of new benzothiazole and 1, 3, 4-oxadiazole-2-thione derivatives." Acta pharmaceutica 58.2 (2008): 135-149.

Arias-Rotondo, D. M., et al. "The photophysics of photoredox catalysis: a roadmap for catalyst design." Chemical Society Reviews 45.21 (2016): 5803-5820.

Betori, R. C., et al. "Reductive annulations of arylidene malonates with unsaturated electrophiles using photoredox/Lewis acid cooperative catalysis." Chemical science 10.11 (2019): 3353-3359.

(Continued)

*Primary Examiner* — Jared Barsky
(74) *Attorney, Agent, or Firm* — Quarles & Brady LLP

(57) ABSTRACT

Disclosed are chromane compounds, analogs thereof, and methods of their synthesis and use. The compounds may be synthesized by methods involving reductive annulations of arylidene malonates with unsaturated electrophiles using photoredox/Lewis acid cooperative catalysis. The compounds may be formulated in a pharmaceutical composition for treating one of the aforementioned diseases or disorders.

17 Claims, 12 Drawing Sheets

(56) References Cited

U.S. PATENT DOCUMENTS

| | | |
|---|---|---|
| 2021/0024473 A1 | 1/2021 | Scheidt |
| 2021/0070725 A1 | 3/2021 | Scheidt |
| 2021/0214352 A1 | 7/2021 | Scheidt |

OTHER PUBLICATIONS

Biddle, M. M., et al. "Catalytic enantioselective synthesis of flavanones and chromanones." Journal of the American Chemical Society 129.13 (2007): 3830-3831.

Bonilla, P., et al. "Photo-Organocatalytic Enantioselective Radical Cascade Reactions of Unactivated Olefins." Angewandte Chemie International Edition 57.39 (2018): 12819-12823.

Chen, M., et al. "Visible-light-triggered directly reductive arylation of carbonyl/iminyl derivatives through photocatalytic PCET." Organic letters 19.14 (2017): 3807-3810.

Choi, S.-J., et al. "Solid phase combinatorial synthesis of benzothiazoles and evaluation of topoisomerase II inhibitory activity." Bioorganic & medicinal chemistry 14.4 (2006): 1229-1235.

Cismesia, M. A., et al. "Characterizing chain processes in visible light photoredox catalysis." Chemical science 6.10 (2015): 5426-5434.

De Assis, F. F., et al. "Visible-Light-Activated Catalytic Enantioselective ß-Alkylation of a, ß-Unsaturated 2-Acyl Imidazoles Using Hantzsch Esters as Radical Reservoirs." The Journal of organic chemistry 83.18 (2018): 10922-10932.

Dell'Amico, L., et al. "Light-Driven Enantioselective Organocatalytic ß-Benzylation of Enals." Angewandte Chemie International Edition 56.12 (2017): 3304-3308.

Du, J., et al. "Crossed intermolecular [2+2] cycloadditions of acyclic enones via visible light photocatalysis." Journal of the American Chemical Society 131.41 (2009): 14604-14605.

Du, J., et al. "Photocatalytic reductive cyclizations of enones: Divergent reactivity of photogenerated radical and radical anion intermediates." Chemical science 2.11 (2011): 2115-2119.

Farmer, R. L., et al. "Concise syntheses of the abyssinones and discovery of new inhibitors of prostate cancer and MMP-2 expression." ACS medicinal chemistry letters 1.8 (2010): 400-405.

Fava, E., et al. "Photoredox-catalyzed Ketyl-Olefin coupling for the synthesis of substituted chromanols." The Journal of organic chemistry 81.16 (2016): 6959-6964.

Fava, E., et al. "Reductive Umpolung of Carbonyl Derivatives with Visible-Light Photoredox Catalysis: Direct Access to Vicinal Diamines and Amino Alcohols via a-Amino Radicals and Ketyl Radicals." Angewandte Chemie International Edition 55.23 (2016): 6776-6779.

Foy, N. J., et al. "Dual Lewis Acid/Photoredox-Catalyzed Addition of Ketyl Radicals to Vinylogous Carbonates in the Synthesis of 2, 6-Dioxabicyclo [3.3.0] octan-3-ones." Organic letters 20.18 (2018): 5727-5731.

Fuentes De Arriba, A. L., et al. "Umpolung synthesis of branched a-functionalized amines from imines via photocatalytic three-component reductive coupling reactions." Chemical Communications 52.100 (2016)., 14434.

Gentry, E. C., et al. "Synthetic applications of proton-coupled electron transfer." Accounts of chemical research 49.8 (2016): 1546-1556.

Goti, G., et al. "Stereocontrolled Synthesis of 1, 4-Dicarbonyl Compounds by Photochemical Organocatalytic Acyl Radical Addition to Enals." Angewandte Chemie International Edition 58.4 (2019): 1213-1217.

Hopkinson, M. N., et al. "Dual Catalysis Sees the Light: Combining Photoredox with Organo-, Acid, and Transition-Metal Catalysis." Chemistry—A European Journal 20.14 (2014): 3874-3886.

Hurtley, A. E., et al. "Visible light photocatalysis of radical anion hetero-Diels-Alder cycloadditions." Tetrahedron 67.24 (2011): 4442-4448.

Ischay, M. A., et al. "[2+2] cycloadditions by oxidative visible light photocatalysis." Journal of the American Chemical Society 132.25 (2010): 8572-8574.

Ischay, M. A., et al. "Efficient visible light photocatalysis of [2+2] enone cycloadditions." Journal of the American Chemical Society 130.39 (2008): 12886-12887.

Jeffrey, J. L., et al. "Selective radical-radical cross-couplings: design of a formal ß-mannich reaction." Journal of the American Chemical Society 137.26 (2015): 8404-8407.

Jin, L., et al. "Synthesis, X-ray crystallographic analysis, and antitumor activity of N-(benzothiazole-2-yl)-1-(fluorophenyl)-O, O-dialkyl-a-aminophosphonates." Bioorganic & medicinal chemistry letters 16.6 (2006): 1537-1543.

Kwak, J.-H., et al. "Structure-activity relationships of 6-hydroxy-7-methoxychroman-2-carboxylic acid N-(substituted) phenylamides as inhibitors of nuclear factor-kB activation." Archives of pharmacal research 30.10 (2007): 1210-1215.

Lampronti, I., et al. "In vitro antiproliferative effects on human tumor cell lines of extracts from the Bangladeshi medicinal plant Aegle marmelos Correa." Phytomedicine 10.4 (2003): 300-308.

Lang, F., et al. "A stereoselective aldol reaction via diisopinocampheyl boron-enolate in preparation of chromane carboxylate with quaternary carbon." Tetrahedron letters 44.28 (2003): 5285-5288.

Larraufie, M.-H., et al. "Visible-light-induced photoreductive generation of radicals from epoxides and aziridines." Angewandte Chemie International Edition 50.19 (2011): 4463.

Lee, K. N., et al. "ß-Selective reductive coupling of alkenylpyridines with aldehydes and imines via synergistic Lewis acid/photoredox catalysis." Journal of the American Chemical Society 139.14 (2017): 5003-5006.

Leitch, J. A., et al. "Photocatalytic reverse polarity Povarov reaction." Chemical science 9.32 (2018): 6653-6658.

Lin, K., et al. "Haloselective Cross-Coupling via Ni/Photoredox Dual Catalysis." ACS catalysis 7.8 (2017): 5129-5133.

Lin, S.-X., et al. "A visible-light-activated rhodium complex in enantioselective conjugate addition of a-amino radicals with Michael acceptors." Chemical Communications 53.54 (2017): 7665-7668.

Lu, Z., et al. "[3+2] Cycloadditions of aryl cyclopropyl ketones by visible light photocatalysis." Journal of the American Chemical Society 133.5 (2011): 1162-1164.

Luo, J. et al. "Donor-acceptor fluorophores for visible-light-promoted organic synthesis: Photoredox/Ni dual catalytic C (sp3)-C (sp2) cross-coupling." ACS Catalysis 6.2 (2016): 873-877.

Ma, T., et al. "Chemical library and structure-activity relationships of 11-demethyl-12-oxo calanolide A analogues as anti-HIV-1 agents." Journal of medicinal chemistry 51.5 (2008): 1432-1446.

Mazzarella, D. et al. "Asymmetric Photocatalytic C—H Functionalization of Toluene and Derivatives." Journal of the American Chemical Society 140.27 (2018): 8439-8443.

Mcdonald, B. R., et al. "A biomimetic strategy to access the Silybins: total synthesis of (-)-Isosilybin A." Organic letters 17.1 (2015): 98-101.

McDonald, B. R., et al. "Intermolecular reductive couplings of arylidene malonates via Lewis acid/photoredox cooperative catalysis." Organic letters 20.21 (2018): 6877-6881.

Miller, D. C., et al. "Proton-Coupled Electron Transfer in Organic Synthesis: Fundamentals, Applications, and Opportunities." Hydrogen Transfer Reactions: Reductions and Beyond 374 (2016): 30.

Miyake, Y., et al. "Visible-light-mediated utilization of a-aminoalkyl radicals: addition to electron-deficient alkenes using photoredox catalysts." Journal of the American Chemical Society 134.7 (2012): 3338-3341.

Mizuta, S., et al. "Trifluoromethylation of allylsilanes under photoredox catalysis." Organic letters 15.6 (2013): 1250-1253.

Mortimer, C. G., et al. "Antitumor benzothiazoles. 26. 2-(3, 4-Dimethoxyphenyl)-5-fluorobenzothiazole (GW 610, NSC 721648), a simple fluorinated 2-arylbenzothiazole, shows potent and selective inhibitory activity against lung, colon, and breast cancer cell lines." Journal of medicinal chemistry 49.1 (2006): 179-185.

Murphy, J. J., et al. "Asymmetric catalytic formation of quaternary carbons by iminium ion trapping of radicals." Nature 532.7598 (2016): 218-222.

(56) References Cited

OTHER PUBLICATIONS

Nakajima, M., et al. "Photoredox-Catalyzed Reductive Coupling of Aldehydes, Ketones, and Imines with Visible Light." Angewandte Chemie International Edition 54.30 (2015): 8828-8832.
Neumann, M. et al. "A cooperative hydrogen-bond-promoted organophotoredox catalysis strategy for highly diastereoselective, reductive enone cyclization." Chemistry—A European Journal 19.22 (2013): 6950-6955.
Nibbs, A. E., et al. "Asymmetric methods for the synthesis of flavanones, chromanones, and azaflavanones." European journal of organic chemistry 2012.3 (2012): 449.
Nibbs, A. E., et al. "Catalytic asymmetric alkylation of substituted isoflavanones." Organic letters 11.17 (2009): 4010-4013.
Nicolaou, K. C., et al. "Natural product-like combinatorial libraries based on privileged structures. 1. General principles and solid-phase synthesis of benzopyrans." Journal of the American Chemical Society 122.41 (2000): 9939-9953.
O'Brien, S. E., et al. "Antitumor benzothiazoles. Frontier molecular orbital analysis predicts bioactivation of 2-(4-aminophenyl) benzothiazoles to reactive intermediates by cytochrome P4501A1." Organic & biomolecular chemistry 1.3 (2003): 493-497.
Oh, S. H., et al. "Vicinal difunctionalization of alkenes: chlorotrifluoromethylation with Cf3SO2Cl by photoredox catalysis." Organic letters 16.5 (2014): 1310-1313.
Pecchio, M., et al. "Cytotoxic and antimicrobial benzophenones from the leaves of Tovomita longifolia." Journal of natural products 69.3 (2006): 410-413.
Petronijevic, F. R., et al. "Direct ß-functionalization of cyclic ketones with aryl ketones via the merger of photoredox and organocatalysis." Journal of the American Chemical Society 135.49 (2013): 18323-18326.
Pitre, S. P., et al. "Understanding the kinetics and spectroscopy of photoredox catalysis and transition-metal-free alternatives." Accounts of chemical research 49.6 (2016): 1320-1330.
Prado, S., et al. "Synthesis and antimycobacterial evaluation of benzofurobenzopyran analogues." Bioorganic & medicinal chemistry 15.5 (2007): 2177-2186.
Prier, C. K., et al. "Visible light photoredox catalysis with transition metal complexes: applications in organic synthesis." Chemical reviews 113.7 (2013): 5322-5363.
Qi, L., et al. "Polarity-Reversed Allylations of Aldehydes, Ketones, and Imines Enabled by Hantzsch Ester in Photoredox Catalysis." Angewandte Chemie (International ed. in English) 55.42 (2016): 13312-13315.
Romero, N. A., et al. "Organic photoredox catalysis." Chemical reviews 116.17 (2016): 10075-10166.
Sahoo, B., et al. "Combining gold and photoredox catalysis: visible light-mediated oxy-and aminoarylation of alkenes." Journal of the American Chemical Society 135.15 (2013): 5505-5508.
Shaw, M. H., et al. "Photoredox catalysis in organic chemistry." The Journal of organic chemistry 81.16 (2016): 6898-6926.
Sheldrick, G. M. "A short history of SHELX." Acta Crystallographica Section A: Foundations of Crystallography 64.1 (2008): 112-122.
Silvi, M., et al. "Visible-light excitation of iminium ions enables the enantioselective catalytic ß-alkylation of enals." Nature chemistry 9.9 (2017): 868-873.
Skubi, K. L., et al. "Dual catalysis strategies in photochemical synthesis." Chemical reviews 116.17 (2016): 10035-10074.
Spek, A. L. "Structure validation in chemical crystallography." Acta Crystallographica Section D: Biological Crystallography 65.2 (2009): 148-155.
Streuff, J., et al. "Metal-Catalyzed ß-Functionalization of Michael Acceptors through Reductive Radical Addition Reactions." Angewandte Chemie International Edition 54.48 (2015): 14232-14242.
Studer, A., et al. "Catalysis of radical reactions: a radical chemistry perspective." Angewandte Chemie International Edition 55.1 (2016): 58-102.
Studer, A., et al. "The electron is a catalyst." Nature chemistry 6.9 (2014): 765.
Svetlik, J., et al. "A complicated path of salicylaldehyde through the Biginelli reaction: a case of unexpected spiroketalization." Tetrahedron 70.44 (2014): 8354-8360.
Tanaka, N., et al. "Prenylated Benzophenones and Xanthones from Hypericum s cabrum." Journal of natural products 67.11 (2004): 1870-1875.
Tarantino, K. T., et al. "Catalytic ketyl-olefin cyclizations enabled by proton-coupled electron transfer." Journal of the American Chemical Society 135.27 (2013): 10022-10025.
Terrett, J. A., et al. "Direct ß-alkylation of aldehydes via photoredox organocatalysis." Journal of the American Chemical Society 136.19 (2014): 6858-6861.
Tyson, E. L., et al. "Photocatalytic [2+ 2] cycloadditions of enones with cleavable redox auxiliaries." Organic letters 14.4 (2012): 1110-1113.
Verrier, C., et al. "Direct stereoselective installation of alkyl fragments at the ß-carbon of enals via excited iminium ion catalysis." ACS Catalysis 8.2 (2018): 1062-1066.
Vrabel, V., et al. "Biological activity, structural characterization and crystal packing of chromane-carboxylate derivatives." Acta Chimica Slovaca 11.1 (2018): 1-5.
Wallentin, C.-J., et al. "Visible light-mediated atom transfer radical addition via oxidative and reductive quenching of photocatalysts." Journal of the American Chemical Society 134.21 (2012): 8875-8884.
Wang, R., et al. "Visible-light-mediated umpolung reactivity of imines: ketimine reductions with Cy2NMe and water." Organic letters 20.8 (2018): 2433-2436.
Xu, L., et al. "Precision therapeutic targeting of human cancer cell motility." Nature communications 9.1 (2018): 2454.
Xu. W., et al. "Synergistic Catalysis for the Umpolung Trifluoromethylthiolation of Tertiary Ethers." Angewandte Chemie International Edition 57.32 (2018): 10357-10361.
Yayla, H. G., et al. "Proton-Coupled Electron Transfer in Organic Synthesis: Novel Hornolytic Bond Activations and Catalytic Asymmetric Reactions with Free Radicals." Synlett 25.20 (2014): 2819-2826.
Yoon, T. P. "Photochemical stereocontrol using tandem photoredox-chiral Lewis acid catalysis." Accounts of chemical research 49.10 (2016): 2307-2315.
Yoon, T. P. "Visible light photocatalysis: The development of photocatalytic radical ion cycloadditions." ACS catalysis 3.5 (2013): 895-902.
Zhang, H.-H., et al. "Radical alkylation of imines with 4-alkyl-1, 4-dihydropyridines enabled by photoredox/Brønsted acid cocatalysis." The Journal of organic chemistry 82.19 (2017): 9995-10006.
Zhao, G., et al. "Reactivity Insight into Reductive Coupling and Aldol Cyclization of Chalcones by Visible Light Photocatalysis." The Journal of organic chemistry 77.14 (2012): 6302-6306.
Zou, Y.-S., et al. "Isoprenylated xanthones and flavonoids from Cudrania tricuspidata." Chemistry & biodiversity 2.1 (2005): 131-138.
CAS RN 163434-37-5 (entered STN Jun. 1, 1995). (Year: 1995).
STN Registry No. 183145-96-2 (entered Nov. 16, 1984). (Year: 1984).
Groves et al. in Journal of the Chemical Society (1951) 867-870 (Year: 1951).

FIG. 2

| Entry: | Conditions: | GC Yield: |
|---|---|---|
| 1 | 10% Sc(OTf)$_3$, 0.5% DPAIPN, 0.2 M | 62 |
| 2 | 5% Sc(OTf)$_3$, 0.5% DPAIPN, 0.2 M | 51 |
| 3 | 5% Sc(OTf)$_3$, 1% DPAIPN, 0.2 M | 65 |
| 4 | 10% Sc(OTf)$_3$, 1% DPAIPN, 0.2 M | 81 |
| 5 | 10% Sc(OTf)$_3$, 0.5% DPAIPN, 0.1 M | 65 |
| 6 | 5% Sc(OTf)$_3$, 0.5% DPAIPN, 0.1 M | 55 |
| 7 | 10% Sc(OTf)$_3$, 0.5% DPAIPN, 0.05 M | 42 |
| 8 | 5% Sc(OTf)$_3$, 1% DPAIPN, 0.05 M | 41 |

[a] Yield determined by GC with bibenzyl as internal standard.

SUBSTITUTED CHROMANES, ANALOGS THEREOF, AND METHODS OF USE AND SYNTHESIS

CROSS-REFERENCE TO RELATED APPLICATIONS

This application is a divisional of U.S. patent application Ser. No. 16/923,843, filed on Jul. 8, 2020, which claims the benefit of priority to U.S. Provisional Application Ser. No. 62/871,673 filed on Jul. 8, 2019, the entire contents of each are incorporated by reference herein.

STATEMENT REGARDING FEDERALLY SPONSORED RESEARCH OR DEVELOPMENT

This invention was made with government support under GM073072 and GM116532 awarded by the National Institutes of Health. The government has certain rights in the invention.

FIELD

The field of the invention relates to chromane compounds, analogs thereof, and their methods of use and synthesis. In particular, the field of the invention relates to substituted chromane compounds and analogs thereof that exhibit a broad range of bioactivities, such as antiviral activities, antitumor activities, antimicrobial activities, sex pheromone activity, and activities that modulate the central nervous system.

BACKGROUND

Chromanes or dihydrobenzopyranes are found in numerous biologically active natural products. (See Vribel et al., 2018). Molecules containing a chromane skeleton are known to exhibit a broad range of bioactivities, such as antiviral activities, antitumor activities, antimicrobial activities, sex pheromone activities, and activities that modulate the activity of the central nervous system. (See, e.g., Vrabel et al. 2018 citing to Ellis & Lockhart, 2007; and Horton et al., 2003). Chromane molecules have an extra dihydropyrano ring in comparison to other naturally occurring prenylated molecules and possess most interesting properties. (See, e.g., Nicolaou et al., 2000).

Chromanes are generally characterized by low cellular toxicity and good membrane permeability, which make chromanes good drug template compounds. Some chromanes have been shown to inhibit mycobacterial growth. (See Prado et al., 2007). Other chromanes are promising therapeutic agents for AIDS. (See Ma et al., 2008). Some chromanes possess antitumoral activity. (See Tanaka et al., 2004; Zou et al., 2005). Chromane derivatives have been shown to be therapeutic agents in the treatment of cancer and cell proliferative disorders. (See Kwak et al., 2010; and Pecchio et al., 2006). Chromane carboxylates, especially those with quaternary carbons, have been utilized as leukotriene D4 (LTD4) inhibitors for the treatment of allergic reactions and inflammatory conditions; as peroxisome proliferator activated receptor (PPAR) agonists for treatment of type 2 diabetes and for their antioxidants/antiarrythmic activity. (See Lang et al., 2003).

Therefore, new methods of synthesizing chromanes and derivatives thereof are desirable. Here, the inventors disclose new chromane compounds synthesized by reductive annulatons of arylidene malonates with unsaturated electrophiles using photoredox/Lewis acid cooperative catalysis.

SUMMARY

Disclosed are chromane compounds, analogs thereof, and methods of their synthesis and use. The chromane compounds may be synthesized by methods involving reductive annulations of arylidene malonates with unsaturated electrophiles using photoredox/Lewis acid cooperative catalysis. The disclosed chromane compounds and analogs thereof may be used in pharmaceutical compositions and methods for treating diseases and disorders in a patient, such as viral infections, bacterial infections, fungal infections, tumor growth, allergic reactions, inflammatory conditions, cancer and cell proliferative disorders.

In some embodiments, the disclosed compounds may have a formula as follows, or a salt or hydrate thereof:

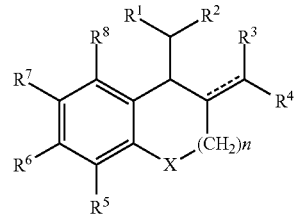

The compounds are optionally substituted. In some embodiments, $R^1$ and $R^2$ are independently selected from hydrogen, alkyl, alkoxy, carboxy, and carboxyalkyl. In some embodiments, $R^3$ and $R^4$ are independently selected from hydrogen, alkyl, alkoxy, carboxy, carboxyalkyl, aryl carboxyalkylaryl (e.g., carboxybenzyl ester), and cyano. Optionally, at least one of $R^1$, $R^2$, $R^3$, and $R^4$ is not hydrogen. In some embodiments, $R^5$, $R^6$, $R^7$, and $R^8$ are independently selected from hydrogen, alkyl, alkoxy, and halo. In some embodiments, $R^7$ and $R^8$ join together to form an aryl group, such as a phenyl moiety. In some embodiments, X is selected from oxygen, nitrogen (NH), and carbon ($CH_2$). In some embodiments, n is an integer selected from 0-1.

Also disclosed are pharmaceutical compositions that comprise the disclosed compounds with a carrier, diluent, or excipient. The pharmaceutical compositions may comprise an effective amount of the compounds (or salts thereof) for treating or preventing a disease, disorder, disorders, conditions, such as, but not limited to, viral infections, bacterial infections, fungal infections, tumor growth, allergic reactions, inflammatory conditions, cancer and cell proliferative disorders.

Also disclosed are methods of treating or preventing one of the aforementioned diseases or disorders that include administering the disclosed compounds in an effective amount to a subject in need thereof in order to treat or prevent the disease or disorder. For example, the compound may be formulated in a pharmaceutical composition and administered to a patient having or suspected of having a viral infection, bacterial infection, fungal infection, tumor growth, allergic reactions, inflammatory conditions, cancer and cell proliferative disorders.

DESCRIPTION OF THE DRAWINGS

FIG. 2 is a table summarizing exemplary reaction conditions for producing chromanes in accordance with some embodiments of the present disclosure. $^a$Yield determined by GC with bibenzyl as internal standard. Product was observed in a 1.2:1 dr ratio. $^b$Yield of isolated product. $^c$DIPEA used instead of HEH. $^d$Net$_3$ used instead of HEH. $^e$NBu$_3$ used instead of HEH. $^f$BT used instead of HEH. $^g$no light. DIPEA=diisopropylethylamine, NEt$_3$=triethylamine, BT=2-phenyl-dihydrobenzothaizoline.

DETAILED DESCRIPTION

Figure 1:
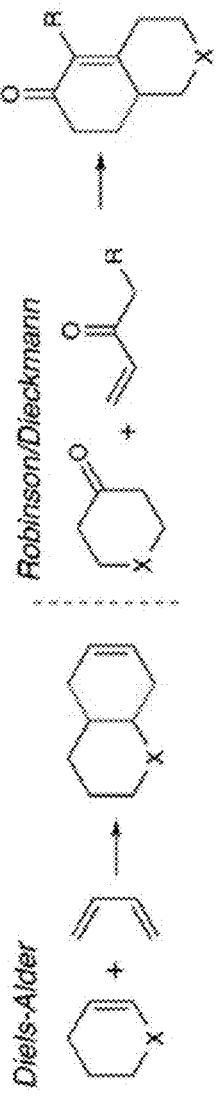
FIG. 1 are schematic illustrates of selected annulation strategies.
Figure 1:
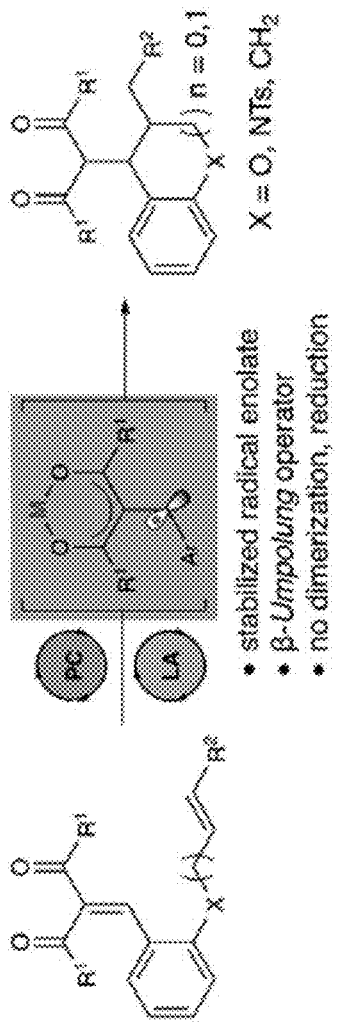
Figure 1:
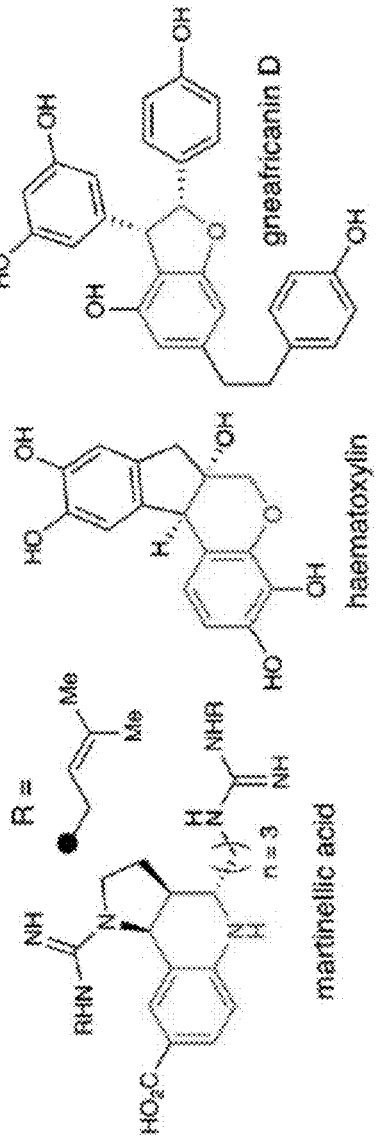

The present invention is described herein using several definitions, as set forth below and throughout the application.

Definitions

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

A "subject in need thereof" as utilized herein refers to a subject in need of treatment for a disease or disorder associated with a compound(s) disclosed herein, such as a substituted chromane. For example, a "subject in need thereof" may include a patient having a viral infection, bacterial infection, fungal infection, tumor growth, allergic reactions, inflammatory conditions, cancer and cell proliferative disorders. The term "subject" may be used interchangeably with the terms "individual" and "patient" and includes human and non-human mammalian subjects.

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched C1-C6 alkyl group). Exemplary alkylene groups include, but are not limited to —CH$_2$—, —CH$_2$CH$_2$—, —CH$_2$CH$_2$CH$_2$—, —CH(CH$_3$)CH$_2$—, —CH$_2$CH(CH$_3$)CH$_2$—, —CH(CH$_2$CH$_3$)CH$_2$—, and the like.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —$R^1C(O)N(R^2)$—, —$R^1C(O)N(R^2)R^3$—, —$C(O)NR^2R^3$, or —$C(O)NH_2$, wherein $R^1$, $R^2$ and $R^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Pharmaceutical Compositions and Formulations

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that modulates the chromanes activity may be administered as a single compound or in combination with another compound that modulates chromanes activity or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated with the substituted chromane's activity. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating one or more of the aforementioned diseases or disorders.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

Substituted Chromane Compounds, Analogs Thereof, and Methods of Use and Synthesis The disclosed compounds may have formula (I) as follows, or a salt or hydrate thereof.

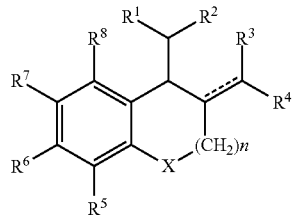

The compounds are optionally substituted. In some embodiments, $R^1$, $R^2$, $R^3$, and $R^4$, are independently selected from hydrogen, alkyl, alkoxy, cyano, carboxy, carboxyalkyl, aryl, and carboxylaryl. Optionally, at least one of $R^1$, $R^2$, $R^3$, and $R^4$ is not hydrogen.

In some embodiments, $R^5$, $R^6$, $R^7$, and $R^8$ are independently selected from hydrogen, alkyl, alkoxy, halo. In some embodiments, $R^7$ and $R^8$ form an aryl group, such as a phenyl moiety.

In some embodiments, X is selected from oxygen, nitrogen, and carbon. In some embodiments, n is an integer selected from 0 and 1.

In some embodiments, $R^1$ and/or $R^2$ is a carboxyalkyl, such as a branched or unbranched carboxy-$C_{1-6}$-alkyl. Non-limiting examples include —$CO_2$Me, —$CO_2$Et, —$CO_2$iPr, —$CO_2$tBu, where "Me" is methyl, "Et" is ethyl, and "iPr" is isopropyl, and "tBu" is tert-butyl. In some embodiments, at least one of $R^5$, $R^6$, and $R^7$ is a halo moiety, such as bromo, fluoro, and cloro. In some embodiments, at least one of $R^5$, $R^6$, and $R^7$ is a branched or unbranched $C_{1-6}$-alkyl, such as methyl, ethyl, propyl, or tert-butyl.

In some embodiments, $R^3$ and/or $R^4$ is hydrogen.

In some embodiments, $R^3$ and/or $R^4$ is selected from phenyl, branched or unbranched carboxy-$C_{1-6}$-alkyl, cyano, and carboxyaryl.

Exemplary compounds as contemplated herein may include, but are not limited to compounds having a formula selected from:

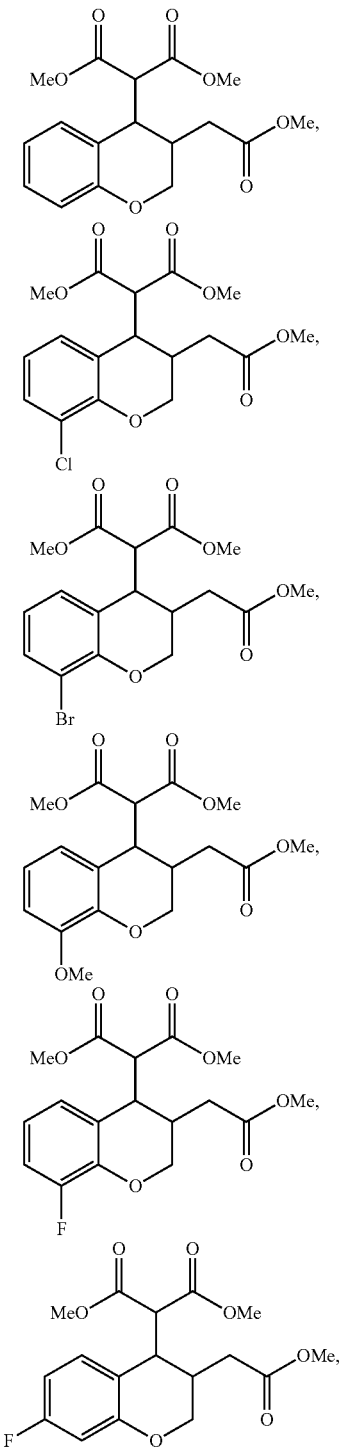

-continued
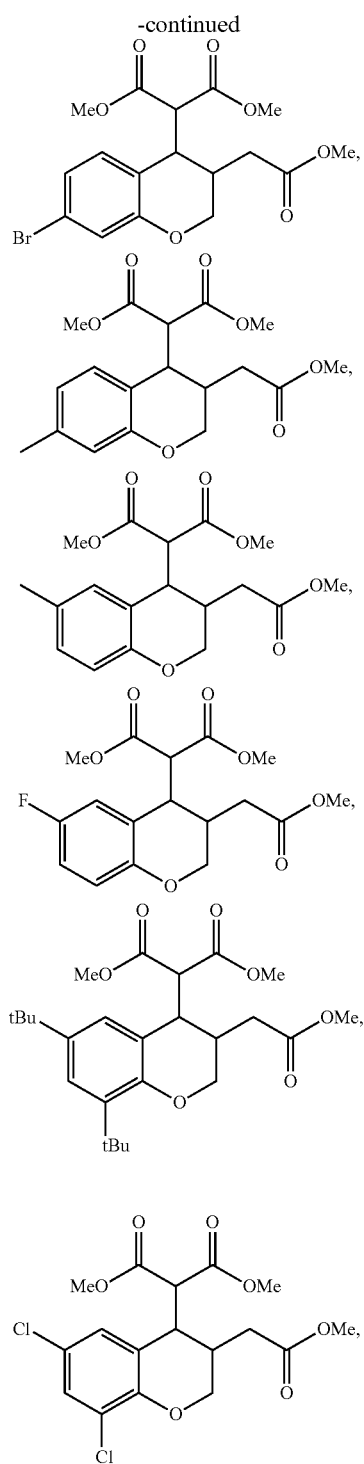
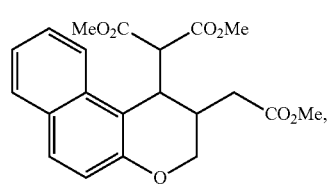
-continued
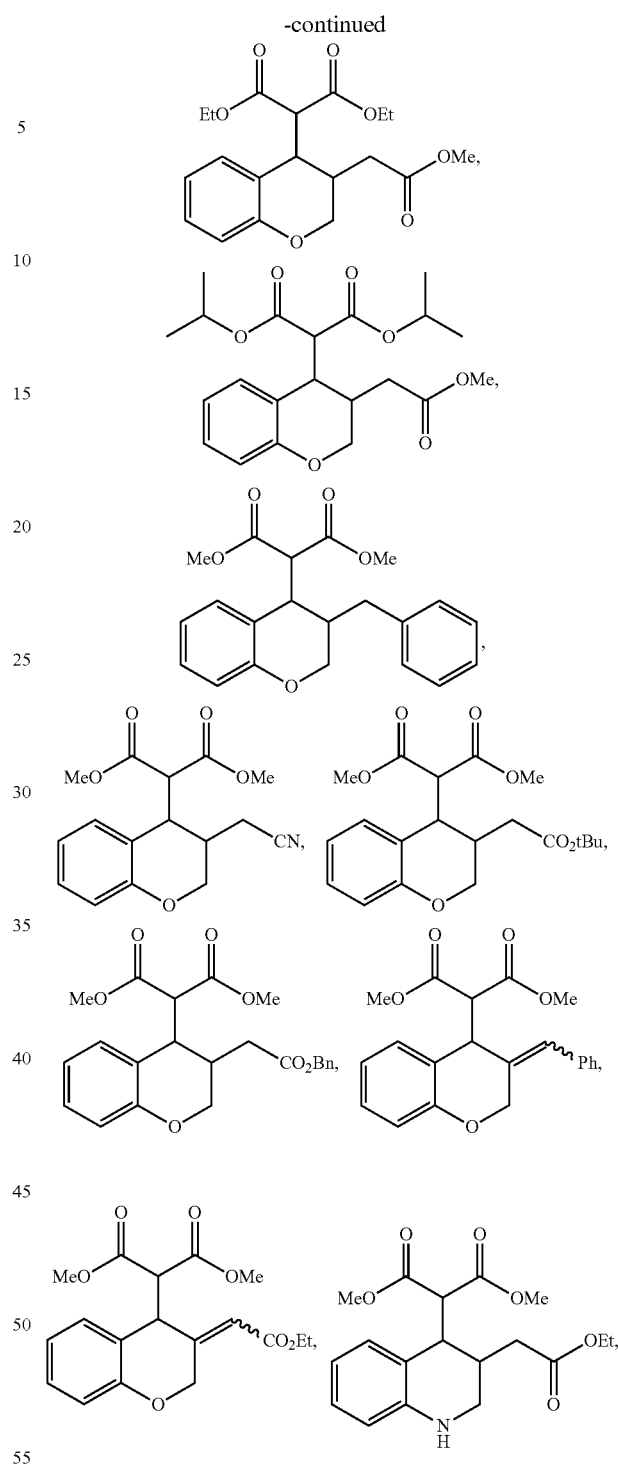
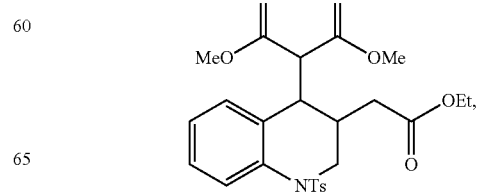

-continued

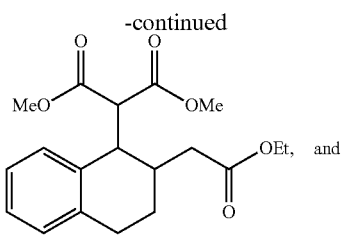

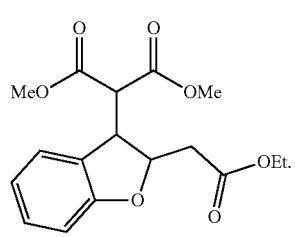

The disclosed compounds may be post-processed using a number of reactions including, but not limited to, decarboxylation and condensation reactions, for example, Krapcho decarboxylations and Dieckmann condensations. In some embodiments, the disclosed compounds may be post-processed by methods comprising reacting reagents comprising a compound having the formula (I) described above, a polar aprotic solvent (e.g., DMSO), an effective amount of water (e.g., 1-5 equivalents relative to the compound having formula (I)), an inorganic salt (e.g., LiCl, NaCl, KOAc), and heat (e.g., 100-200° C.).

As one non-limiting example, the disclosed compounds may be post-processed to produce a compound having formula (II) as follows, or a salt or hydrate there:

II

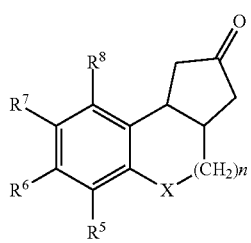

The compounds of formula II are optionally substituted. In some embodiments, $R^5$, $R^6$, $R^7$, and $R^8$ are independently selected from hydrogen, alkyl, alkoxy, halo. In some embodiments, $R^7$ and $R^8$ form an aryl group, such as a phenyl moiety.

In some embodiments of the compounds of formula II, X is selected from oxygen, nitrogen, and carbon. In some embodiments, n is an integer selected from 0 and 1.

The disclosed compounds may be synthesized by methods involving cooperative Lewis acid/photoredox reductive enolate annulation reactions. In some embodiments, the disclosed compounds may be prepared by methods comprising reacting reagents comprising:

(a) a compound having a formula selected from

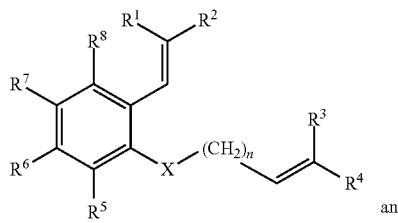

and

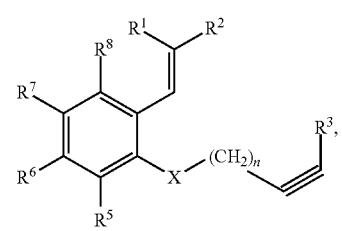

wherein:

$R^1$ and $R^2$ are independently selected from hydrogen, alkyl, alkoxy, carboxy, and carboxyalkyl;

$R^3$ and $R^4$ are independently selected from hydrogen, alkyl, alkoxy, carboxy, carboxyalkyl, aryl, carboxyalkylaryl (e.g., carboxybenzyl ester), and cyano;

$R^5$, $R^6$, $R^7$, and $R^8$ are independently selected from hydrogen, alkyl, alkoxy, or $R^7$ and $R^8$ form an aryl group, such as a phenyl moiety;

Optionally, wherein at least one of $R^1$, $R^2$, $R^3$, and $R^4$, is not hydrogen;

X is selected from oxygen, nitrogen (NH), and carbon ($CH_2$); and n is an integer selected from 0-1, (b) a photocatalyst; and (c) a Lewis acid;

wherein the reagents react in a cooperative Lewis acid/photoredox reductive enolate annulation reaction. The reagents utilized in the cooperative Lewis acid/photoredox reductive enolate annulation reaction further may include a reducing agent such as Hantzsch ester (HEH), or hydrogen atom donors such as tertiary amines (e.g., N,N-diisopropylethylamine (DIPEA), triethylamine ($NEt_3$), tributylamine ($NBu_3$), and BT.

The disclosed compounds, salts thereof, and/or hydrates thereof may be formulated as pharmaceutical compositions comprising the compounds, salts thereof, and/or hydrates thereof, in a pharmaceutically acceptable carrier. The pharmaceutical compositions may be formulated for treating one or more of the aforementioned diseases or disorders.

In some embodiments, the disclosed compounds may be used for treating a subject in need of treatment. The methods may include administering to the subject the disclosed compound(s) or compositions comprising the disclosed compounds in an effective amount to treat the disease or disorder. Disease and disorders may include, but are not limited to, viral infection, bacterial infection, fungal infection, tumor growth, allergic reactions, inflammatory conditions, cancer and cell proliferative disorders.

ILLUSTRATED EMBODIMENTS

The following Embodiments are illustrative and should not be interpreted to limit the claimed subject matter.

Embodiment 1. A compound of the following formula or a salt or hydrate there:

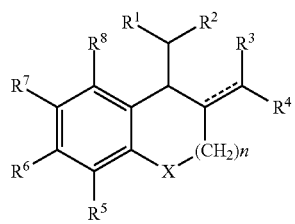

wherein $R^1$ and $R^2$ are independently selected from hydrogen, alkyl, alkoxy, carboxy, and carboxyalkyl, $R^3$ and $R^4$ are independently selected from hydrogen, alkyl, alkoxy, carboxy, carboxyalkyl, aryl, carboxyalkylaryl (e.g., carboxybenzyl ester), and cyano, optionally, wherein at least one of $R^1$, $R^2$, $R^3$, and $R^4$, is not hydrogen, X is selected from oxygen, nitrogen (NH), and carbon ($CH_2$), n is an integer selected from 0-1.

Embodiment 2. The method of embodiment 1, wherein $R^1$ and/or $R^2$ is carboxyalkyl.

Embodiment 3. The method of embodiment 2, wherein the carboxyalkyl is a branched or unbranched carboxy-$C_{1-6}$-alkyl.

Embodiment 4. The method of embodiment 2, wherein the carboxyalkyl is carboxymethyl.

Embodiment 5. The method of embodiment 2, wherein the carboxyalkyl is carboxyethyl.

Embodiment 6. The method of embodiment 2, wherein the carboxyalkyl is carboxyisopropyl.

Embodiment 7. The method of embodiment 1, wherein at least one of $R^5$, $R^6$, and $R^7$ is bromo.

Embodiment 8. The method of embodiment 1, wherein at least one of $R^5$, $R^6$, and $R^7$ is fluoro.

Embodiment 9. The method of embodiment 1, wherein at least one of $R^5$, $R^6$, and $R^7$ is chloro.

Embodiment 10. The method of embodiment 1, wherein at least one of $R^5$, $R^6$, and $R^7$ is a branched or unbranched $C_{1-6}$-alkyl.

Embodiment 11. The method of embodiment 1, wherein at least one of $R^5$, $R^6$, and $R^7$ is methyl.

Embodiment 12. The method of embodiment 1, wherein at least one of $R^5$, $R^6$, and $R^7$ is tert-butyl.

Embodiment 13. The method of embodiment 1, wherein $R^7$ and $R^8$ join together to form an aryl group.

Embodiment 14. The method of embodiment 1, wherein $R^3$ or $R^4$ is hydrogen.

Embodiment 15. The method of embodiment 1, wherein $R^3$ is hydrogen and $R^4$ is selected from the group consisting of phenyl, branched or unbranched carboxy-$C_{1-6}$-alkyl, cyano, and carboxyalkylaryl (e.g., carboxybenzyl).

Embodiment 16. The method of embodiment 1, having a formula selected from:

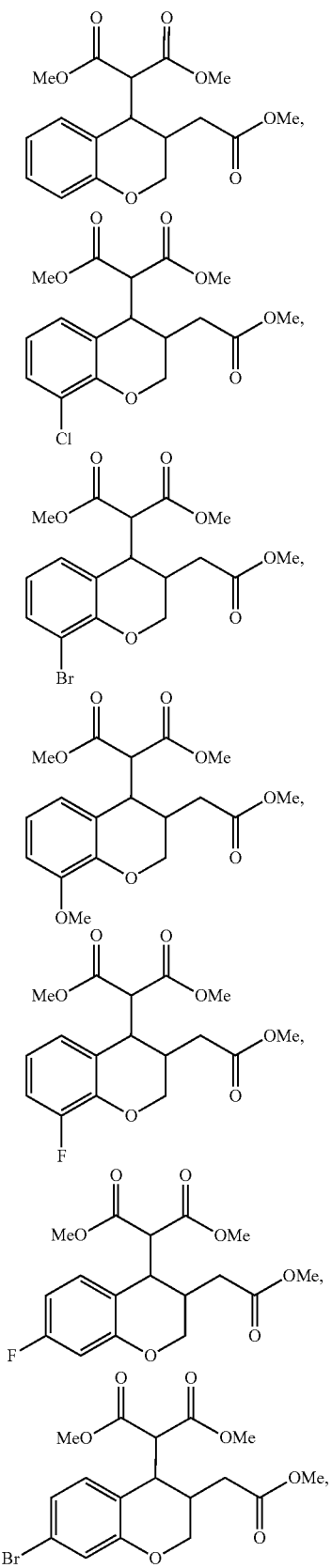

-continued
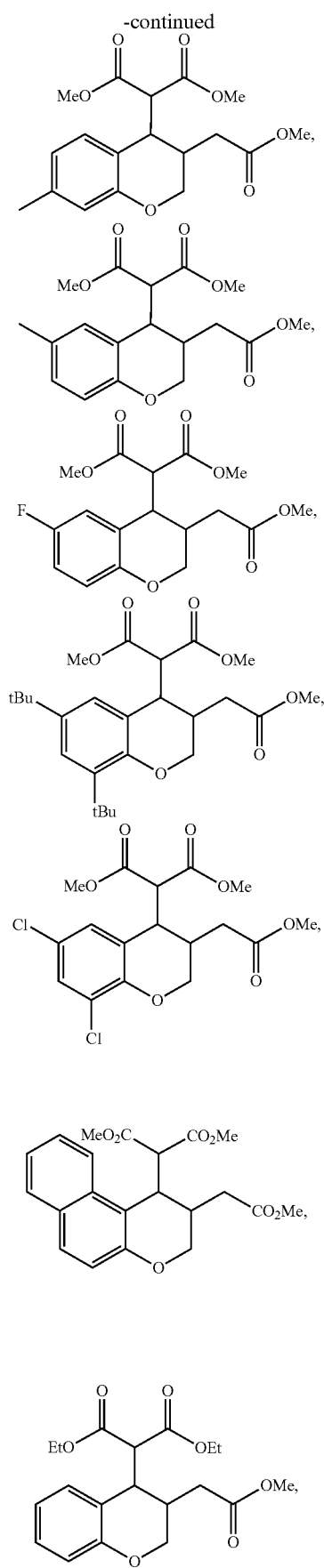
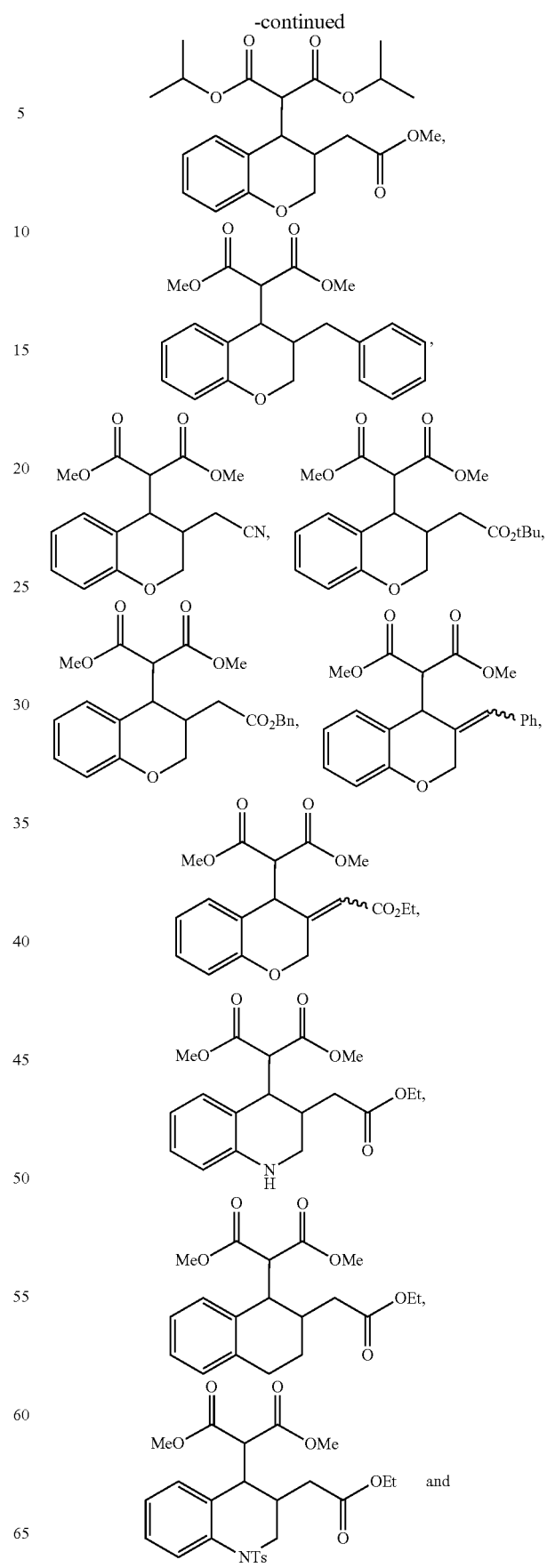

-continued

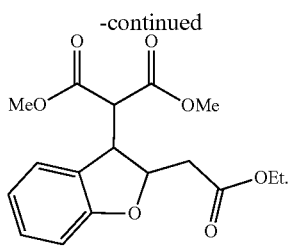

Embodiment 17. A pharmaceutical composition comprising an effective amount of any of the compounds of embodiments 1-16 together with at least one of a carrier, excipient, or diluent.

Embodiment 18. A method of treating a subject in need of treatment, the method comprising administering the composition of claim 17 to the subject in an effective amount to treat a disease or disorder.

Embodiment 19. A method of synthesizing any of the compounds of claims 1-16, the method comprising reacting reagents comprising:
(a) a compound having a formula selected from

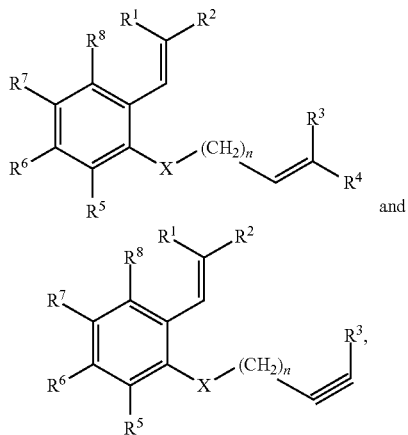

wherein $R^1$ and $R^2$ are independently selected from hydrogen, alkyl, alkoxy, carboxy, and carboxyalkyl, $R^3$ and $R^4$ are independently selected from hydrogen, alkyl, alkoxy, carboxy, carboxyalkyl, aryl, carboxyalkylaryl (e.g., carboxybenzyl ester), and cyano, $R^5$, $R^6$, $R^7$, and $R^8$ are independently selected from hydrogen, alkyl, alkoxy, halo or $R^7$ and $R^8$ form an aryl group, such as a phenyl moiety; optionally, wherein at least one of RI, $R^2$, $R^3$, and $R^4$, is not hydrogen, X is selected from oxygen, nitrogen (NH), and carbon ($CH_2$); and n is an integer selected from 0-1.
(b) a photocatalyst; and (c) a Lewis acid, wherein the reagents react in a cooperative Lewis acid/photoredox reductive enolate annulation reaction.

Embodiment 20. The method of embodiment 19, wherein the reagents further comprise a reducing agent.

EXAMPLES

The following Examples are illustrative and are not intended to limit the scope of the claimed subject matter.

Reference is made to the manuscript Betori et al., "Reductive Annulations of Arylidene Malonates With Unsaturated Electrophiles Using Photoredox/Lewis Acid Cooperative Catalysis," Chem. Sci., 2019, 10, 3353, Feb. 6, 2019, the content of which is incorporated by reference in its entirety.

Abstract

A cooperative Lewis acid/photocatalytic reduction of salicylaldehyde-derived arylidene malonates provides access to a versatile, stabilized radical anion enolate. Using these unusual umpolung operators, we have developed a route to access densely functionalized carbo- and heterocycles through a radical annulation addition pathway.

Introduction

The development of annulation strategies has proved invaluable in organic synthesis, particularly for the construction of complex natural products.[1] In a broad sense, annulation reactions can be divided into two electron and one electron approaches, where two electron annulation tactics include the venerable Diels-Alder, Michael and Dieckmann reactions, as well as general nucleophilic additions and alkylations. Conversely, one-electron annulation methods have focused on using halogenated starting materials and tin reagents, where seminal reports by Curran and Stork were revolutionary for the advent of radical annulations.[2] Despite these elegant approaches, the use of stoichiometric tin hydrides is problematic both due to toxicity and purification problems, driving the need for the development of radical annulation reactivity accessed through catalytic methods using non-prefunctionalized starting materials.[3] The development of photoredox chemistry has rendered the catalytic generation of open shell intermediates relatively facile due to the natural abundance and ease of use of visible light, as well as the superior chemoselectivity observed compared with traditional methodologies for radical-based approaches.[4]

Along these lines, the use of photoredox chemistry to access inverse polarity concepts, termed umpolung, have emerged as instrumental.[5] Specifically, the generation of ketyl radical species (e.g. dl umpolung operators) through the reduction of carbonyl derivatives has been a major focus.[6] Since carbonyls are typically characterized by strongly negative redox potentials ($E_{1/2}$red=−1.93 V vs. SCE for benzaldehydes),[7] the development of cooperative catalytic systems to effect said reduction potential have been highly explored to afford annulations, reductive couplings and radical-radical couplings (FIG. 1).[8]

Similarly, d3 umpolung operators in photoredox have been explored.[9] Yoon et al. pioneered a cooperative catalytic approach to enone β-umpolung reactivity using a photoredox/Lewis acid approach to afford [2+2], and [3+2]cycloadditions.[10] Following Yoon's seminal work on enone β-umpolung reactivity, recent reports have focused on using bifunctional and cooperative catalytic approaches in photoredox catalysis to access new chemical reactivity.[11] However, new directions and opportunities remain unexplored in this area, primarily due to the inherent limitations of bifunctional catalytic manifolds, which restrict reactivity and generalizability as well.

As part of our program to generate new opportunities in β-umpolung chemistry, we recently reported the use of arylidene malonates as substrates in photoredox/Lewis acid cooperative catalysis to afford radical-radical cross coupling, radical dimerizations, and transfer hydrogenations.[12] One goal of this study was to design a stabilized β3-umpolung operator intermediate, with the hypothesis that a more stabile radical anion would enable underexplored chemical reactivity, namely intermolecular radical couplings, rather than the dimerization reactions often seen with enone-derived radical anions (e.g. cinnamates, $E_{1/2}$ red=−2.3 V vs. SCE).[13] In this regard, we demonstrated that arylidene malonates ($E_{1/2}$ red=−1.57 V for phenyl arylidene malonate vs. SCE),[14] demonstrated a drastic shift in reduction potential upon complexation with a Lewis acid ($E_{1/2}$ red=−0.37 V for phenyl arylidene malonate vs. SCE). By utilizing arylidene malonates, this cooperative catalytic approach afforded a stabilized β-radical enolate intermediate exhibiting reactivity divergent from reductive species generated from conventional enones, presumably due to greater persistence of the resonance-stabilized radical anion. Herein, we report a cooperative Lewis acid/photoredox reductive enolate annulation strategy to provide densely functionalized carbo and heterocycles.

Figure 2:
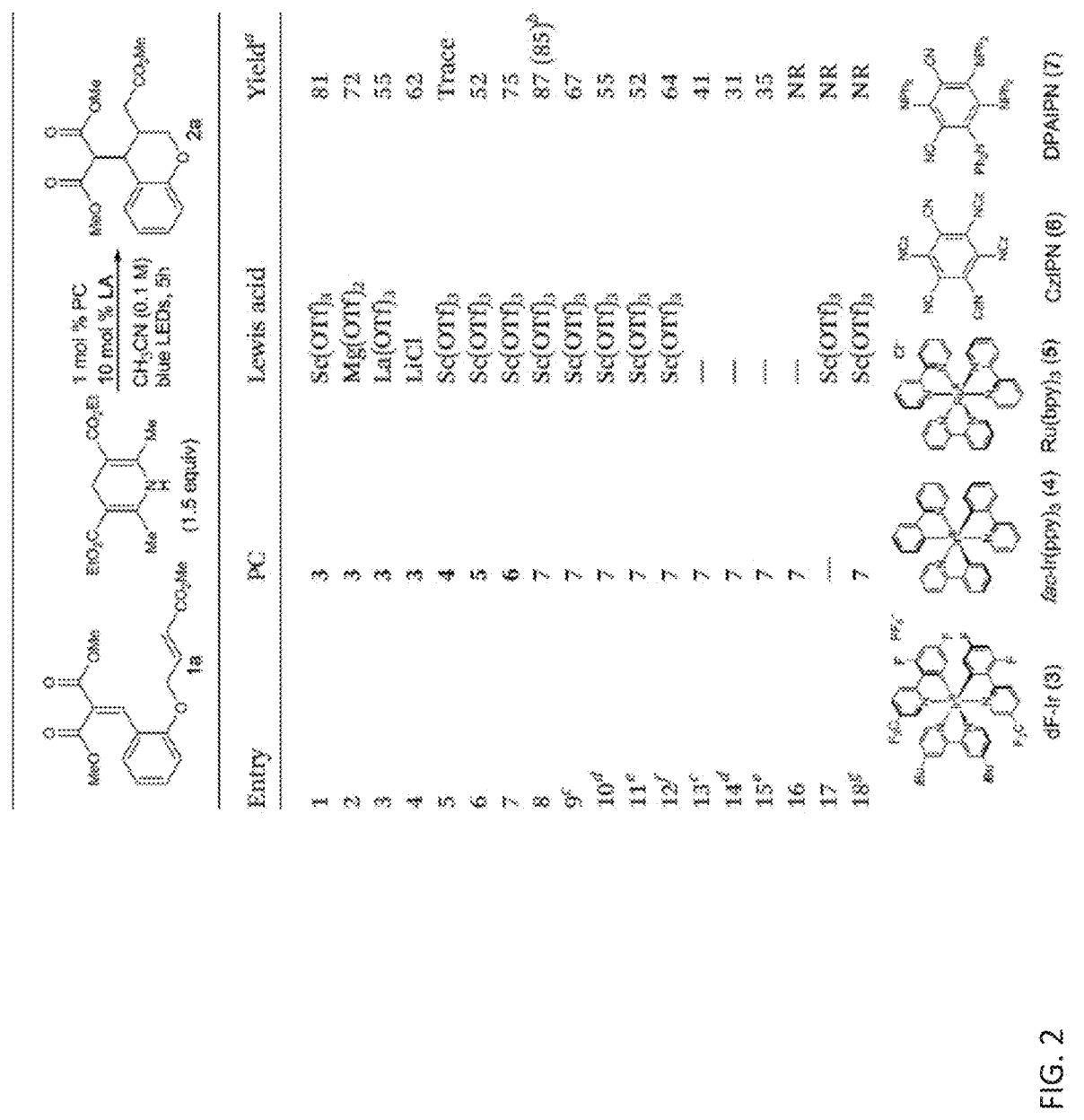

Chroman and related heterocycles are a diverse class of bioactive small molecules that our lab have previously prepared and investigated for their wide range of biological activities in anti-cancer models.[15] We envisioned that the arylidene malonate-derived β-umpolung operator could grant access to previously unprepared derivatives. We initiated our studies with 1a, which was readily accessible in 2 steps from salicylaldehyde, using a variety of photocatalysts and blue LEDs, the results of which are summarized in FIG. 2. Gratifyingly, we found that the desired chromane product was formed with scandium triflate in acetonitrile using photocatalyst dF-Ir and Hantzsch ester (HEH) in 81% yield with a 1.2:1 dr. A variety of other bidentate Lewis acids were investigated, all of which were capable of affording the title reaction, albeit with decreased yield in comparison to scandium triflate (entries 1-4). A survey of transition metal photocatalysts identified dF-Ir as optimal.

Organocatalysts of the dicyanobenzene family performed as well as dF-Ir, with diphenyl aniline organocatalyst DPAIPN[16] providing the desired product in comparable 85% yield and diastereoselectivity. Solvent evaluation confirmed acetonitrile to be the optimal solvent, whereas aprotic and protic were shown to be less successful. Evaluations of alternative stoichiometric hydrogen atom donors (DIPEA, $NEt_3$, $NBu_3$, BT) were capable of delivering 2a in slightly decreased yields relative to the HEH; where a slight increase in diastereoselectivity was observed (2:1 dr observed with $NEt_3$) at a precipitous loss of yield (entries 9-12). The rationale for this observed increase in diastereoselectivity could be due to coordination from the radical cation of $NEt_3$ with the malonate, providing a facial selectivity to facilitate increased diastereoselectivity, or that the C—C bond formation is reversible and that the diastereoselectivity is determined, at least in part, by the relative rates of hydrogen atom transfer. As tertiary amines have been used previously for activation of carbonyls for reduction, we evaluated DIPEA, $NEt_3$ and $NBu_3$ in the absence of $Sc(OTf)_3$, where drastically lower yields were observed (entries 13-15). In this instance, it is believed that upon initial single electron reduction, the oxidized nitrogen atom in DIPEA, $NEt_3$ or $NBu_3$ can form a 2-center/3-e-interaction,[17] or after a [1,2]-H shift, can serve a hydrogen-bond donor,[18] which results in the oxidized amine serving as both the terminal reductant and the Lewis acid necessary for activation of 1a.[8d,c] A series of control experiments demonstrated that the reaction did not take place in the absence of light, photocatalyst or Lewis acid (entries 16-18).

Figure 3:
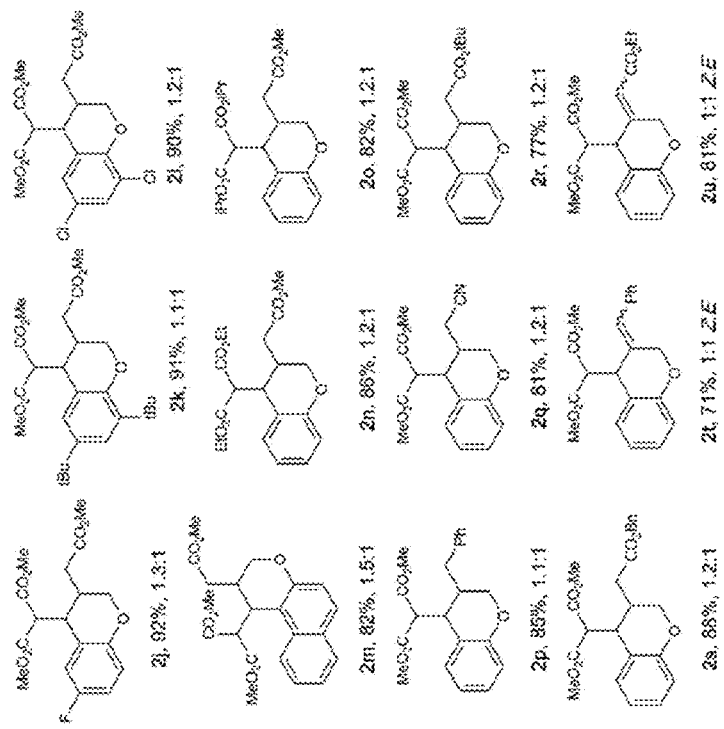
FIG. 3 is a table summarizing exemplary reaction conditions for producing chromanes in accordance with some embodiments of the present disclosure. Reaction conditions: 1 (0.2 mmol), HEH (0.3 mmol), PC 7 (1 mol %), Sc(OTf)$_3$ (10 mol %), degassed CH$_3$CN (2.0 mL) was irradiated with a blue LED (456 nm) for 5 h. Reported yields are determined after isolation by column chromatography.
Figure 3:
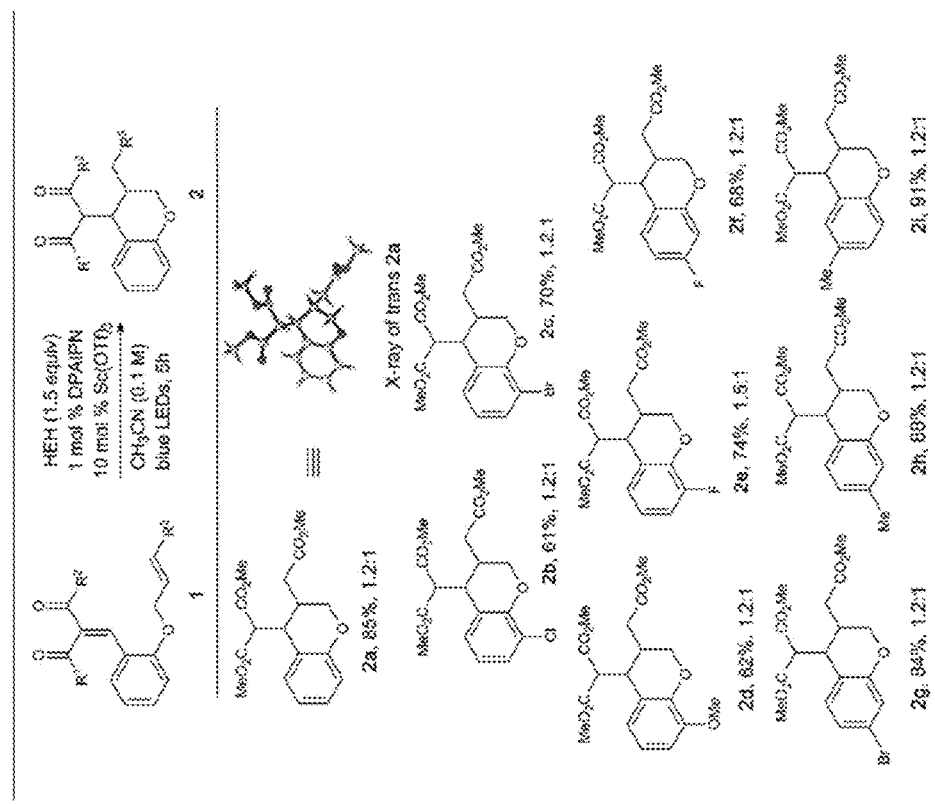

With these optimized conditions, we investigated a variety of substrates (FIG. 3). Generally, the desired products were obtained in good to excellent yields. Substrates bearing either electron-rich and electron-poor substituents were well tolerated; however, substrates with substitution at the 6-position did not provide the desired product, presumably due to reduced overlap between the enone and aryl R-systems. Diversity could be introduced into the dicarbonyl moiety to tolerate a variety of diesters (2n, 2o) in good to excellent yields, albeit as a complex mixture of diastereomers. The unsaturated electrophile could be varied to facilitate access to benzyl (2p) and nitrile (2q) substituted chromanes in excellent yields. Replacement of the olefin electrophile with alkyne electrophiles proceeded with excellent yields (2t, 2u), albeit as a mixture of Z/E isomers.

Figure 4:
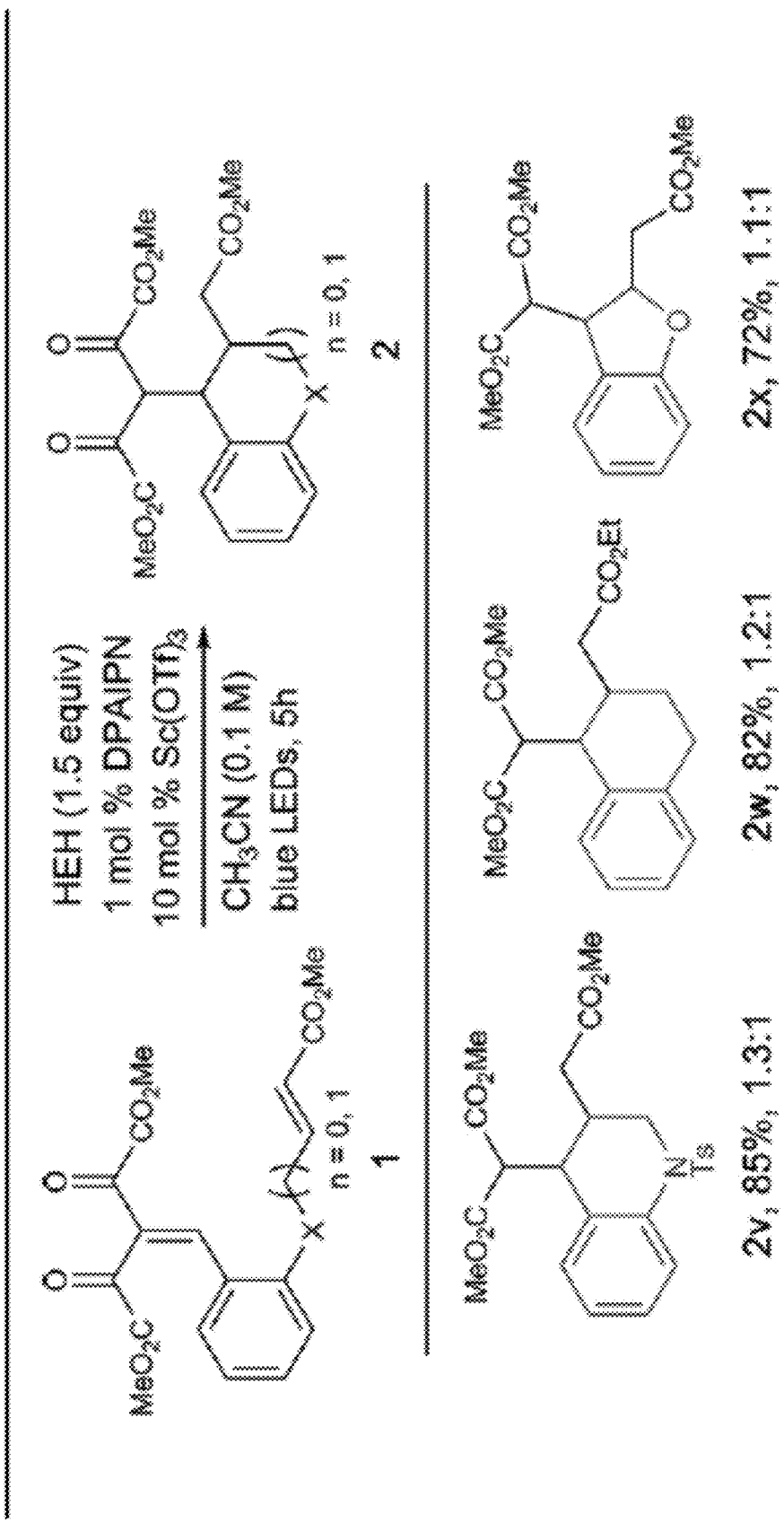
FIG. 4 is an example reaction scheme for producing chromanes in accordance with some embodiments of the present disclosure. Reaction conditions: 1 (0.2 mmol), HEH (0.3 mmol), PC 7 (1 mol %), Sc(OTf)$_3$ (10 mol %), degassed CH$_3$CN (2.0 mL) was irradiated with a blue LED (456 nm) for 5 h. Reported yields are determined after isolation by column chromatography.

Furthermore, we were pleased to find that modification of the starting material to access tetrahydroquinolines (2v) and tetrahydronaphthalenes (2w) were also successful in high yields, illustrating the capability of this methodology to access a wide range of carbo and heterocyclic scaffolds in high efficiency. Attempts to access dihydrobenzofuran was successful, albeit with slightly diminished yields (2x, 72% yield), where the remaining mass balance is the saturated arylidene malonate species. This is presumably due to the decreased electrophilicity of the vinylogous carbonate starting material due to hyperconjugation (FIG. 4).[19]

Figure 5:
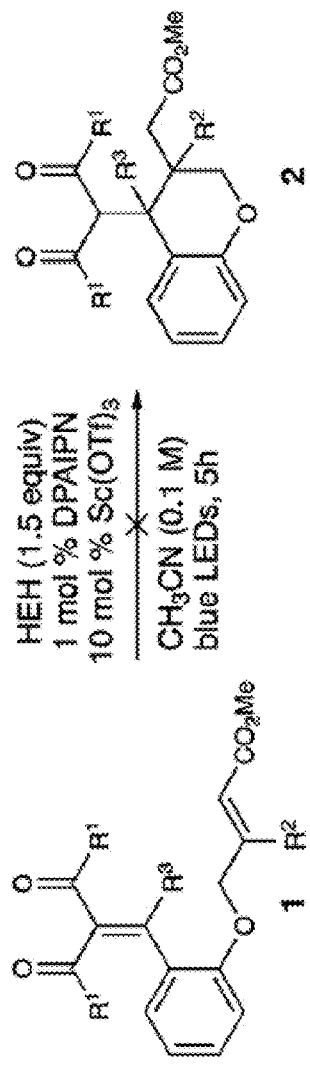
FIG. 5 is an example reaction scheme for producing chromanes in accordance with some embodiments of the present disclosure.
Figure 5:
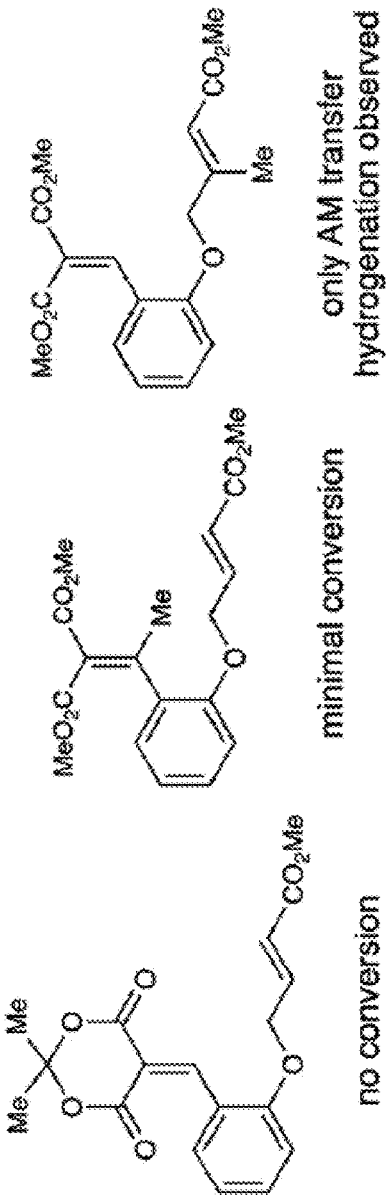
Figure 5:
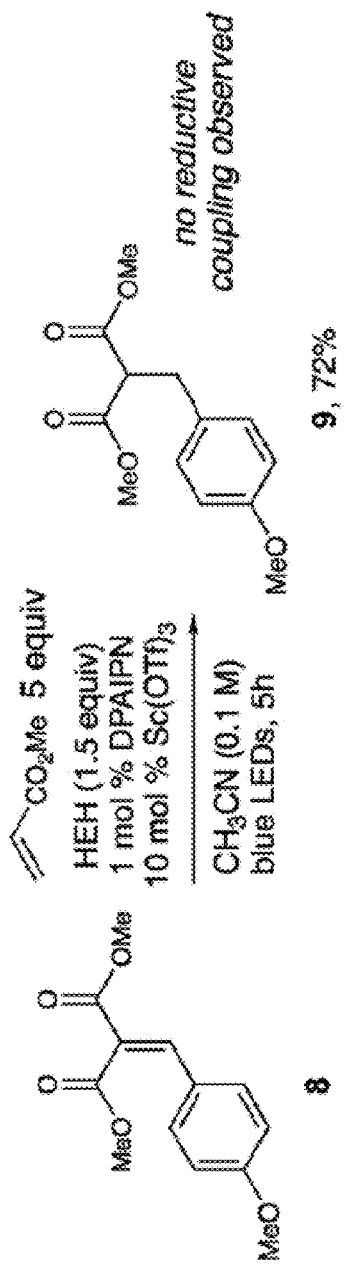

Substrates designed to allow access to quaternary centers (either derived from 2'-hydroxyacetophenone or from senecioic acid) were not successful under the specified conditions, presumably due to decreased reactivity of the resulting β-radical enolate intermediate and decreasing electrophilicity of the tethered alkene respectively. The importance of the dicarbonyl moiety was validated as a means for Lewis acid coordination, as substrates derived from Meldrum's acid showed no conversion under the optimized conditions. An intermolecular reductive coupling between 8 and methyl acrylate was unsuccessful, where only transfer hydrogenation to afford 9 was observed. This likely indicates that reduction of the resulting radical anion proceeds more rapidly than radical conjugate addition (FIG. 5).

Figure 6:
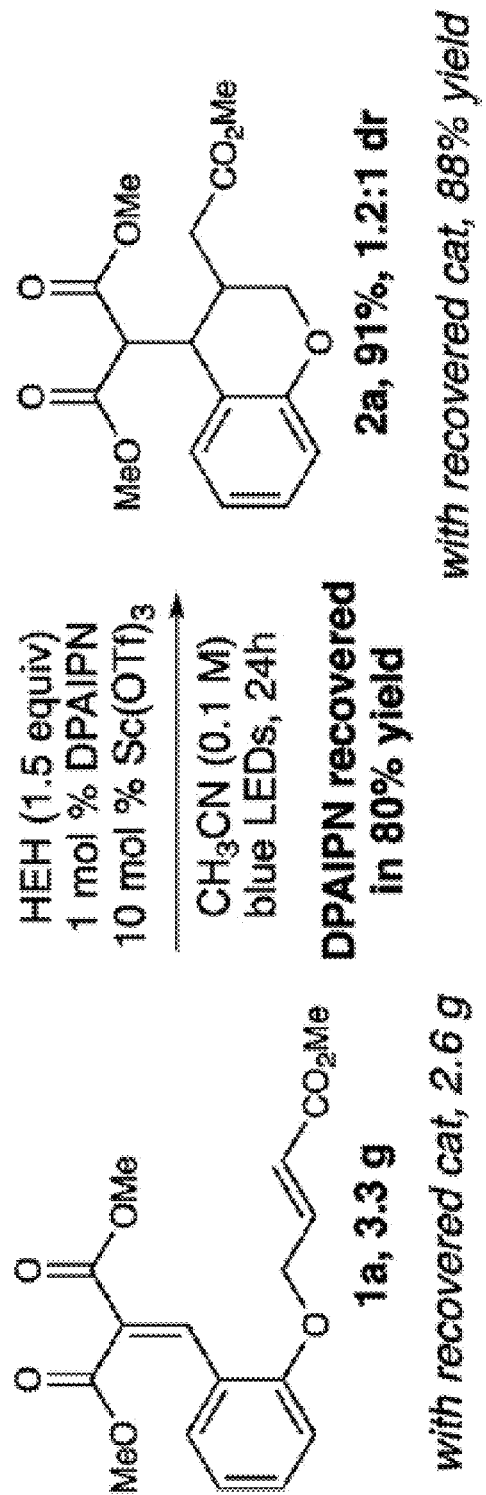
FIG. 6 is an example reaction scheme for producing chromanes in accordance with some embodiments of the present disclosure.

Notably, we were able to demonstrate this reaction on multi-gram scale, where 2a was accessed in similar yields under identical reaction conditions, further highlighting the potential of this reaction. Additionally, the DPAIPN photocatalyst was recovered after column chromatography in 80% yield. The recovered DPAIPN was subsequently used in a multi-gram scale reaction without loss of yield, giving this methodology additional utility due to the ability to recover and reuse the catalyst (FIG. 6).

Figure 7:
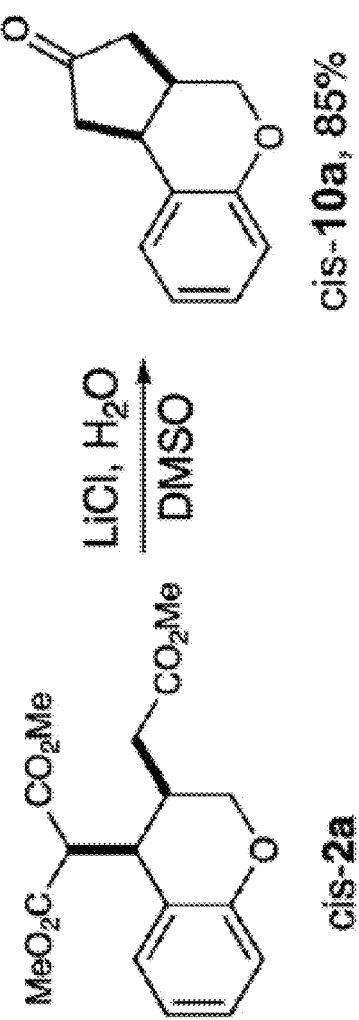
FIG. 7 is an example reaction scheme for producing chromanes in accordance with some embodiments of the present disclosure.

A practical advantage of this strategy is the ease of synthetically elaborating these products. A one-pot Krapcho/Dieckmann/Krapcho sequence with cis-2a proceeded in 85% yield, affording an interesting [6,6,5] fused ring system (FIG. 7).

Figure 8:
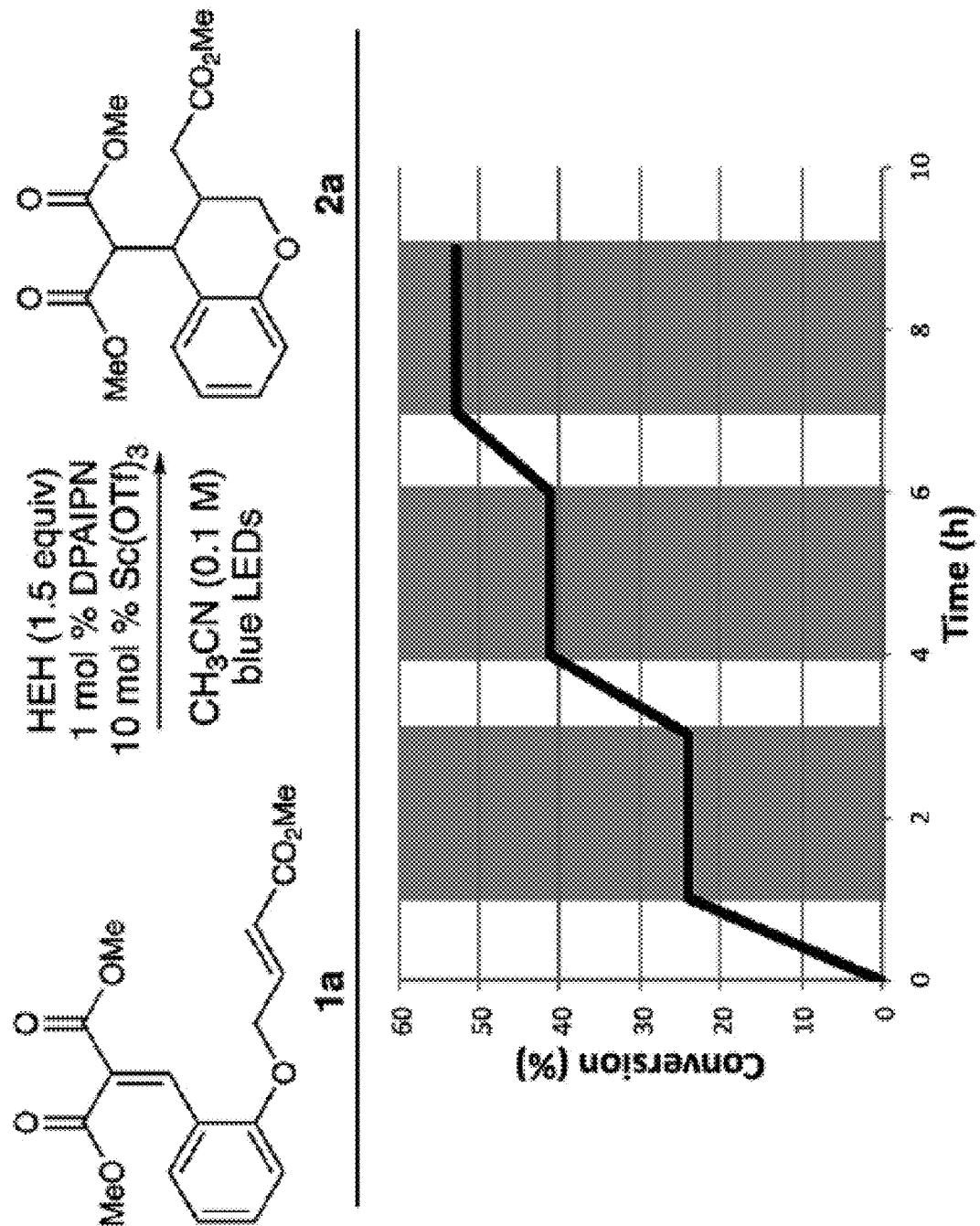
FIG. 8 is an example reaction scheme for producing chromanes and the conversion over time in accordance with some embodiments of the present disclosure.

To probe the mechanism of this process, we investigated whether this photoredox process can propagate through a chain process rather than the presumed closed-catalytic photoredox cycle.[20] We were pleased to find that upon using a "light/dark" experiment[21] that product formation was only observed during periods of irradiation (FIG. 8). While supporting our mechanistic hypothesis, "light/dark" experiments are typically not sufficient to fully elucidate whether a process proceeds through a closed-catalytic cycle as opposed to a propagating chain process.[22]

As a follow up to these studies, we demonstrated that this reaction has a quantum yield of 1.0, indicating that the reaction does not propagate through a radical chain process.

To further understand the nature of the $Sc(OTf)_3/1a$ complex, UV-Vis spectroscopic characterization was carried out. Interestingly, the $Sc(OTf)_3/1a$ complex demonstrated a considerable difference in the UV-Vis spectrum relative to 1a alone, where there is an additional shoulder peak around 380-410 nm. While this demonstrates that the Sc(OTf)$_3$/1a complex can absorb blue LED light, no reactivity is observed without the DPAIPN photocatalyst present, indicating that it is unlikely that the Sc(OTf)$_3$/1a complex can generate any intermediates that result in consumption of Ta. To confirm that the Sc(OTf)$_3$/1a complex does not undergo productive photoredox reaction pathways in the absence of DPAIPN, we irradiated Ta with 10 mol % Sc(OTf)$_3$ and superstoichiometric DIPEA, NEt$_3$, NBu$_3$ and HEH. No conversion of 1a was observed in any case. Finally, the UV-Vis profile of 1a showed no change in the presence of either DIPEA, NEt$_3$ or NBu$_3$ (100 mol %), indicating that the amines themselves are not interacting with Ta, but instead need to undergo a single electron reduction to complex with Ta.

Figure 9:
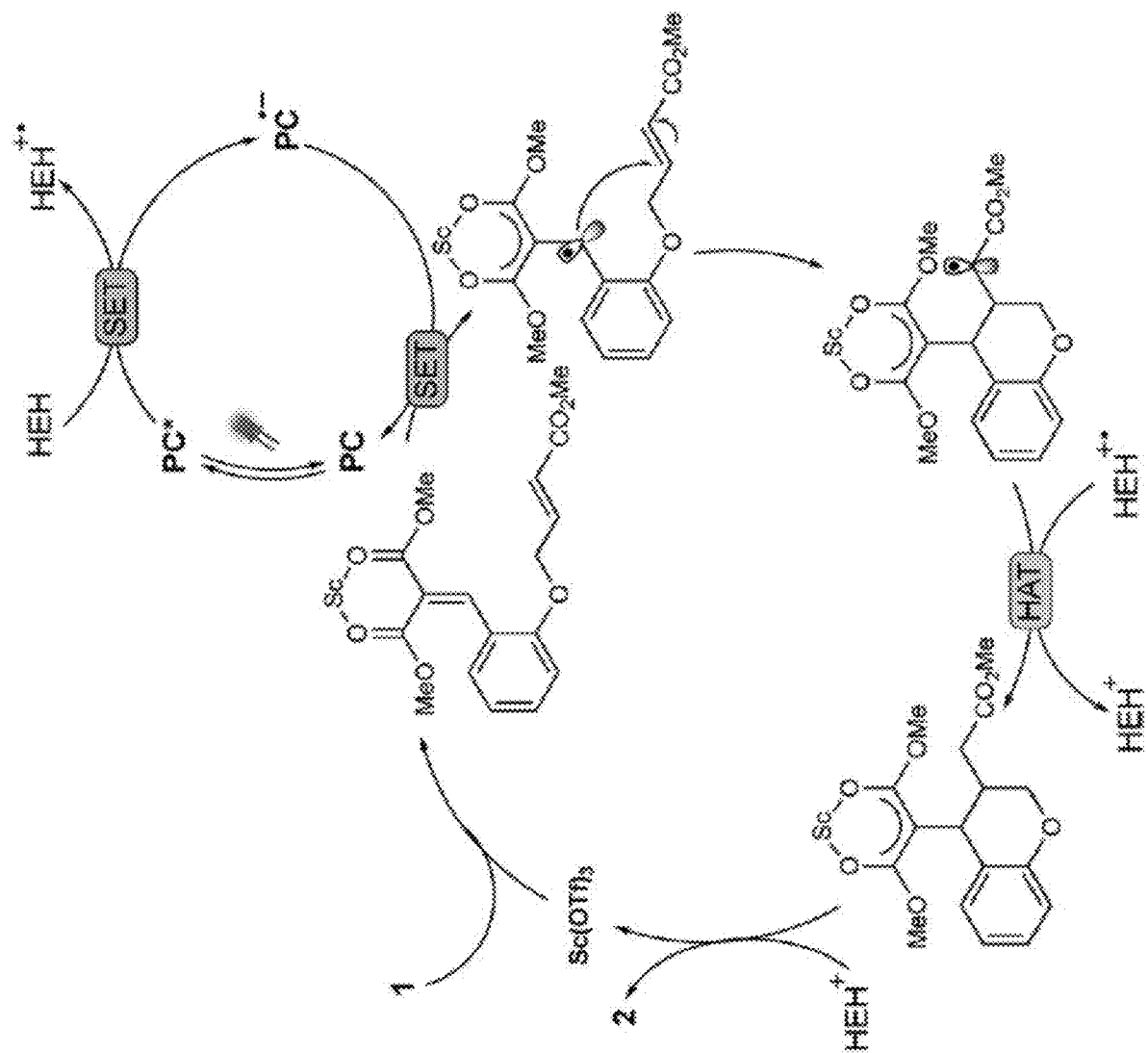
FIG. 9 is a schematic illustration of a reaction mechanism for producing a chromane in accordance with some embodiments of the present disclosure.
Figure 10:
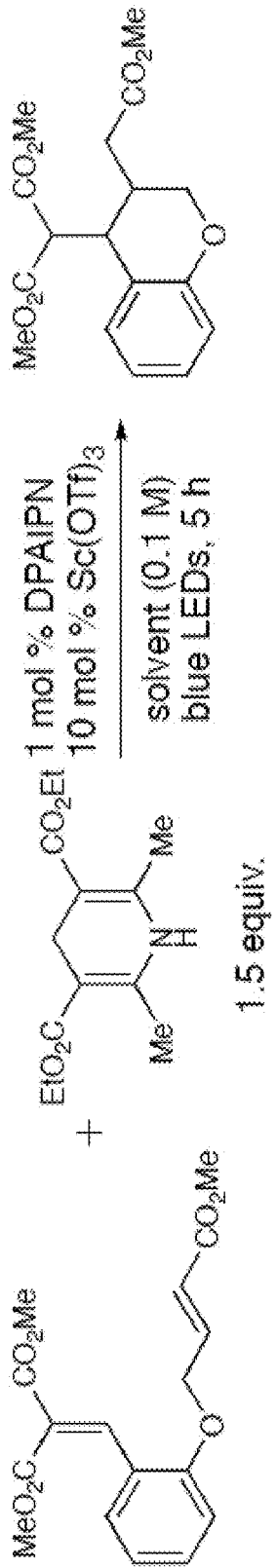
FIG. 10 provides a table illustrating the effect of various solvents.

Without wishing to be bound to any particular theory, it is contemplated that the mechanism occurs under the reactivity illustrated in FIG. 9: irradiation with visible light results in the formation of excited DPAIPN photocatalyst, a capable oxidant (E$_{1/2}$ ox=1.10 V vs. SCE). Reduction of the resulting DPAIPN excited state by HEH (E$_{1/2}$ ox=0.89 V vs. SCE) furnishes a strongly reducing DPAIPN catalyst (E$_{1/2}$ red=– 1.52 V vs. SCE). Subsequently, the reduced DPAIPN species transfers an electron to the Lewis acid-arylidene malonate complex, producing the nucleophilic radical anion and regenerating the ground state DPAIPN catalyst. The radical anion is able to add into the unsaturated bond, forming the chromane ring and a stabilized radical, which upon hydrogen atom transfer from the corresponding HEH radical cation, leads to the enolate complex. Subsequent proton transfer from the protonated HEH leads to the desired product.

Conclusions

A Lewis acid/photoredox cooperative catalytic manifold is capable of generating stabilized radical anion species from salicylaldehyde-derived arylidene malonates has been developed. This reactive intermediate undergoes intramolecular conjugate addition with pendent unsaturated electrophiles to afford structurally diverse chromanes. This platform sets the stage for further development of β-umpolung reactivity via photoredox catalysis, which is currently underway in our laboratory.

Materials/Reactions:

All reactions were carried out under an argon or nitrogen atmosphere in flame-dried glassware with magnetic stirring. Solvents used in reactions were purified by passage through a bed of activated alumina. Unless stated otherwise, reagents were purified prior to use following the guidelines of Perrin and Armarego. Purification of reaction products was carried out by flash chromatography on Biotage Isolera 4 systems with Ultra-grade silica cartridges. Analytical thin layer chromatography was performed on EM Reagent 0.25 mm silica gel 60-F plates. Visualization was accomplished with UV light. Infrared spectra were recorded on a Bruker Tensor 37 FT-IR spectrometer. 1H NMR spectra were recorded on an AVANCE III 500 MHz spectrometer with direct cryoprobe (500 MHz) and Bruker Avance III 600 MHz (151 MHz) system. Spectra are reported in ppm using solvent as an internal standard (CDCl3 at 7.26 ppm). Peak multiplicities are reported as (s=singlet, d=doublet, t=triplet, q=quartet, quint=quintet, m=multiplet, br=broad; coupling constant(s) in Hz; integration.)

Proton-decoupled 13C NMR spectra were recorded on an AVANCE III 500 MHz with direct cryoprobe (125 MHz) spectrometer and Bruker Avance III 600 MHz (151 MHz) system. These are reported in ppm using solvent as an internal standard (CDCl3 at 77.16 ppm). Low-resolution mass spectra were obtained on WATERS Acquity-H UPLC-MS with a single quad detector (ESI) Varian1200 Quadrupole Mass Spectrometer. High-resolution mass spectra were obtained using an Agilent 6120A LC-time of flight mass spectrometer. Gas chromatography experiments were run on Agilent 7890A/5975C GC/MS System. Enantioselectivity measurements were made on an Agilent 1290 Infinity SFC, using a Chiralpak ID-3 column. Blue light was generated by 3 40 W Kessil H150 LED lights.

Iridium and Ruthenium photocatalysts were obtained from Strem Chemical and Sigma-Aldrich respectively and used as received. Photocatalysts DPAIPN and CZIPN were synthesized.

Preparations of Salicylaldehyde Derive Arylidene Malonates

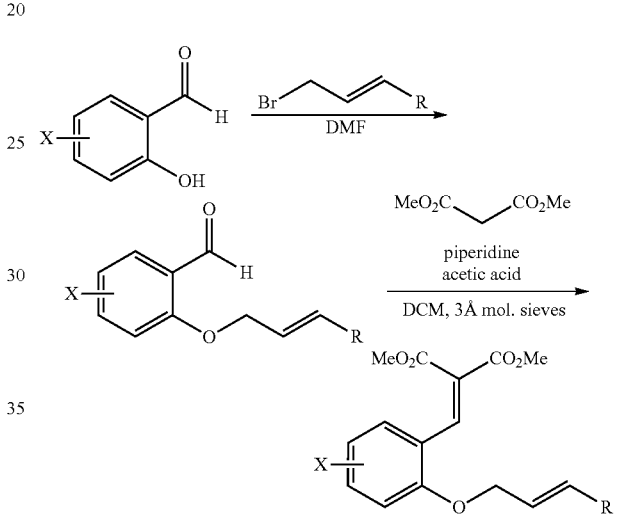

To an oven-dried scintillation vial under nitrogen was added NaH (60 wt %, 1.2 equiv) and DMF (0.5 M), and the mixture was cooled to 0° C. A solution of salicylaldehyde (1 equiv) dissolved in DMF (1.0 M) was slowly added, and upon addition completion, the mixture was allowed to stir at 0° C. for 30 minutes. A solution of allyl bromide electrophile (1.2 equiv) dissolved in DMF (1.0 M) was slowly added, and then reaction mixture was allowed to stir overnight as it warmed to room temperature. Upon reaction completion, sat. aq. NH4Cl was added, and the aqueous layer was extracted 3× with EtOAc. The combined organic layers were washed with H2O and sat. aq. NaCl, passed through a Biotage Isolute phase separator, and concentrated to dryness under reduced pressure on a rotary evaporator to obtain the crude SN2 product, which was directly used in the next reaction without purification.

To a scintillation vial was added the crude aldehyde from the previous step (1 equiv). Malonate or ketoester was added (1.1 equiv), along with 250 wt % activated 4 Å molecular sieves (powder). A magnetic stir bar and CH2Cl2 (2.0 M) were added, followed by acetic acid (0.1 equiv) and piperidine (0.1 equiv). The mixture was stirred overnight. Silica was added and the reaction mixture was concentrated under reduced pressure. The resulting mixture was loaded onto a column of silica and purified via flash column chromatography (10-20% EtOAc/hexanes) to yield the desired product.

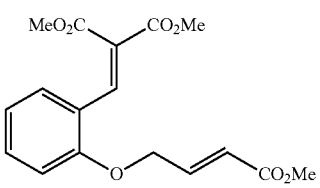

Prepared according to the general procedure with 78% overall yield over two steps. Analytical Data: 1H NMR (500 MHz, Chloroform-d) δ 8.11 (s, 1H), 7.60 (dd, J=8.0, 1.4 Hz, 1H), 7.46-7.39 (m, 1H), 7.26-7.17 (m, 2H), 6.42 (dt, J=15.7, 1.7 Hz, 1H), 4.78 (dd, J=4.7, 1.9 Hz, 2H), 4.02 (s, 2H), 3.93 (d, J=2.2 Hz, 6H). 13C NMR (126 MHz, CDCl3) δ 166.37, 166.18, 163.96, 153.30, 141.67, 137.89, 132.45, 129.36, 128.57, 128.28, 127.43, 125.42, 122.34, 77.31, 77.26, 77.06, 76.80, 72.58, 52.80, 52.63, 51.70. LRMS (ESI): Mass calcd for C17H18O7 [M+H]+: 335.1; found 335.2 HRMS (ESI): Mass calcd for C17H18O7 [M+H]+: 335.1053; found 335.1051 FTIR (neat): 2970, 2732, 1790, 1675, 1656, 1618, 1531, 1466, 1271, 1261, 1200, 1186, 1152, 1045, 1011, 937, 852, 808.

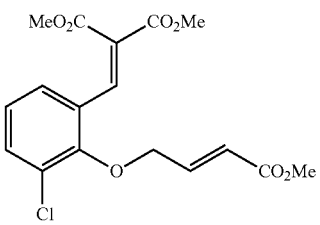 [SMILES: COC(=O)/C=C/COc1c(Cl)cccc1C=C(C(=O)OC)C(=O)OC]

Prepared according to the general procedure with 72% overall yield over two steps. Analytical Data: 1H NMR (500 MHz, Chloroform-d) δ 8.11 (s, 1H), 7.60 (dd, J=8.0, 1.4 Hz, 1H), 7.46-7.39 (m, 1H), 7.26-7.17 (m, 2H), 6.42 (dt, J=15.7, 1.7 Hz, 1H), 4.78 (dd, J=4.7, 1.9 Hz, 2H), 4.02 (s, 2H), 3.93 (d, J=2.2 Hz, 6H). 13C NMR (126 MHz, CDCl3) δ 166.37, 166.18, 163.96, 153.30, 141.67, 137.89, 132.45, 129.36, 128.57, 128.28, 127.43, 125.42, 122.34, 77.31, 77.26, 77.06, 76.80, 72.58, 52.80, 52.63, 51.70. LRMS (ESI): Mass calcd for C17H17ClO7 [M+H]+: 369.1; found 369.1 HRMS (ESI): Mass calcd for C17H17ClO7 [M+H]+: 369.0663; found 369.0660 FTIR (neat): 2988, 2738, 1762, 1685, 1637, 1600, 1518, 1315, 1292, 1246, 1209, 1179, 1158, 1075, 1017, 975, 914, 736.

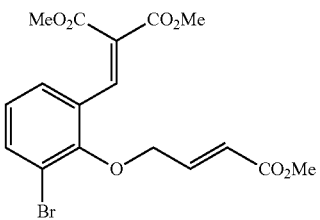 [SMILES: COC(=O)/C=C/COc1c(Br)cccc1C=C(C(=O)OC)C(=O)OC]

Prepared according to the general procedure with 71% overall yield over two steps. Analytical Data: 1H NMR (500 MHz, Chloroform-d) δ 7.93 (s, 1H), 7.62-7.56 (m, 1H), 7.27 (d, J=7.7 Hz, 1H), 7.08-6.96 (m, 2H), 6.25 (d, J=15.4 Hz, 1H), 4.60-4.54 (m, 2H), 3.83 (s, 3H), 3.75 (d, J=5.3 Hz, 6H). 13C NMR (126 MHz, CDCl3) δ 166.42, 166.15, 163.94, 154.32, 141.62, 138.08, 135.50, 129.40, 128.36, 128.23, 125.94, 122.37, 117.98, 77.27, 77.22, 77.02, 76.76, 72.66, 52.83, 52.66, 51.73. LRMS (ESI): Mass calcd for C17H17BrO7 [M+H]+: 413.0; found 413.1 HRMS (ESI): Mass calcd for C17H17BrO7 [M+H]+: 413.0158; found 413.0160 FTIR (neat): 2984, 2784, 2345, 1676, 1659, 1628, 1552, 1481, 1280, 1248, 1214, 1166, 1129, 1044, 1008, 961, 884, 708.

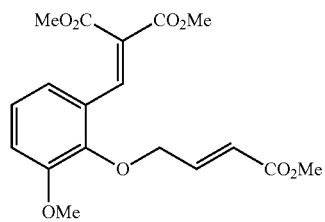 [SMILES: COC(=O)/C=C/COc1c(C=C(C(=O)OC)C(=O)OC)cccc1OC]

Prepared according to the general procedure with 67% overall yield over two steps. Analytical Data: 1H NMR (500 MHz, Chloroform-d) δ 8.24 (s, 1H), 7.29-7.20 (m, 2H), 7.19-7.09 (m, 2H), 6.41 (dd, J=15.8, 2.2 Hz, 1H), 4.86 (dd, J=4.9, 1.9 Hz, 2H), 4.10-4.02 (m, 6H), 3.98-3.93 (m, 6H). 13C NMR (126 MHz, CDCl3) δ 194.33, 166.75, 166.57, 164.33, 152.57, 146.51, 143.04, 138.59, 138.43, 127.73, 126.95, 124.58, 121.66, 120.23, 114.56, 109.82, 100.99, 77.36, 77.10, 76.85, 72.00, 55.89, 55.82, 52.63, 52.52, 51.62. LRMS (ESI): Mass calcd for C18H20O8[M+H]+: 365.1; found 365.2 HRMS (ESI): Mass calcd for C18H20O8 [M+H]+: 365.1158; found 365.1160 FTIR (neat): 2984, 2444, 2241, 1683, 1641, 1625, 1511, 1467, 1276, 1253, 1210, 1167, 1163, 1102, 1016, 961, 878, 701.

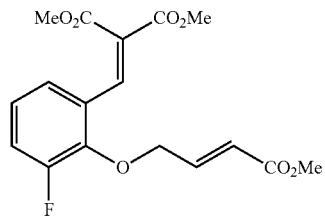 [SMILES: COC(=O)/C=C/COc1c(F)cccc1C=C(C(=O)OC)C(=O)OC]

Prepared according to the general procedure with 73% overall yield over two steps. Analytical Data: 1H NMR (500 MHz, Chloroform-d) δ 8.12 (s, 1H), 7.31-7.22 (m, 2H), 7.22-7.11 (m, 2H), 6.33 (dt, J=15.7, 1.9 Hz, 1H), 4.90 (dd, J=4.8, 1.8 Hz, 2H), 3.98 (s, 2H), 3.89 (d, J=6.2 Hz, 5H). 13C NMR (126 MHz, CDCl3) δ 166.37, 166.29, 164.09, 155.97, 154.00, 144.79, 144.70, 142.00, 137.42, 137.39, 128.51, 128.49, 127.74, 124.22, 124.15, 124.12, 124.09, 122.19, 119.05, 118.89, 77.34, 77.08, 76.83, 72.53, 72.49, 52.74, 52.58, 51.69. LRMS (ESI): Mass calcd for C17H17FO7 [M+H]+: 353.1; found 353.1 HRMS (ESI): Mass calcd for C17H17FO7 [M+H]+: 353.0959; found 353.0961 FTIR (neat): 2999, 2398, 2107, 1706, 1657, 1605, 1586, 1379, 1303, 1259, 1195, 1187, 1133, 1089, 997, 967, 883, 707.

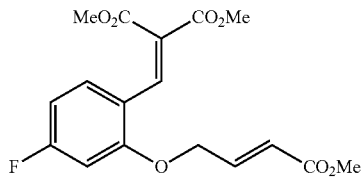

Prepared according to the general procedure with 61% overall yield over two steps. Analytical Data: 1H NMR (500 MHz, Chloroform-d) δ 7.93 (s, 1H), 7.24 (dd, J=8.6, 6.6 Hz, 1H), 6.94 (dt, J=15.8, 4.2 Hz, 1H), 6.56 (td, J=8.3, 2.1 Hz, 1H), 6.47 (dd, J=10.4, 2.3 Hz, 1H), 6.07-6.00 (m, 1H), 4.64 (dd, J=4.0, 2.0 Hz, 2H), 3.74 (t, J=1.1 Hz, 3H), 3.70-3.63 (m, 6H). 13C NMR (126 MHz, CDCl3) δ 166.96, 166.08, 165.92, 164.47, 163.91, 157.83, 157.75, 141.10, 137.26, 130.43, 130.35, 125.57, 122.31, 118.71, 118.68, 108.41, 108.24, 100.58, 100.37, 77.36, 77.11, 76.85, 67.23, 52.60, 52.53, 51.77. LRMS (ESI): Mass calcd for C17H17FO7 [M+H]+: 353.1; found 353.1 HRMS (ESI): Mass calcd for C17H17FO7 [M+H]+: 353.0959; found 353.0960 FTIR (neat): 2993, 2942, 1766, 1690, 1655, 1616, 1562, 1445, 1298, 1249, 1191, 1186, 1151, 1042, 1000, 961, 922, 807.

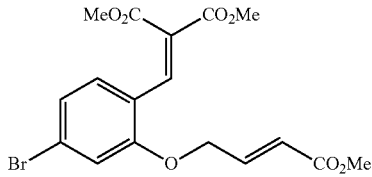 [SMILES: COC(=O)/C=C/COc1cc(Br)ccc1C=C(C(=O)OC)C(=O)OC]

Prepared according to the general procedure with 75% overall yield over two steps. Analytical Data: 1H NMR (500 MHz, Chloroform-d) δ 8.26 (s, 1H), 7.46 (d, J=8.2 Hz, 1H), 7.37-7.32 (m, 1H), 7.35-7.26 (m, 1H), 7.24 (d, J=1.8 Hz, 1H), 6.39 (dt, J=15.8, 2.0 Hz, 1H), 5.00 (dd, J=4.2, 2.1 Hz, 2H), 4.10 (s, 3H), 4.02 (d, J=7.2 Hz, 6H). 13C NMR (126 MHz, CDCl3) δ 165.75, 165.11, 163.33, 155.70, 140.08, 136.32, 128.98, 125.39, 124.70, 123.60, 121.29, 120.63, 114.67, 76.32, 76.26, 76.06, 75.81, 66.24, 51.68, 51.60, 50.80. LRMS (ESI): Mass calcd for C17H17BrO7 [M+H]+: 413.0; found 413.1 HRMS (ESI): Mass calcd for C17H17BrO7 [M+H]+: 413.0158; found 413.0156 FTIR (neat): 2969, 2582, 1919, 1688, 1652, 1615, 1491, 1320, 1271, 1256, 1215, 1165, 1129, 1077, 1001, 933, 891, 813.

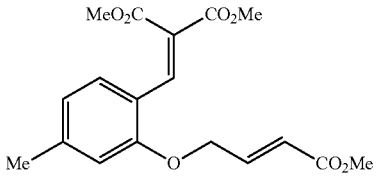

Prepared and had the following analytical data 1H NMR (500 MHz, Chloroform-d) δ=8.14 (s, 1H), 7.25 (d, J=7.9, 1H), 7.09 (dt, J=15.8, 4.1, 1H), 6.77 (d, J=7.9, 1H), 6.66 (s, 1H), 6.17 (dt, J=15.8, 2.0, 1H), 4.75 (dd, J=4.1, 2.0, 2H), 3.85 (s, 2H), 3.78 (d, J=16.8, 5H), 2.34 (s, 3H). 13C NMR (126 MHz, CDCl3) δ 167.33, 166.33, 164.73, 156.46, 143.16, 142.08, 138.31, 128.84, 124.67, 122.21, 121.85, 119.68, 112.90, 112.66, 77.37, 77.11, 76.86, 66.89, 52.51, 52.47, 51.72, 21.91. LRMS (ESI): Mass calcd for C18H20O7 [M+H]+: 349.1; found 349.1 HRMS (ESI): Mass calcd for C18H20O7 [M+H]+: 349.1209; found 349.1208 FTIR (neat): 3000, 2616, 2232, 1664, 1633, 1611, 1552, 1442, 1275, 1227, 1212, 1165, 1126, 1022, 1012, 925, 905, 803

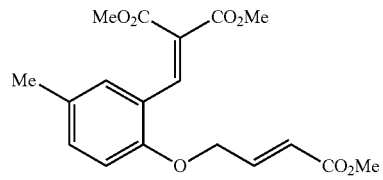 [SMILES: COC(=O)/C=C/COc1ccc(C)cc1C=C(C(=O)OC)C(=O)OC]

Prepared and had the following analytical data 1H NMR (500 MHz, Chloroform-d) δ=8.22 (s, 1H), 7.26-7.21 (m, 2H), 7.17 (dt, J=15.8, 4.1, 1H), 6.84 (d, J=8.9, 1H), 6.25 (dt, J=15.8, 2.1, 1H), 4.82 (dd, J=4.2, 2.0, 2H), 3.95 (s, 3H), 3.87 (d, J=18.6, 5H), 2.35 (s, 3H). 13C NMR (126 MHz, CDCl3) δ 167.33, 166.33, 164.73, 156.46, 143.16, 142.08, 138.31, 128.84, 124.67, 122.21, 121.85, 119.68, 112.90, 112.66, 77.37, 77.11, 76.86, 66.89, 52.51, 52.47, 51.72, 21.91. LRMS (ESI): Mass calcd for C18H20O7 [M+H]+: 349.1; found 349.1 HRMS (ESI): Mass calcd for C18H20O7 [M+H]+: 349.1209; found 349.1210 FTIR (neat): 2967, 2772, 1975, 1678, 1650, 1612, 1571, 1435, 1283, 1231, 1192, 1188, 1143, 1070, 992, 943, 897, 792.

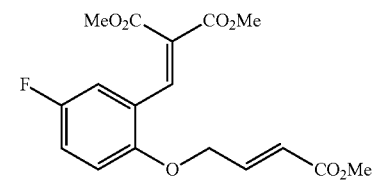 [SMILES: COC(=O)/C=C/COc1ccc(F)cc1C=C(C(=O)OC)C(=O)OC]

Prepared and had the following analytical data 1H NMR (500 MHz, Chloroform-d) δ=8.22 (s, 1H), 7.23 (dt, J=26.7, 4.3, 2H), 7.00-6.92 (m, 1H), 6.31 (dt, J=15.9, 2.3, 1H), 4.93-4.87 (m, 2H), 4.00 (dd, J=21.7, 2.7, 5H), 3.93 (s, 2H), 3.92 (d, J=5.6, 1H). 13C NMR (126 MHz, CDCl3) δ 166.53, 166.21, 164.25, 157.85, 155.94, 152.66, 141.70, 137.02, 126.99, 123.76, 123.69, 122.13, 118.31, 118.13, 115.56, 115.36, 113.40, 113.34, 77.32, 77.06, 76.81, 67.67, 52.73, 52.66, 51.78. LRMS (ESI): Mass calcd for C17H17FO7 [M+H]+: 353.1; found 353.1 HRMS (ESI): Mass calcd for C17H17FO7 [M+H]+: 353.0959; found 353.0961 FTIR (neat): 2992, 2745, 2037, 1696, 1634, 1608, 1500, 1439, 1278, 1224, 1205, 1175, 1162, 1027, 998, 962, 920, 815.

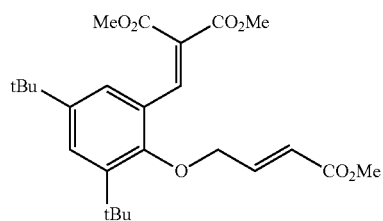 [SMILES: COC(=O)/C=C/COc1c(C=C(C(=O)OC)C(=O)OC)cc(C(C)(C)C)cc1C(C)(C)C]

Prepared and had the following analytical data 1H NMR (500 MHz, Chloroform-d) δ=7.78 (s, 1H), 7.24 (d, J=2.5, 1H), 7.06 (d, J=2.3, 1H), 6.89 (dt, J=15.7, 3.9, 1H), 6.15 (dd, J=15.7, 2.2, 1H), 4.34 (dd, J=3.9, 2.2, 2H), 3.69-3.54 (m, 9H), 1.12 (s, 9H). 13C NMR (126 MHz, CDCl3) δ 166.77, 166.64, 164.34, 154.88, 146.45, 142.81, 142.21, 141.06, 126.98, 126.85, 126.28, 124.38, 121.20, 77.28, 77.23, 77.03, 76.77, 73.55, 52.62, 52.58, 51.69, 35.26, 34.65, 31.38, 30.74. LRMS (ESI): Mass calcd for C25H34O7 [M+H]+: 447.2; found 447.1 HRMS (ESI): Mass calcd for C25H34O7

[M+H]+: 447.2305; found 447.2307 FTIR (neat): 2978, 2578, 2191, 1689, 1632, 1606, 1592, 1310, 1291, 1267, 1207, 1185, 1138, 1066, 1002, 967, 851, 786.

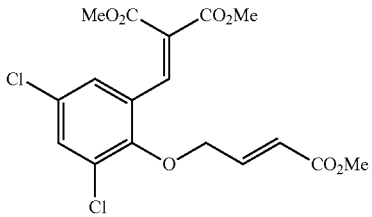 [SMILES: COC(=O)/C=C/COc1c(Cl)cc(Cl)cc1C=C(C(=O)OC)C(=O)OC]

Prepared and ad the following analytical data 1H NMR (500 MHz, Chloroform-d) δ=7.65 (s, 1H), 7.24 (d, J=2.4, 1H), 7.03 (d, J=2.4, 1H), 6.83 (dt, J=15.8, 4.7, 1H), 6.03 (dt, J=15.7, 1.9, 1H), 4.40 (dd, J=4.8, 1.8, 2H), 3.67 (d, J=1.0, 3H), 3.59 (dd, J=16.2, 1.1, 6H). 13C NMR (126 MHz, CDCl3) δ 166.20, 165.61, 163.61, 151.93, 141.19, 136.47, 131.80, 130.27, 130.21, 129.38, 129.36, 127.27, 122.60, 77.34, 77.29, 77.09, 76.83, 72.72, 52.90, 52.71, 51.71. LRMS (ESI): Mass calcd for C17H16Cl2O7 [M+H]+: 403.1; found 403.1 HRMS (ESI): Mass calcd for C17H16Cl2O7 [M+H]+: 403.0273; found 403.0271 FTIR (neat): 2967, 2537, 1842, 1708, 1654, 1614, 1538, 1391, 1306, 1262, 1206, 1188, 1131, 1120, 993, 935, 902, 748.

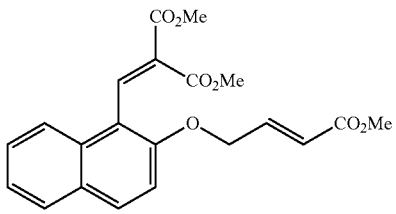 [SMILES: COC(=O)/C=C/COc1ccc2ccccc2c1C=C(C(=O)OC)C(=O)OC]

Prepared according to the general procedure with 78% overall yield over two steps. Analytical Data: 1H NMR (500 MHz, Chloroform-d) δ=8.37 (s, 1H), 7.95-7.85 (m, 2H), 7.63-7.55 (m, 1H), 7.52-7.44 (m, 1H), 7.26-7.12 (m, 1H), 6.22 (dt, J=15.8, 2.1, 1H), 4.92 (dd, J=4.3, 2.0, 1H), 4.01 (s, 2H), 3.83 (s, 2H), 3.58 (s, 2H). 13C NMR (126 MHz, CDCl3) δ 166.33, 165.64, 164.90, 152.96, 142.37, 140.50, 131.94, 131.64, 129.86, 129.01, 128.42, 127.48, 124.49, 123.77, 122.12, 117.40, 113.85, 77.32, 77.07, 76.82, 68.00, 52.69, 52.00, 51.74. LRMS (ESI): Mass calcd for C21H20O7 [M+H]+: 385.1; found 385.1 HRMS (ESI): Mass calcd for C21H20O7 [M+H]+: 385.1209; found 385.1210 FTIR (neat): 2996, 2543, 2196, 1677, 1641, 1622, 1543, 1441, 1306, 1266, 1192, 1163, 1148, 1046, 990, 930, 831, 792

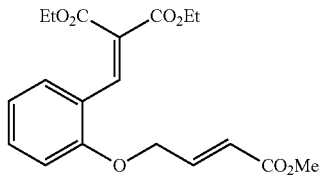

Prepared according to the general procedure with 85% overall yield over two steps. Analytical Data: 1H NMR (500 MHz, Chloroform-d) δ=7.96 (s, 1H), 7.25 (dd, J=7.9, 1.6, 1H), 7.19-7.12 (m, 1H), 6.91 (dt, J=15.8, 3.9, 1H), 6.77 (t, J=7.5, 1H), 6.68 (d, J=8.3, 1H), 6.01 (dt, J=15.8, 2.1, 1H), 4.57 (dd, J=4.1, 2.1, 2H), 4.12 (dq, J=14.1, 7.1, 4H), 3.56 (s, 3H), 1.18 (t, J=7.1, 3H), 1.07 (t, J=7.1, 3H). 13C NMR (126 MHz, CDCl3) δ 166.45, 166.14, 164.05, 156.24, 142.03, 137.33, 131.92, 129.02, 126.55, 122.49, 121.58, 121.11, 111.96, 77.54, 77.28, 77.03, 66.72, 61.43, 61.39, 51.53, 14.01, 13.79. LRMS (ESI): Mass calcd for C19H22O7 [M+H]+: 363.1; found 363.2 HRMS (ESI): Mass calcd for C19H22O7 [M+H]+: 363.1365; found 363.1363 FTIR (neat): 2991, 2700, 2301, 1699, 1655, 1602, 1512, 1400, 1296, 1250, 1200, 1181, 1131, 1043, 1002, 965, 840, 802

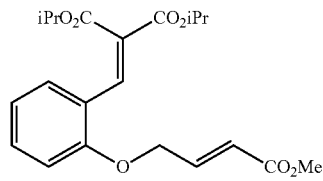

Prepared according to the general procedure with 75% overall yield over two steps. Analytical Data: 1H NMR (500 MHz, Chloroform-d) δ=7.86 (s, 1H), 7.23 (dd, J=7.8, 1.5, 1H), 7.15-7.04 (m, 1H), 6.86 (dt, J=15.8, 3.9, 1H), 6.71 (t, J=7.6, 1H), 6.61 (d, J=8.3, 1H), 5.97 (dd, J=15.8, 2.0, 1H), 5.02-4.88 (m, 2H), 4.53 (dd, J=4.1, 2.1, 2H), 3.56-3.42 (m, 4H), 1.10 (d, J=6.3, 5H), 1.02 (d, J=6.1, 5H). 13C NMR (126 MHz, CDCl3) δ 166.34, 166.17, 166.08, 163.70, 156.28, 142.05, 136.62, 131.75, 129.20, 128.24, 127.42, 127.03, 122.77, 121.71, 121.14, 111.89, 77.34, 77.09, 76.84, 69.11, 69.06, 66.78, 51.66, 46.19, 42.25, 21.74, 21.49. LRMS (ESI): Mass calcd for C21H26O7 [M+H]+: 390.2; found 390.2 HRMS (ESI): Mass calcd for C21H26O7 [M+H]+: 390.1679; found 390.1680 FTIR (neat): 2998, 2486, 1967, 1703, 1639, 1614, 1546, 1385, 1280, 1237, 1203, 1179, 1124, 1030, 994, 930, 846, 705.

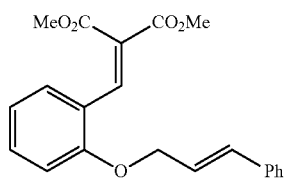 [SMILES: COC(=O)C(=Cc1ccccc1OC/C=C/c1ccccc1)C(=O)OC]

Prepared according to the general procedure with 82% overall yield over two steps. Analytical Data: 1H NMR (500 MHz, Chloroform-d) δ=8.14 (s, 1H), 7.35-7.20 (m, 5H), 7.21-7.13 (m, 1H), 6.89-6.81 (m, 2H), 6.63 (dt, J=16.0, 1.6, 1H), 6.31 (dt, J=16.0, 5.7, 1H), 4.65 (dd, J=5.8, 1.6, 2H), 3.74 (s, 2H), 3.70 (s, 2H), 3.65 (s, 2H), 3.30 (s, 1H). 13C NMR (126 MHz, CDCl3) δ 167.23, 166.92, 164.73, 157.21, 139.00, 136.27, 133.14, 132.16, 129.01, 128.64, 128.02, 126.63, 125.48, 123.92, 122.58, 120.85, 112.48, 77.48, 77.23, 76.97, 69.33, 69.21, 54.48, 52.54, 52.51, 52.47, 41.09. LRMS (ESI): Mass calcd for C21H20O5[M+H]+: 353.1; found 353.2 HRMS (ESI): Mass calcd for C21H20O5 [M+H]+: 353.1311; found 353.1310 FTIR (neat): 2990, 2600, 2211, 1666, 1636, 1606, 1515, 1453, 1293, 1251, 1220, 1172, 1143, 1103, 993, 956, 831, 741

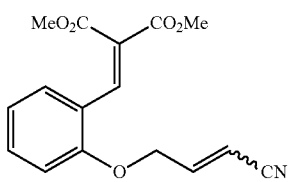 [SMILES: COC(=O)C(=Cc1ccccc1OCC=CC#N)C(=O)OC]

Prepared according to the general procedure with 55% overall yield over two steps. Isolated as an inseparable 1:1 mixture of Z/E isomers (4-bromobut-2-enenitrile used for SN2 reaction was an inseparable 1:1 mixture of Z/E isomers) Analytical Data: 1H NMR (500 MHz, Chloroform-d) δ=7.96 (d, J=2.7, 1H), 7.56-7.46 (m, 1H), 7.32-7.19 (m, 2H), 7.22-7.11 (m, 1H), 6.90-6.81 (m, 1H), 6.84-6.67 (m, 2H), 5.63 (dt, J=16.4, 2.3, 1H), 5.51-5.44 (m, 1H), 5.17 (s, 1H), 4.88-4.76 (m, 1H), 4.62 (dd, J=3.7, 2.3, 1H), 3.75-3.59 (m, 6H). 13C NMR (126 MHz, CDCl3) δ 167.00, 166.88, 164.62, 164.45, 156.03, 155.79, 149.17, 148.77, 147.88, 138.76, 138.22, 134.48, 132.16, 132.08, 129.56, 129.40, 129.28, 126.39, 126.10, 124.90, 122.81, 121.95, 121.74, 116.85, 116.63, 114.70, 112.06, 111.96, 101.78, 101.24, 77.27, 77.22, 77.02, 76.77, 66.78, 66.46, 52.75, 52.65, 52.57, 52.51, 41.14. LRMS (ESI): Mass calcd for C16H15NO5 [M+H]+: 302.1; found 302.2 HRMS (ESI): Mass calcd for C16H15NO5 [M+H]+: 302.0950; found 302.0951 FTIR (neat): 2975, 2818, 2044, 1670, 1638, 1625, 1592, 1373, 1297, 1270, 1197, 1181 1135, 1114, 1019, 924, 886, 745

Preparation of Salicylaldehyde Derived Arylidene Malonates Requiring Metathesis Reactions

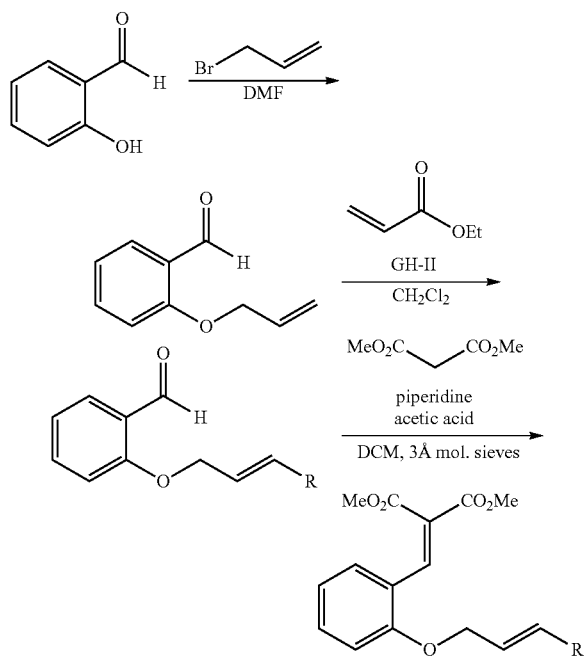

To an oven-dried scintillation vial under nitrogen was added NaH (60 wt %, 1.2 equiv) and DMF (0.5 M), and the mixture was cooled to 0° C. A solution of salicylaldehyde (1 equiv) dissolved in DMF (1.0 M) was slowly added, and upon addition completion, the mixture stirred at 0° C. for 30 minutes. A solution of allyl bromide electrophile (1.2 equiv) dissolved in DMF (1.0 M) was slowly added and then reaction was allowed to stir overnight as it warmed to room temperature. Upon reaction completion, sat. aq. NH4Cl was added, and the aqueous layer was extracted 3× with EtOAc. The combined organic layers were washed with H2O and sat. aq. NaCl, passed through a Biotage Isolute phase separator, and concentrated to dryness under reduced pressure on a rotary evaporator to obtain the crude SN2 product, which was directly used in the next reaction without purification.

A flame dried round bottom flask was charged with alkene starting material (1.0 equiv) in CH2Cl2 (0.5 M), ethyl acrylate (5.0 equiv) and flushed with Ar. Grubbs-Hoveyeda second generation catalyst (2.5 mol %) was added in one portion and the reaction was stirred at room temperature under an atmosphere of Ar. The homogeneous solution was allowed to stir for 6 hours. Once the reaction was complete, the reaction was concentrated to dryness under reduced pressure on a rotary evaporator. The crude product was directly used in the next reaction without purification To a scintillation vial was added the crude aldehyde from the previous step (1 equiv). Malonate or ketoester was added (1.1 equiv), along with 250 wt % activated 4 Å molecular sieves (powder). A magnetic stir bar and CH2Cl2 (2.0 M) were added, followed by acetic acid (0.1 equiv) and piperidine (0.1 equiv). The mixture was stirred overnight. Silica was added, and the reaction concentrated under reduced pressure. The resulting mixture was loaded onto a column of silica and purified via flash column chromatography (10-20% EtOAc/hexanes) to yield the desired product.

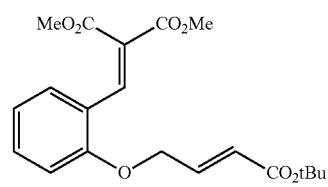 [SMILES: COC(=O)C(=Cc1ccccc1OC/C=C/C(=O)OC(C)(C)C)C(=O)OC]

Prepared according to the general procedure with 65% overall yield over three steps. Analytical Data: 1H NMR (500 MHz, Chloroform-d) δ=8.05 (s, 1H), 7.28-7.15 (m, 3H), 6.90-6.80 (m, 2H), 6.77-6.71 (m, 1H), 5.95 (dt, J=15.7, 2.0, 1H), 4.63 (dd, J=4.3, 2.0, 2H), 3.75 (s, 2H), 3.66 (d, J=18.0, 5H), 1.39 (s, 7H). 13C NMR (126 MHz, CDCl3) δ 167.10, 166.92, 165.17, 164.60, 156.53, 140.46, 138.56, 133.52, 132.09, 130.24, 129.03, 128.69, 128.45, 128.15, 125.76, 124.26, 122.58, 121.25, 112.12, 80.80, 77.33, 77.07, 76.82, 67.11, 60.39, 52.57, 52.54, 52.50, 41.11, 28.09. LRMS (ESI): Mass calcd for C20H24O7[M+H]+: 377.2; found 377.2 HRMS (ESI): Mass calcd for C20H24O7[M+H]+: 377.1522; found 377.1520 FTIR (neat): 2982, 2944, 1952, 1669, 1647, 1607, 1595, 1384, 1276, 1244, 1197, 1180, 1138, 1066, 992, 950, 893, 688.

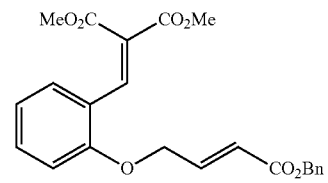

Prepared according to the general procedure with 52% overall yield over three steps. Analytical Data: 1H NMR (500 MHz, Chloroform-d) δ=8.01 (s, 1H), 7.28-7.15 (m, 7H), 6.98 (dt, J=15.7, 4.1, 1H), 6.81 (t, J=7.6, 1H), 6.70 (d, J=8.1, 1H), 6.07 (dt, J=15.8, 2.0, 1H), 5.07 (s, 2H), 4.63 (dd, J=4.2, 2.1, 2H), 3.66 (d, J=23.6, 6H). 13C NMR (126 MHz, CDCl3) δ 167.06, 165.66, 164.57, 156.38, 142.33, 138.48, 135.77, 132.07, 129.10, 128.59, 128.31, 125.89, 122.66, 122.10, 121.39, 112.10, 77.30, 77.24, 77.04, 76.79, 67.01, 66.50, 52.58, 52.52. LRMS (ESI): Mass calcd for C23H22O7[M+H]+: 411.1; found 411.1 HRMS (ESI): Mass calcd for C23H22O7[M+H]+: 411.1365; found 411.1367 FTIR (neat): 2964, 2533, 2087, 1691, 1640, 1607, 1571, 1384, 1297, 1230, 1192, 1186, 1123, 1027, 992, 987, 882, 765.

Preparation of Salicylaldehyde Derived Alkyne Electrophiles

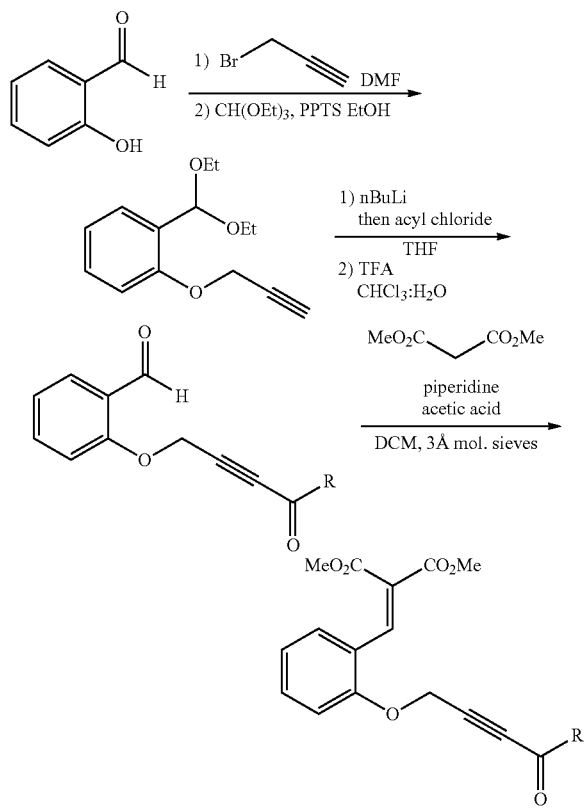

To an oven-dried scintillation vial under nitrogen was added NaH (60 wt %, 1.2 equiv) and DMF (0.5 M), and the mixture was cooled to 0° C. A solution of salicylaldehyde (1 equiv) dissolved in DMF (1.0 M) was slowly added, and upon addition completion, the mixture stirred at 0° C. for 30 minutes. A solution of propargyl bromide (1.2 equiv) dissolved in DMF (1.0 M) was slowly added and then reaction was allowed to stir overnight as it warmed to room temperature. Upon reaction completion, sat. aq. NH4Cl was added, and the aqueous layer was extracted 3× with EtOAc. The combined organic layers were washed with H2O and sat. aq. NaCl, passed through a Biotage Isolute phase separator, and concentrated to dryness under reduced pressure on a rotary evaporator to obtain the crude SN2 product, which was directly used in the next reaction without purification.

In an oven dried round-bottom flask, salicylaldehyde propargyl ether (1 equiv) was dissolved in dry ethanol (0.2 M) under N2 atmosphere. Triethyl orthoformate (1.7 equiv) and PPTS (1 mol %) were added, and the resulting solution was refluxed for 3 h. Upon reaction completion, the reaction mixture was quenched with few drops of Et3N and concentrated to dryness under reduced pressure on a rotary evaporator. The oil was diluted in EtOAc (50 mL), washed with 10% NaHCO3 (2×20 mL), followed by saturated NaCl (2×10 mL) and then dried over Na2SO4. The combined organic layers were concentrated to dryness under reduced pressure on a rotary evaporator. The crude product was directly used in the next reaction without purification.

In an oven dried round-bottom flask, the acetal-protected salicylaldehyde (1.0 equiv) was dissolved in dry THF (0.2 M). The solution was stirred at 78° C., and n-BuLi (1.1 equiv, 2.5 M in hexanes) was slowly added to the flask over 10 min, and the reaction was stirred for another 30 min. At the same temperature, acyl chloride (1.7 equiv) dissolved in THF (0.2 M) was slowly added to the reaction mixture and stirred for an additional 2 h. Upon reaction completion, the reaction mixture was allowed to warm to room temperature and quenched with sat. aq. NH4Cl (20 mL). Then the reaction mixture was diluted with EtOAc (50 mL), washed with water (3×50 mL), followed by saturated NaCl (2×10 mL), and then dried over Na2SO4. The combined organic layers were concentrated to dryness under reduced pressure on a rotary evaporator. The crude product was directly used in the next reaction without purification.

To a scintillation vial with the crude acetal protected alkyne was added CHCl3:H2O (3:1), and the reaction was stirred until the alkyne completely dissolved. Trifluoroacetic acid (5.0 equiv) was added, and the reaction was stirred at room temperature for 3 h. Saturated NaHCO3 was added, and the aqueous layer was extracted with CH2Cl2. The combined organic layers were passed through a Biotage Isolute phase separator and concentrated to dryness under reduced pressure on a rotary evaporator to obtain the crude product, which was directly used in the next reaction without purification.

To a scintillation vial was added the crude aldehyde from the previous step (1 equiv). Malonate or ketoester was added (1.1 equiv), along with 250 wt % activated 4 Å molecular sieves (powder). A magnetic stir bar and CH2Cl2 (2.0 M) were added, followed by acetic acid (0.1 equiv) and piperidine (0.1 equiv). The mixture was stirred overnight. Silica was added and the reaction concentrated under reduced pressure. The resulting mixture was loaded onto a column of silica and purified via flash column chromatography (10-20% EtOAc/hexanes) to yield the desired product.

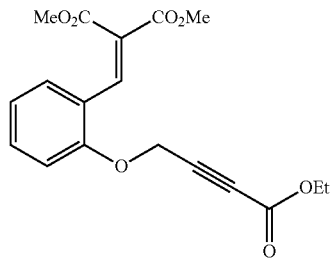 [SMILES: CCOC(=O)C#CCOc1ccccc1C=C(C(=O)OC)C(=O)OC]

Prepared according to the general procedure with 61% overall yield over five steps. Analytical Data: 1H NMR (500 MHz, Chloroform-d) δ=7.95 (d, J=15.6, 1H), 7.24 (pd, J=8.7, 8.3, 3.7, 2H), 6.96-6.84 (m, 1H), 6.88-6.79 (m, 1H), 4.74 (s, 2H), 4.16-3.97 (m, 2H), 3.71 (d, J=4.1, 3H), 3.65 (s, 3H), 1.20-1.08 (m, 3H). 13C NMR (126 MHz, CDCl3) δ 167.00, 164.56, 155.63, 152.77, 138.45, 132.02, 131.88, 129.32, 126.15, 122.99, 122.00, 112.36, 80.88, 79.11, 77.29, 77.04, 76.78, 62.37, 55.83, 52.63, 52.53, 28.61, 13.96. LRMS (ESI): Mass calcd for C18H18O7[M+H]+: 347.1; found 347.1 HRMS (ESI): Mass calcd for C18H18O7[M+H]+: 347.1053; found 347.1051 FTIR (neat): 2980, 2888, 2311, 1668, 1643, 1605, 1566, 1417, 1287, 1269, 1214, 1164, 1130, 1028, 1001, 977, 853, 774.

Preparation of Salicylaldehyde Derived Alkyne-Aryl Arylidene Malonates

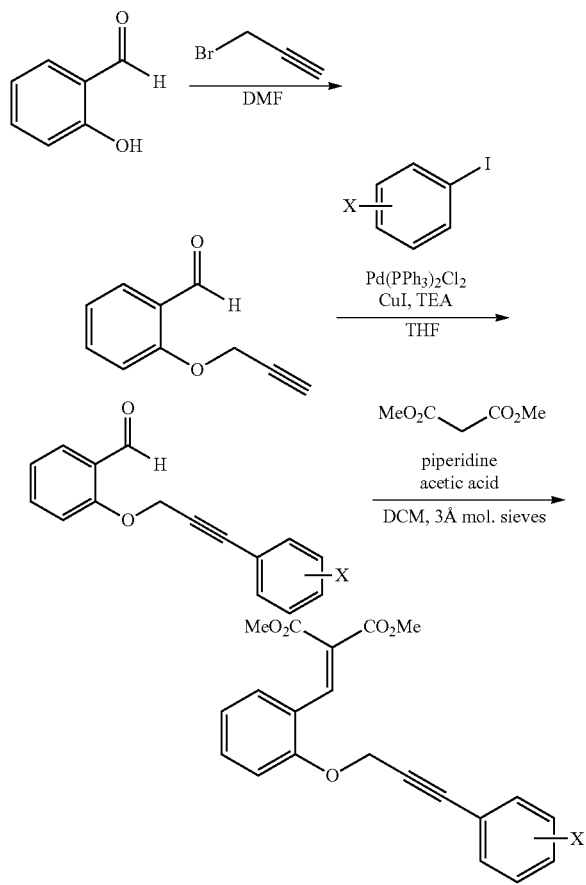

To an oven dried scintillation vial under nitrogen was added NaH (60 wt %, 1.2 equiv) and DMF (0.5 M), and the mixture was cooled to 0° C. A solution of salicylaldehyde (1 equiv) dissolved in DMF (1.0 M) was slowly added, and upon addition completion, the mixture stirred at 0° C. for 30 minutes. A solution of propargyl bromide (1.2 equiv) dissolved in DMF (1.0 M) was slowly added and then reaction was allowed to stir overnight as it warmed to room temperature. Upon reaction completion, sat. aq. NH4Cl was added, and the aqueous layer was extracted 3× with EtOAc. Upon reaction completion, sat. aq. NH4Cl was added, and the aqueous layer was extracted 3× with EtOAc. The combined organic layers were washed with H2O and sat. aq. NaCl, passed through a Biotage Isolute phase separator, and concentrated to dryness under reduced pressure on a rotary evaporator to obtain the crude SN2 product, which was directly used in the next reaction without purification.

To a scintillation vial was added the crude 2-prop-2-ynyloxy-benzaldehyde derivatives (1.0 equiv) with substituted iodobenzene (1.2 equiv), Pd(PPh3)2Cl2 (2 mol %), CuI (4 mol %) and triethylamine (1.5 equiv) in dry THF (0.2 M). The reaction was stirred for 18 hours until reaction completion NH4Cl was added, and the aqueous layer was extracted 3× with EtOAc. The combined organic layers were washed with H2O and sat. aq. NaCl, passed through a Biotage Isolute phase separator, and concentrated to dryness under reduced pressure on a rotary evaporator to obtain the crude product, which was directly used in the next reaction without purification.

To a scintillation vial was added the crude aldehyde from the previous step (1 equiv). Malonate or ketoester was added (1.1 equiv) as well as 250 wt % activated 4 Å molecular sieves (powder). A magnetic stirbar and CH2Cl2 (2.0 M) were added, followed by acetic acid (0.1 equiv) and piperidine (0.1 equiv). The mixture was stirred overnight. Silica was added and the reaction concentrated under reduced pressure. The resulting mixture was loaded onto a column of silica and purified via flash column chromatography (10-20% EtOAc/hexanes) to yield the desired product.

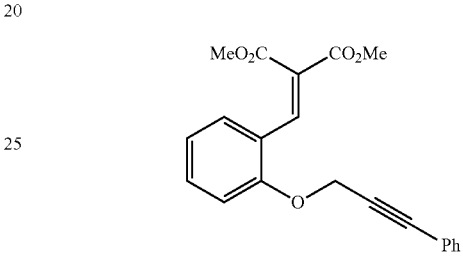

Prepared according to the general procedure with 70% overall yield over three steps. Analytical Data: 1H NMR (500 MHz, Chloroform-d) δ 8.08 (s, 1H), 7.39-7.26 (m, 4H), 7.29-7.17 (m, 3H), 7.08 (dd, J=8.4, 1.0 Hz, 1H), 6.90 (td, J=7.6, 1.0 Hz, 1H), 4.90 (s, 2H), 3.77 (s, 3H), 3.70 (d, J=19.1 Hz, 6H), 3.32 (s, 1H). 13C NMR (126 MHz, CDCl3) δ 167.17, 166.93, 164.71, 156.31, 138.94, 131.97, 131.79, 131.55, 129.17, 128.80, 128.32, 125.69, 122.89, 122.07, 121.40, 112.84, 87.74, 83.38, 77.31, 77.27, 77.06, 76.81, 57.10, 52.57, 52.56, 52.50, 41.13. LRMS (ESI): Mass calcd for C21H18O5[M+H]+: 351.1; found 351.1 HRMS (ESI): Mass calcd for C21H18O5 [M+H]+: 351.1154; found 351.1153 FTIR (neat): 2972, 2382, 2316, 1708, 1637, 1599, 1489, 1355, 1277, 1234, 1212, 1182, 1134, 1060, 1008, 976, 900, 798

Preparation of Tetrahydroquinoline-Precursor Arylidene Malonate

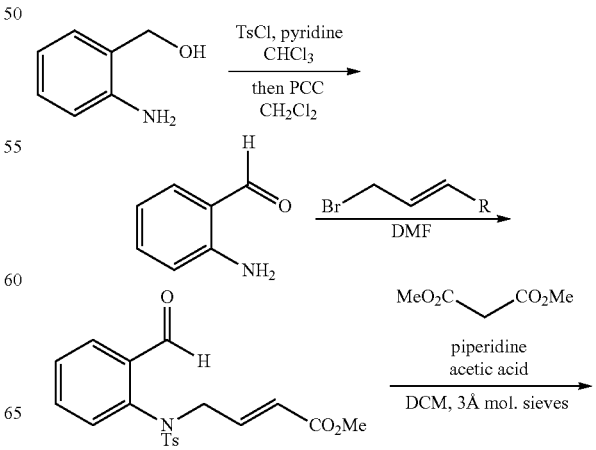

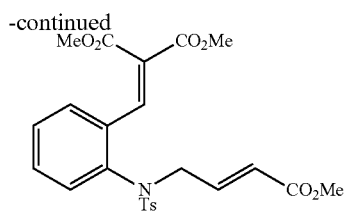

To a dry and N2-flushed round bottom flask, equipped with a magnetic stirring bar and a septum, was charged with a solution of 2-aminobenzyl alcohol (1.0 equiv) in CHCl3 (0.2 M). TsCl (1.1 equiv) and pyridine (5 mol %) were added, and the reaction mixture was stirred for 12 h at room temperature. Once the reaction was complete, the reaction was concentrated to dryness under reduced pressure on a rotary evaporator. Without purification, the crude product was dissolved in CH2Cl2 (0.5 M) and PCC (1.2 equiv) was added. The reaction mixture was stirred for 4 h at room temperature and then filtered through celite followed by washing with CH2Cl2. The combined organic layers were concentrated to dryness under reduced pressure on a rotary evaporator. The crude product was directly used in the next reaction without purification.

To an oven dried scintillation vial under nitrogen was added NaH (60 wt %, 1.2 equiv) and DMF (0.5 M), and the mixture was cooled to 0° C. A solution of N-tosyl-aldehyde (1 equiv) dissolved in DMF (1.0 M) was slowly added, and upon addition completion, the mixture stirred at 0° C. for 30 minutes. A solution of allyl bromide (1.2 equiv) dissolved in DMF (1.0 M) was slowly added and then reaction was allowed to stir overnight as it warmed to room temperature. Upon reaction completion, sat. aq. NH4Cl was added, and the aqueous layer was extracted 3× with EtOAc. The combined organic layers were washed with H2O and saturated NaCl followed by passage through a Biotage Isolute phase separator and concentration concentrated to dryness under reduced pressure on a rotary evaporator to obtain the crude SN2 product, which was directly used in the next reaction without purification.

To a scintillation vial was added the crude aldehyde from the previous step (1 equiv). Malonate or ketoester was added (1.1 equiv), as well as 250 wt % activated 4 Å molecular sieves (powder). A magnetic stirbar and mL of CH2Cl2 (2.0 M) were added, followed by acetic acid (0.1 equiv) and piperidine (0.1 equiv). The mixture was stirred overnight. Silica was added and the reaction concentrated under reduced pressure. The resulting mixture was loaded onto a column of silica and purified via flash column chromatography (10-20% EtOAc/hexanes) to yield the desired product.

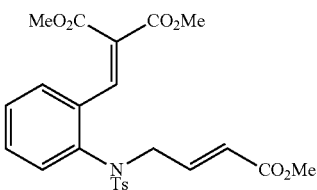 [SMILES: COC(=O)/C=C/CN(c1ccccc1C=C(C(=O)OC)C(=O)OC)S(=O)(=O)c1ccc(C)cc1]

Prepared according to the general procedure with 62% overall yield over four steps. Analytical Data: 1H NMR (500 MHz, Chloroform-d) δ=7.64 (s, 1H), 7.57-7.48 (m, 2H), 7.32-7.20 (m, 4H), 7.02-6.93 (m, 1H), 6.72 (dt, J=15.7, 6.6, 1H), 5.73 (dt, J=15.7, 1.5, 1H), 5.24 (s, 1H), 4.20 (dd, J=6.6, 1.4, 2H), 3.78 (s, 3H), 3.69 (s, 1H), 3.61 (d, J=3.8, 5H), 2.38 (s, 2H). 13C NMR (126 MHz, CDCl3) δ 166.20, 165.81, 163.72, 147.09, 144.24, 141.33, 140.13, 138.13, 135.79, 134.37, 130.89, 130.51, 129.83, 129.10, 129.00, 128.30, 127.76, 124.60, 119.73, 77.29, 77.04, 76.78, 61.84, 53.44, 52.90, 52.67, 52.52, 51.65, 51.61, 21.62. LRMS (ESI): Mass calcd for C24H25NO8S [M+H]+: 487.1; found 487.2 HRMS (ESI): Mass calcd for C24H25NO8S [M+H]+: 487.1309; found 487.1311 FTIR (neat): 2977, 2957, 2293, 1671, 1644, 1602, 1488, 1342, 1295, 1265, 1195, 1172, 1143, 1067, 1012, 956, 845, 764

Preparation of Tetrahydronapthalene-Precursor Arylidene Malonate

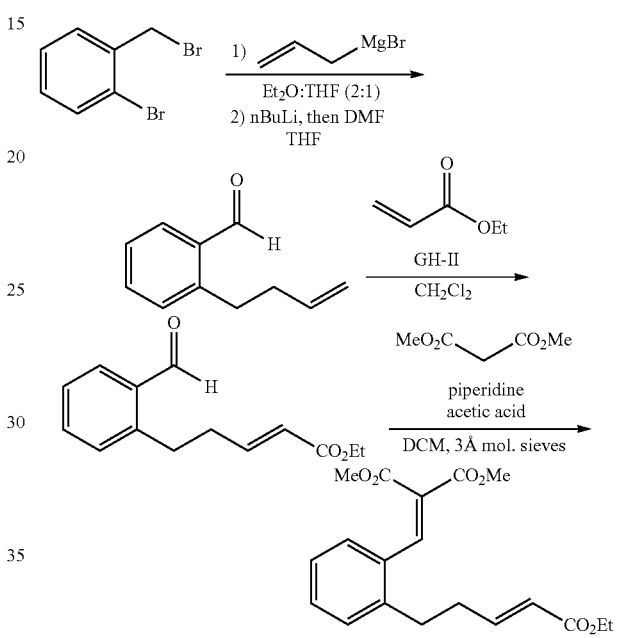

To a round-bottom flask flushed with N2 was charged Mg turnings (5.0 equiv) and anhydrous ether (0.5 M). A tip of iodine and a drop of 1,2-dibromoethane were successively added. After leaving the mixture at 0° C. for 30 min, a solution of allyl bromide (2.0 equiv) in dry ether (0.5M) was added dropwise to the mixture to prepare a solution of a Grignard reagent. To a solution of 2-bromobenzyl bromide (1.0 equiv) in anhydrous THF (0.5 M) was added dropwise the prepared solution of a Grignard reagent at rt, and the reaction mixture was stirred at rt overnight. The following day, 25 mL of H2O was added to the mixture, which was then extracted with ether (15 mL×3). The combined ethereal solution was washed with H2O (15 mL×3) and dried over anhydrous MgSO4. The reaction was concentrated to dryness under reduced pressure on a rotary evaporator. The crude product was directly used in the next reaction without purification.

Under N2, to a solution of 1-bromo or iodo aryl compound 1.0 equiv) in anhydrous diethyl ether (0.25 M) at −78° C. was slowly added n-BuLi (1.1 equiv, 2.5 M in hexanes). The reaction was stirred at the same temperature for 40 min, and DMF (3.0 equiv) was added dropwise. The reaction was allowed to warm to room temperature over 1 h before it was quenched with saturated aqueous NH4Cl. The reaction mixture was diluted with diethyl ether (30 mL), washed with saturated NH4Cl (10 mL) and saturated NaCl (10 mL), dried over Na2SO4, and concentrated to dryness under reduced pressure on a rotary evaporator. The crude product was directly used in the next reaction without purification.

A flame dried round bottom flask was charged with alkene starting material (1.0 equiv) in CH2Cl2 (0.5 M), ethyl acrylate (5.0 equiv) and flushed with Ar. Grubbs-Hoveyeda second generation catalyst (2.5 mol %) was added in one portion and the reaction was stirred at room temperature under an atmosphere of Ar. The homogeneous solution was stirred for 6 hours. Once the reaction was complete, the reaction was concentrated to dryness under reduced pressure on a rotary evaporator. The crude product was directly used in the next reaction without purification.

To a scintillation vial was added the crude aldehyde from the previous step (1 equiv). Malonate or ketoester was added (1.1 equiv), as well as 250 wt % activated 4 Å molecular sieves (powder). A magnetic stirbar and CH2Cl2 (2.0 M) were added, followed by acetic acid (0.1 equiv) and piperidine (0.1 equiv). The mixture was stirred overnight. Silica was added and the reaction concentrated under reduced pressure. The resulting mixture was loaded onto a column of silica and purified via flash column chromatography (10-20% EtOAc/hexanes) to yield the desired product.

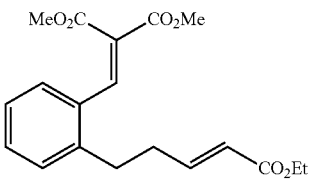 [SMILES: CCOC(=O)/C=C/CCc1ccccc1C=C(C(=O)OC)C(=O)OC]

Prepared according to the general procedure with 58% overall yield over four steps. Isolated as a ~2:1 mixture of E/Z isomers Analytical Data: 1H NMR (500 MHz, Chloroform-d) δ=7.99 (s, 1H), 7.33-7.24 (m, 2H), 7.23-7.13 (m, 2H), 6.93 (dt, J=15.7, 6.9, 1H), 5.79 (dt, J=15.7, 1.6, 1H), 4.15 (q, J=7.1, 2H), 3.85 (s, 3H), 3.70 (d, J=31.0, 5H), 3.38 (s, 1H), 2.82 (dd, J=8.8, 6.8, 2H), 2.49-2.40 (m, 2H), 1.26 (t, J=7.1, 3H). 13C NMR (126 MHz, CDCl3) δ 166.52, 166.42, 164.20, 147.16, 142.22, 140.18, 132.35, 130.26, 129.58, 128.09, 126.71, 122.31, 77.27, 77.02, 76.76, 60.24, 52.74, 52.49, 41.14, 33.23, 32.23, 14.26. LRMS (ESI): Mass calcd for C19H22O6[M+H]+: 347.1; found 347.1 HRMS (ESI): Mass calcd for C19H22O6[M+H]+: 347.1416; found 347.1418 FTIR (neat): 2997, 2710, 2244, 1663, 1637, 1613, 1562, 1374, 1283, 1254, 1206, 1181, 1146, 1104, 1021, 939, 865, 728

Preparation of Dihydrobenzofuran-Precursor Arylidene Malonate

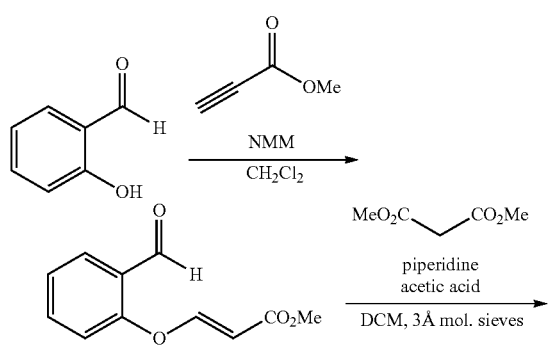

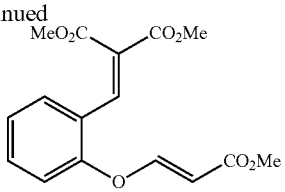

A solution of alcohol (1.0 equiv), methyl propiolate (1.1 equiv), and N-methylmorpholine (5 mol %) in CH2Cl2 (0.4 M) was stirred at room temperature for 4 h. The solution was then washed with water and saturated aqueous NaCl and dried over anhydrous sodium sulfate. The combined organic layers were concentrated to dryness under reduced pressure on a rotary evaporator. The crude product was directly used in the next reaction without purification.

To a scintillation vial was added the crude aldehyde from the previous step (1 equiv). Malonate or ketoester was added (1.1 equiv) along with 250 wt % activated 4 Å molecular sieves (powder). A magnetic stir bar and CH2Cl2 (2.0 M) were added, followed by acetic acid (0.1 equiv) and piperidine (0.1 equiv). The mixture was stirred overnight. Silica was added and the crude reaction mixture was concentrated under reduced pressure. The resulting mixture was loaded onto a column of silica and purified via flash column chromatography (10-20% EtOAc/hexanes) to yield the desired product.

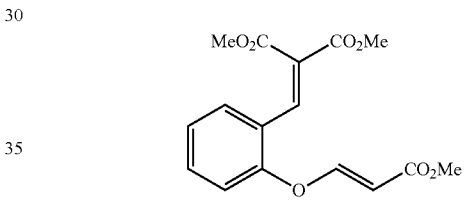

Prepared according to the general procedure with 85% overall yield over two steps. Analytical Data: 1H NMR (500 MHz, Chloroform-d) δ=8.07 (s, 1H), 7.90 (d, J=12.3, 1H), 7.62-7.50 (m, 2H), 7.37-7.29 (m, 1H), 7.23 (dd, J=8.1, 1.1, 1H), 5.71 (d, J=12.2, 1H), 4.00 (s, 3H), 3.90 (d, J=24.6, 6H). 13C NMR (126 MHz, CDCl3) δ 167.14, 166.44, 164.16, 158.28, 153.89, 152.07, 137.19, 132.14, 129.38, 127.68, 125.26, 124.52, 118.03, 103.19, 83.24, 77.33, 77.08, 76.82, 52.75, 52.60, 51.42, 50.44. LRMS (ESI): Mass calcd for C16H16O7[M+H]+: 321.1; found 321.1 HRMS (ESI): Mass calcd for C16H16O7[M+H]+: 321.0896; found 321.0899 FTIR (neat): 2994, 2495, 2353, 1669, 1633, 1605, 1531, 1484, 1281, 1226, 1208, 1168, 1122, 1094, 994, 983, 868, 743.

Selected Optimization Data

Figure 11:
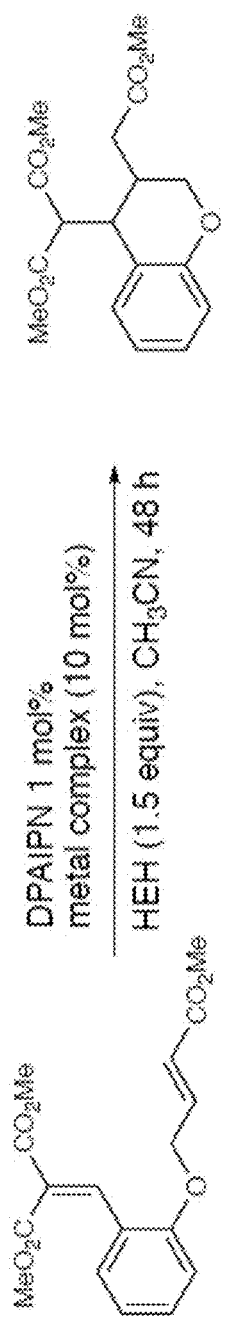
FIG. 11 provides a table illustrating a screen of chiral ligands.
Figure 11:
Figure 12:
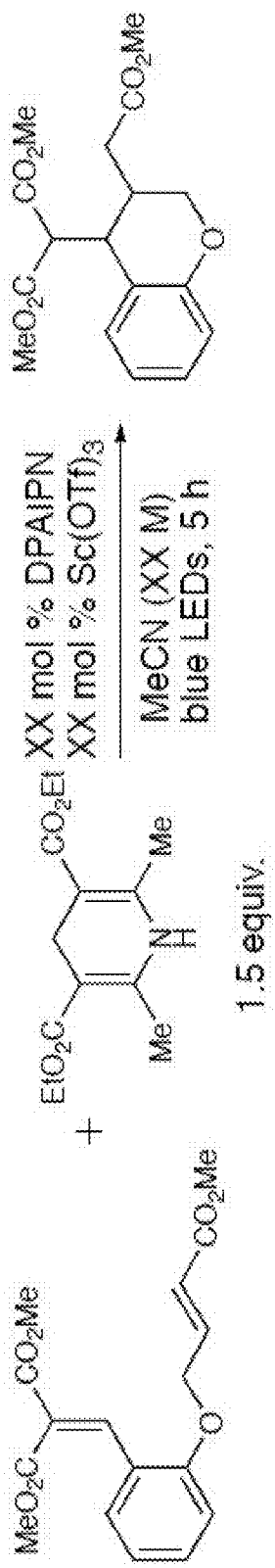
FIG. 12 provides a table illustrating the effect of concentration and catalyst loading.

Tables providing selected optimization data are illustrated in FIGS. 11, 12, and 13.

General Procedure for Reductive Cyclization

To a 2 dram vial was added arylidene malonate (1.0 equiv). The reaction vessel was equipped with a cap and stir bar and was then taken into a glovebox. DPAIPN (1 mol %) and Sc(OTf)3 (10 mol %) were added to the vial, which was then removed from the glovebox. The vial was then charged with a solution of HEH (1.5 equiv) and sparged CH3CN (0.1 M). The mixture was stirred until homogenous. The vial was then placed between 3 Kessil blue LED lights and irradiated for 5 hours (with a small fan placed for cooling). Conversion of the malonate was monitored by UPLC/MS. Upon complete conversion, the reaction was concentrated under reduced pressure onto silica gel. This silica was loaded onto a column of silica gel and isolated via flash column chromatography (2-20% ethyl acetate/hexanes) to yield the product as a mixture of diastereomers.

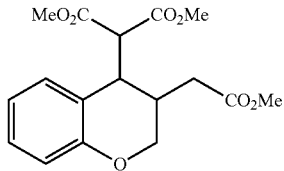 [SMILES: COC(=O)CC1COc2ccccc2C1C(C(=O)OC)C(=O)OC]

Prepared according to the general procedure in 86% yield in a 1.2:1 ratio of diastereomers 1H NMR (500 MHz, Chloroform-d) δ=7.11 (qd, J=8.1, 1.7, 1H), 7.04-6.93 (m, 1H), 6.93-6.74 (m, 2H), 4.27-4.15 (m, 1H), 3.95-3.83 (m, 1H), 3.77 (d, J=3.8, 3H), 3.74-3.53 (m, 6H), 3.46-3.35 (m, 2H), 2.69 (dddd, J=13.1, 9.0, 6.2, 3.6, 1H), 2.44 (dq, J=13.6, 7.1, 1H), 2.41-2.26 (m, 2H), 2.28-2.13 (m, 1H). 13C NMR (126 MHz, CDCl3) δ 172.29, 171.72, 168.93, 168.52, 168.22, 167.96, 153.52, 130.64, 128.98, 128.87, 128.81, 121.17, 120.50, 120.08, 118.86, 116.95, 116.50, 77.28, 77.23, 77.03, 76.77, 66.49, 64.20, 58.82, 54.07, 53.03, 52.85, 52.61, 52.49, 51.94, 51.78, 38.82, 37.50, 35.36, 32.08, 32.06, 31.54. LRMS (ESI): Mass calcd for C17H20O7[M+H]+: 337.1; found 337.1 HRMS (ESI): Mass calcd for C17H20O7[M+H]+: 337.1209; found 337.1211 FTIR (neat): 3090, 2816, 2624, 1887, 1670, 1642, 1628, 1495, 1335, 1304, 1247, 1220, 1168, 1138, 1103, 998, 987, 860, 709

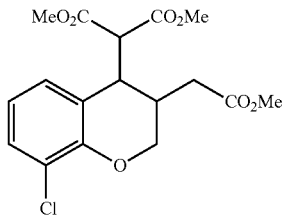 [SMILES: COC(=O)CC1COc2c(Cl)cccc2C1C(C(=O)OC)C(=O)OC]

Prepared according to the general procedure in 61% yield in a 1.2:1 ratio of diastereomers 1H NMR (500 MHz, Chloroform-d) δ=7.22 (td, J=9.1, 8.5, 1.6, 1H), 6.93 (dd, J=7.8, 1.5, 1H), 6.73 (q, J=7.6, 1H), 4.40-4.31 (m, 1H), 4.26 (dd, J=12.4, 2.1, 1H), 3.96-3.89 (m, 1H), 3.78 (s, 1H), 3.77 (s, 2H), 3.68 (s, 1H), 3.67 (s, 2H), 3.67-3.54 (m, 1H), 3.55 (s, 2H), 3.44 (d, J=16.6, 2H), 2.48-2.23 (m, 3H) 13C NMR (126 MHz, CDCl3) δ 172.00, 171.37, 168.78, 168.25, 167.99, 167.73, 149.50, 149.26, 129.69, 129.49, 129.15, 127.63, 123.05, 121.63, 121.36, 120.66, 120.56, 120.14, 77.28, 77.23, 77.02, 76.77, 67.01, 65.18, 58.59, 53.85, 53.12, 52.96, 52.64, 52.57, 52.03, 51.86, 38.81, 37.44, 35.27, 32.10, 31.99, 31.28. LRMS (ESI): Mass calcd for C17H19ClO7 [M+H]+: 371.1; found 371.1 HRMS (ESI): Mass calcd for C17H19ClO7 [M+H]+: 371.0819; found 371.0821 FTIR (neat): 3090, 2877, 2475, 1734, 1664, 1658, 1622, 1499, 1473, 1304, 1254, 1211, 1176, 1128, 1076, 1016, 985, 849, 825

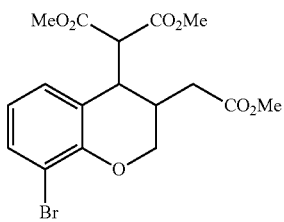 [SMILES: COC(=O)CC1COc2c(Br)cccc2C1C(C(=O)OC)C(=O)OC]

Prepared according to the general procedure in 70% yield in a 1.2:1 ratio of diastereomers 1H NMR (500 MHz, Chloroform-d) δ=7.38 (ddd, J=9.7, 7.8, 1.6, 1H), 6.97 (dd, J=7.8, 1.5, 1H), 6.67 (q, J=7.7, 1H), 4.39-4.30 (m, 1H), 4.26 (dd, J=12.0, 2.2, 1H), 4.20-4.05 (m, 1H), 3.92 (dd, J=8.0, 4.1, 1H), 3.77 (s, 2H), 3.67 (s, 1H), 3.66 (s, 2H), 3.64-3.51 (m, 1H), 3.55 (s, 2H), 3.48-3.32 (m, 2H), 2.77-2.66 (m, 1H), 2.48-2.32 (m, 2H), 2.31-2.14 (m, 1H) 13C NMR (126 MHz, CDCl3) δ 171.99, 171.35, 168.78, 168.23, 167.98, 167.72, 150.11, 132.79, 132.59, 129.93, 128.43, 123.04, 121.18, 120.73, 120.67, 110.87, 110.55, 77.29, 77.24, 77.03, 76.78, 67.10, 65.35, 58.60, 53.83, 53.11, 52.96, 52.62, 52.56, 52.03, 51.86, 38.95, 37.54, 35.28, 32.12, 32.07, 31.34, 14.21. LRMS (ESI): Mass calcd for C17H19BrO7 [M+H]+: 415.1; found 415.2 HRMS (ESI): Mass calcd for C17H19BrO7 [M+H]+: 415.0314; found 415.0316 FTIR (neat): 3090, 2964, 2557, 2069, 1708, 1647, 1606, 1550, 1354, 1292, 1229, 1189, 1168, 1122, 1048, 1016, 978, 900, 778.

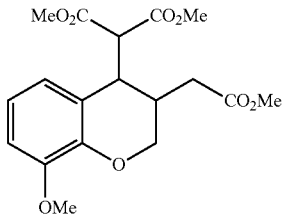 [SMILES: COC(=O)CC1COc2c(OC)cccc2C1C(C(=O)OC)C(=O)OC]

Prepared according to the general procedure in 62% yield in a 1.2:1 ratio of diastereomers 1H NMR (500 MHz, Chloroform-d) δ=6.87-6.73 (m, 1H), 6.77-6.65 (m, 1H), 6.61 (dd, J=6.5, 2.9, 1H), 4.37-4.19 (m, 1H), 4.21-4.06 (m, 1H), 3.96-3.80 (m, 3H), 3.76 (s, 2H), 3.84-3.67 (m, 2H), 3.65 (s, 2H), 3.70-3.59 (m, 1H), 3.56 (s, 2H), 3.62-3.46 (m, 1H), 3.48-3.32 (m, 2H), 2.80-2.55 (m, 1H), 2.47 (dt, J=15.9, 7.9, 1H), 2.40-2.27 (m, 1H) 13C NMR (126 MHz, CDCl3) δ 172.23, 168.20, 167.92, 148.14, 142.94, 122.27, 120.71, 119.97, 119.62, 119.52, 117.61, 110.41, 110.35, 77.28, 77.23, 77.02, 76.77, 66.85, 64.63, 58.89, 58.85, 55.98, 55.87, 55.81, 54.16, 53.04, 52.95, 52.86, 52.64, 52.50, 51.92, 51.75, 50.89, 39.14, 38.64, 37.37, 35.23, 31.95, 31.87, 31.30. LRMS (ESI): Mass calcd for C18H22O8 [M+H]+: 367.1; found 367.1 HRMS (ESI): Mass calcd for C18H22O8 [M+H]+: 367.1315; found 367.1317 FTIR (neat): 3028, 2893, 2704, 2196, 1693, 1631, 1600, 1531, 1428, 1273, 1269, 1218, 1165, 1128, 1091, 995, 938, 896, 696.

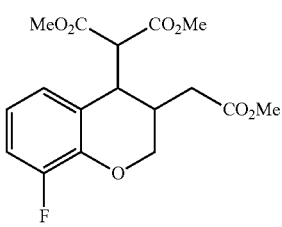 [SMILES: COC(=O)CC1COc2c(F)cccc2C1C(C(=O)OC)C(=O)OC]

Prepared according to the general procedure in 74% yield in a 1.5:1 ratio of diastereomers 1H NMR (500 MHz, Chloroform-d) δ=7.00-6.88 (m, 1H), 6.84-6.66 (m, 2H), 4.35-4.27 (m, 1H), 4.25-4.10 (m, 1H), 3.78 (s, 1H), 3.77 (s, 2H), 3.67 (s, 2H), 3.72-3.60 (m, 2H), 3.59 (t, J=7.4, 1H), 3.56 (s, 2H), 3.51-3.42 (m, 2H), 2.50-2.27 (m, 3H) 13C NMR (126 MHz, CDCl3) δ 172.03, 171.45, 168.74, 168.31, 168.01, 167.74, 152.30, 150.35, 142.05, 141.96, 125.57, 125.54, 123.96, 123.93, 123.77, 121.40, 119.85, 119.80, 119.44, 119.38, 115.38, 115.23, 115.11, 77.27, 77.02, 76.77, 66.71, 64.64, 58.59, 53.90, 53.11, 52.95, 52.68, 52.56, 52.01, 51.85, 38.34, 38.32, 37.11, 35.25, 31.96, 31.91, 31.31. LRMS (ESI): Mass calcd for C17H19FO7 [M+H]+: 355.1; found 355.1 HRMS (ESI): Mass calcd for C17H19FO7 [M+H]+: 355.1115; found 355.1110 FTIR (neat): 3093, 2766, 2601, 1918, 1667, 1639, 1599, 1489, 1346, 1278, 1238, 1215, 1183, 1151, 1082, 1016, 983, 854, 747.

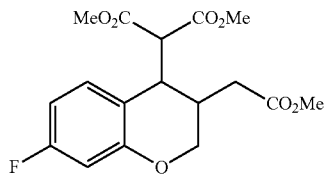 [SMILES: COC(=O)CC1COc2cc(F)ccc2C1C(C(=O)OC)C(=O)OC]

Prepared according to the general procedure in 68% yield in a 1.5:1 ratio of diastereomers 1H NMR (500 MHz, Chloroform-d) δ=6.93 (ddd, J=41.9, 8.3, 6.5, 1H), 6.57-6.46 (m, 2H), 4.25-4.15 (m, 2H), 4.12-4.02 (m, 1H), 3.87 (dd, J=7.9, 4.2, 1H), 3.77 (d, J=3.4, 1H), 3.77 (s, 2H), 3.77-3.64 (m, 4H), 3.62-3.51 (m, 3H), 3.44 (d, J=1.0, 1H), 3.39 (d, J=10.3, 1H), 2.74-2.63 (m, 1H), 2.45-2.24 (m, 2H) 13C NMR (126 MHz, CDCl3) δ 172.12, 171.50, 168.87, 168.39, 168.12, 167.83, 163.81, 161.86, 154.65, 154.55, 131.79, 131.71, 130.10, 114.69, 114.67, 108.01, 107.83, 107.32, 107.15, 104.09, 103.90, 103.51, 77.27, 77.02, 76.77, 66.34, 64.37, 58.69, 53.90, 53.06, 52.91, 52.63, 52.56, 52.00, 51.84, 38.29, 36.91, 35.26, 32.16, 32.13, 31.36. LRMS (ESI): Mass calcd for C17H19FO7 [M+H]+: 355.1; found 355.1 HRMS (ESI): Mass calcd for C17H19FO7 [M+H]+: 355.1115; found 355.1114 FTIR (neat): 3052, 2886, 2485, 2252, 1708, 1656, 1626, 1544, 1331, 1286, 1255, 1208, 1186, 1121, 1109, 994, 952, 839, 719.

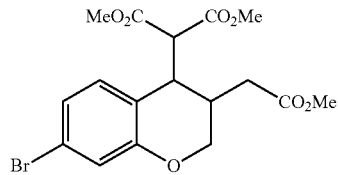 [SMILES: COC(=O)CC1COc2cc(Br)ccc2C1C(C(=O)OC)C(=O)OC]

Prepared according to the general procedure in 84% yield in a 1.2:1 ratio of diastereomers 1H NMR (500 MHz, Chloroform-d) δ=7.02-6.94 (m, 1H), 6.97-6.84 (m, 2H), 4.16 (d, J=2.1, 1H), 4.07 (td, J=11.8, 11.1, 8.2, 1H), 3.77 (s, 2H), 3.76 (d, J=7.1, 1H), 3.72-3.52 (m, 7H), 3.46 (s, 1H), 3.37 (d, J=10.1, 1H), 2.45-2.23 (m, 3H) 13C NMR (126 MHz, CDCl3) δ 172.05, 171.48, 168.31, 168.02, 167.73, 154.32, 141.64, 132.43, 131.90, 130.23, 123.68, 123.14, 122.03, 121.55, 120.10, 119.65, 117.99, 114.80, 77.28, 77.22, 77.02, 76.77, 66.60, 66.52, 64.44, 58.49, 53.72, 52.95, 52.63, 51.85, 38.38, 37.06, 35.28, 32.04, 31.95, 31.26, 29.94. LRMS (ESI): Mass calcd for C17H19BrO7 [M+H]+: 415.1; found 415.2 HRMS (ESI): Mass calcd for C17H19BrO7 [M+H]+: 415.0314; found 415.0318 FTIR (neat): 3100, 2967, 2561, 2235, 1686, 1650, 1625, 1567, 1371, 1303, 1258, 1217, 1185, 1124, 1120, 1013, 933, 900, 802.

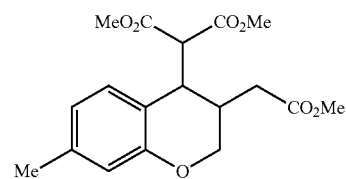 [SMILES: COC(=O)CC1COc2cc(C)ccc2C1C(C(=O)OC)C(=O)OC]

Prepared according to the general procedure in 88% yield in a 1.2:1 ratio of diastereomers 1H NMR (500 MHz, Chloroform-d) δ=6.91-6.70 (m, 1H), 6.67-6.56 (m, 2H), 4.23-4.03 (m, 2H), 3.91-3.80 (m, 1H), 3.76 (d, J=2.9, 2H), 3.74-3.52 (m, 5H), 3.48 (s, 1H), 3.36 (d, J=10.3, 1H), 2.48-2.34 (m, 1H), 2.37-2.22 (m, 2H), 2.25-2.13 (m, 3H) 13C NMR (126 MHz, CDCl3) δ 172.35, 171.83, 168.27, 168.00, 153.28, 139.05, 138.83, 130.37, 128.46, 121.57, 121.43, 121.08, 118.11, 117.28, 116.86, 115.79, 77.29, 77.23, 77.03, 76.78, 66.57, 64.12, 58.88, 54.13, 52.99, 52.82, 52.64, 52.50, 51.91, 51.75, 38.60, 37.32, 35.32, 32.15, 31.94, 31.59, 21.05. LRMS (ESI): Mass calcd for C18H22O7 [M+H]+: 351.1; found 351.1 HRMS (ESI): Mass calcd for C18H22O7 [M+H]+: 351.1366; found 351.1365 FTIR (neat): 3093, 2893, 2538, 1936, 1699, 1631, 1625, 1522, 1451, 1290, 1247, 1200, 1182, 1121, 1059, 997, 945, 895, 756.

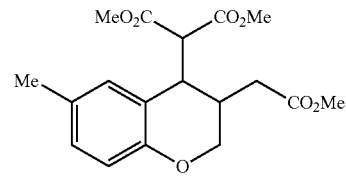 [SMILES: COC(=O)CC1COc2ccc(C)cc2C1C(C(=O)OC)C(=O)OC]

Prepared according to the general procedure in 91% yield in a 1.2:1 ratio of diastereomers 1H NMR (500 MHz, Chloroform-d) δ=6.91 (td, J=8.2, 2.1, 1H), 6.80-6.71 (m, 1H), 6.74-6.60 (m, 1H), 4.23-4.01 (m, 2H), 3.91-3.79 (m, 1H), 3.81-3.69 (m, 3H), 3.72-3.63 (m, 3H), 3.66-3.55 (m, 1H), 3.51 (d, J=56.4, 3H), 3.35 (d, J=10.2, 1H), 2.44 (dd, J=18.0, 10.2, 1H), 2.38-2.26 (m, 2H), 2.28-2.14 (m, 1H), 2.19 (s, 2H). 13C NMR (126 MHz, CDCl3) δ 172.35, 171.75, 168.97, 168.55, 168.29, 167.99, 151.49, 151.26, 130.77, 129.67, 129.62, 129.42, 129.16, 129.12, 120.82, 118.50, 116.65, 116.20, 77.28, 77.23, 77.03, 76.77, 66.39, 64.13, 58.86, 54.13, 53.00, 52.82, 52.52, 52.37, 51.92, 51.76, 38.86, 37.53, 35.38, 32.20, 32.08, 31.63, 20.50, 20.48. LRMS (ESI): Mass calcd for C18H22O7 [M+H]+: 351.1; found 351.1 HRMS (ESI): Mass calcd for C18H22O7 [M+H]+: 351.1366; found 351.1367 FTIR (neat): 3042, 2854, 2608, 2018, 1689, 1636, 1628, 1580, 1467, 1299, 1238, 1219, 1179, 1120, 1086, 1012, 951, 856, 759.

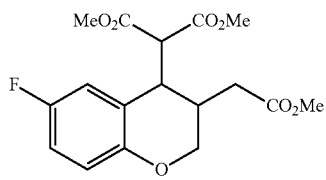 [SMILES: COC(=O)CC1COc2ccc(F)cc2C1C(C(=O)OC)C(=O)OC]

Prepared according to the general procedure in 92% yield in a 1.3:1 ratio of diastereomers 1H NMR (500 MHz, Chloroform-d) δ=6.93-6.76 (m, 1H), 6.80-6.70 (m, 1H), 6.68 (ddd, J=30.4, 8.4, 3.1, 1H), 4.23-4.02 (m, 2H), 3.77 (s, 2H), 3.91-3.73 (m, 1H), 3.75-3.65 (m, 2H), 3.67 (s, 2H), 3.61 (s, 2H), 3.52 (s, 1H), 3.38 (d, J=10.0, 1H), 2.48-2.25 (m, 3H) 13C NMR (126 MHz, CDCl3) δ 172.12, 171.61, 168.68, 168.01, 167.73, 157.56, 155.66, 149.58, 119.92, 118.00, 117.93, 117.36, 116.47, 116.08, 115.89, 115.49, 115.01, 114.83, 77.28, 77.02, 76.77, 66.59, 64.37, 58.64, 53.82, 53.11, 52.94, 52.65, 51.84, 38.76, 37.50, 35.33, 31.88, 31.33. LRMS (ESI): Mass calcd for C17H19FO7 [M+H]+: 355.1; found 355.1 HRMS (ESI): Mass calcd for C17H19FO7 [M+H]+: 355.1115; found 355.1117 FTIR (neat): 3081, 2939, 2530, 2298, 1666, 1635, 1620, 1564, 1423, 1303, 1223, 1194, 1188, 1158, 1089, 1007, 928, 901, 775.

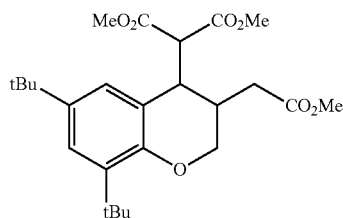 [SMILES: COC(=O)CC1COc2c(cc(C(C)(C)C)cc2C(C)(C)C)C1C(C(=O)OC)C(=O)OC]

Prepared according to the general procedure in 910% yield in a 1.1:1 ratio of diastereomers 1H NMR (500 MHz, Chloroform-d) δ=7.14 (d, J=2.5, 1H), 6.85 (d, J=2.4, 1H), 4.22-4.14 (m, 1H), 4.09 (dt, J=11.5, 1.9, 1H), 3.95-3.83 (m, 1H), 3.86-3.73 (m, 1H), 3.76 (s, 2H), 3.76-3.65 (m, 2H), 3.66 (s, 2H), 3.55 (s, 2H), 3.46 (s, 1H), 3.44-3.33 (m, 1H), 2.45-2.28 (m, 2H), 1.33 (d, J=24.0, 1H), 1.32 (s, 8H), 1.30-1.18 (m, 2H), 1.22 (s, 7H). 13C NMR (126 MHz, CDCl3) δ 172.52, 168.30, 168.27, 150.17, 141.90, 136.79, 125.14, 123.17, 118.83, 77.28, 77.23, 77.03, 76.77, 66.26, 64.22, 59.09, 52.77, 52.48, 51.72, 39.85, 35.83, 34.95, 34.93, 34.22, 31.73, 31.62, 31.58, 31.55, 29.68. LRMS (ESI): Mass calcd for C25H36O7 [M+H]+: 449.2; found 449.2 HRMS (ESI): Mass calcd for C25H36O7 [M+H]+: 449.2461; found 449.2462 FTIR (neat): 3039, 2804, 2587, 1770, 1690, 1630, 1615, 1569, 1413, 1305, 1243, 1216, 1168, 1134, 1084, 1002, 956, 852, 759.

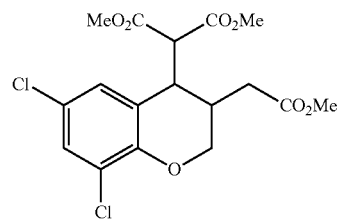 [SMILES: COC(=O)CC1COc2c(Cl)cc(Cl)cc2C1C(C(=O)OC)C(=O)OC]

Prepared according to the general procedure in 90% yield in a 1.2:1 ratio of diastereomers 1H NMR (500 MHz, Chloroform-d) δ=7.26-7.19 (m, 1H), 6.97-6.93 (m, 1H), 4.34 (dt, J=12.1, 1.7, 1H), 4.26-4.04 (m, 2H), 3.77 (s, 3H), 3.67 (s, 3H), 3.61 (s, 3H), 3.68-3.46 (m, 2H), 3.47-3.38 (m, 1H), 2.45-2.13 (m, 3H). 13C NMR (126 MHz, CDCl3) δ 171.79, 167.76, 167.45, 148.14, 129.38, 129.15, 128.78, 127.49, 124.93, 122.51, 121.76, 77.27, 77.22, 77.02, 76.77, 67.02, 65.36, 58.40, 53.65, 53.21, 53.05, 52.77, 52.71, 52.10, 51.93, 38.68, 37.30, 35.21, 32.04, 31.84, 31.07. LRMS (ESI): Mass calcd for C17H18Cl2O7 [M+H]+: 405.1; found 405.1 HRMS (ESI): Mass calcd for C17H18Cl2O7 [M+H]+: 405.0430; found 405.0428 FTIR (neat): 3097, 2839, 2540, 2264, 1682, 1658, 1622, 1496, 1398, 1304, 1254, 1218, 1165, 1128, 1033, 1001, 941, 887, 799.

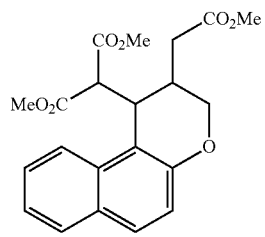 [SMILES: COC(=O)CC1COc2ccc3ccccc3c2C1C(C(=O)OC)C(=O)OC]

Prepared according to the general procedure in 82% yield in a 1.5:1 ratio of diastereomers 1H NMR (500 MHz, Chloroform-d) δ=7.83 (d, J=8.5, 1H), 7.78-7.57 (m, 2H), 7.44 (dddd, J=8.4, 6.6, 5.2, 1.3, 1H), 7.33-7.24 (m, 1H), 7.00 (dd, J=8.9, 3.0, 1H), 4.38-4.28 (m, 1H), 4.29-4.06 (m, 2H), 3.81 (s, 1H), 3.81-3.55 (m, 6H), 3.03 (s, 2H), 2.78 (s, 1H), 2.58-2.38 (m, 2H), 2.33 (dd, J=16.5, 5.8, 1H) 13C NMR (126 MHz, CDCl3) δ 172.37, 171.23, 169.71, 168.72, 168.29, 168.09, 151.46, 132.99, 132.28, 129.42, 129.23, 128.83, 128.55, 128.05, 126.44, 126.31, 123.31, 123.26, 122.89, 121.91, 118.65, 118.42, 110.56, 77.30, 77.25, 77.05, 76.79, 64.76, 64.15, 57.80, 53.99, 53.04, 52.78, 52.14, 52.06, 51.86, 51.78, 35.86, 34.60, 33.08, 32.90, 32.73, 32.01, 14.22. LRMS (ESI): Mass calcd for C21H22O7 [M+H]+: 387.1; found 387.1 HRMS (ESI): Mass calcd for C21H22O7 [M+H]+: 387.1366; found 387.1364 FTIR (neat): 3006, 2943, 2689, 2235, 1669, 1657, 1608, 1515, 1340, 1305, 1264, 1199, 1166, 1140, 1046, 1000, 987, 832, 747.

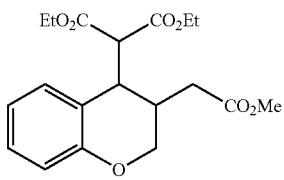 [SMILES: CCOC(=O)C(C(=O)OCC)C1c2ccccc2OCC1CC(=O)OC]

Prepared according to the general procedure in 86% yield in a 1.2:1 ratio of diastereomers 1H NMR (500 MHz, Chloroform-d) δ=7.20-6.89 (m, 2H), 6.90-6.73 (m, 2H), 4.35-4.07 (m, 5H), 4.09-3.96 (m, 1H), 3.98-3.88 (m, 1H), 3.77-3.62 (m, 3H), 3.62-3.50 (m, 1H), 3.45-3.33 (m, 1H), 2.52-2.26 (m, 2H), 1.35-1.12 (m, 4H), 1.04 (dt, J=30.5, 7.1, 2H). 13C NMR (126 MHz, CDCl3) δ 172.33, 171.77, 167.89, 167.64, 153.55, 130.85, 129.10, 128.85, 128.70, 120.42, 120.02, 119.11, 116.83, 116.40, 77.28, 77.23, 77.02, 76.77, 66.50, 64.24, 62.05, 61.85, 61.73, 61.58, 59.08, 54.32, 51.90, 51.76, 38.68, 37.29, 35.40, 32.09, 32.07, 31.63, 14.06, 13.82, 13.65. LRMS (ESI): Mass calcd for C19H24O7 [M+H]+: 365.1; found 365.2 HRMS (ESI): Mass calcd for C19H24O7 [M+H]+: 365.1522; found 365.1525 FTIR (neat): 3033, 2854, 2391, 1822, 1663, 1650, 1626, 1544, 1486, 1300, 1252, 1210, 1184, 1151, 1039, 1008, 935, 904, 742.

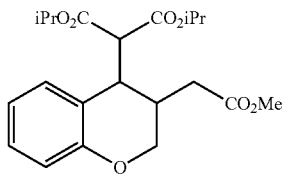

Prepared according to the general procedure in 82% yield in a 1.2:1 ratio of diastereomers 1H NMR (500 MHz, Chloroform-d) δ=7.15-6.99 (m, 2H), 6.76 (q, J=8.4, 7.6, 2H), 5.14-5.06 (m, 1H), 5.09-4.94 (m, 1H), 4.89 (hept, J=6.3, 1H), 4.78 (dq, J=12.5, 6.4, 1H), 4.25-4.09 (m, 2H), 3.79-3.66 (m, 1H), 3.66 (s, 1H), 3.66 (s, 2H), 3.55-3.45 (m, 1H), 3.40 (d, J=9.7, 1H), 2.48-2.38 (m, 1H), 2.42-2.17 (m, 2H), 1.28-1.19 (m, 5H), 1.22-1.10 (m, 3H), 1.08 (d, J=6.3, 1H), 0.98 (s, 1H), 0.99-0.88 (m, 2H), 0.87 (s, 1H). 13C NMR (126 MHz, CDCl3) δ 172.37, 171.86, 167.75, 167.44, 167.24, 153.85, 153.56, 131.06, 129.23, 128.74, 128.58, 120.40, 120.01, 119.34, 116.75, 116.40, 77.28, 77.02, 76.77, 69.71, 69.64, 69.44, 69.42, 69.27, 66.65, 64.29, 59.41, 54.64, 51.86, 51.73, 38.43, 37.04, 35.45, 32.04, 31.99, 31.69, 21.73, 21.54, 21.51, 21.40, 21.17. LRMS (ESI): Mass calcd for C21H28O7 [M+H]+: 393.2; found 393.2 HRMS (ESI): Mass calcd for C21H28O7 [M+H]+: 393.1835; found 393.1837 FTIR (neat): 3072, 2984, 2652, 1843, 1671, 1653, 1601, 1501, 1474, 1283, 1270, 1199, 1180, 1161, 1049, 1007, 971, 884, 740.

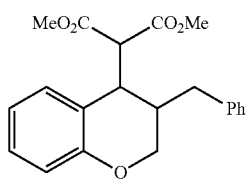 [SMILES: COC(=O)C(C(=O)OC)C1c2ccccc2OCC1Cc1ccccc1]

Prepared according to the general procedure in 85% yield in a 1.1:1 ratio of diastereomers 1H NMR (500 MHz, Chloroform-d) δ=7.32-7.19 (m, 5H), 7.15 (ddd, J=8.5, 7.3, 1.7, 1H), 7.06 (dd, J=7.7, 1.6, 1H), 6.96-6.86 (m, 2H), 4.60 (d, J=10.3, 1H), 4.21 (d, J=9.2, 1H), 4.09 (dd, J=11.8, 1.5, 1H), 3.79 (dd, J=11.7, 2.4, 1H), 3.47 (dddd, J=10.5, 9.1, 2.4, 1.5, 1H), 3.40 (s, 3H), 3.22 (s, 3H). 13C NMR (126 MHz, CDCl3) δ 169.59, 168.65, 156.02, 137.23, 131.52, 128.39, 128.27, 127.90, 127.40, 121.22, 120.63, 118.00, 77.27, 77.22, 77.02, 76.76, 65.01, 64.28, 52.10, 51.91, 42.45, 36.13, 34.40, 14.13. LRMS (ESI): Mass calcd for C21H22O5 [M+H]+: 355.1; found 355.1 HRMS (ESI): Mass calcd for C21H22O5 [M+H]+: 355.1311; found 355.1310 FTIR (neat): 3067, 2980, 2871, 1654, 1651, 1605, 1555, 1504, 1421, 1281, 1270, 1190, 1180, 1161, 1079, 1021, 925, 880, 742.

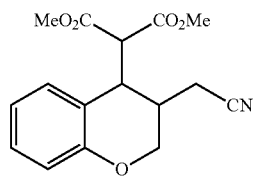 [SMILES: COC(=O)C(C(=O)OC)C1c2ccccc2OCC1CC#N]

Prepared according to the general procedure in 81% yield in a 1.2:1 ratio of diastereomers 1H NMR (500 MHz, Chloroform-d) δ=7.51-7.34 (m, 1H), 7.31-7.20 (m, 1H), 7.18-7.02 (m, 2H), 4.53-4.46 (m, 1H), 4.42 (dd, J=12.2, 2.3, 1H), 4.00 (s, 3H), 3.97-3.85 (m, 2H), 3.85 (s, 3H), 3.70 (dd, J=9.8, 1.7, 1H), 2.66 (d, J=7.9, 2H), 2.61-2.51 (m, 1H). 13C NMR (126 MHz, CDCl3) δ 167.92, 167.76, 153.07, 144.50, 130.52, 129.42, 121.13, 117.82, 117.58, 117.28, 115.18, 77.30, 77.05, 76.79, 63.18, 58.40, 53.00, 52.69, 52.61, 38.10, 32.46, 29.79, 19.60, 12.81. LRMS (ESI): Mass calcd for C16H17NO5 [M+H]+: 304.1; found 304.1 HRMS (ESI): Mass calcd for C16H17NO5 [M+H]+: 304.1107; found 304.1105 FTIR (neat): 3037, 2910, 2591, 1791, 1694, 1653, 1623, 1585, 1365, 1283, 1227, 1197, 1176, 1162, 1063, 999, 924, 885, 773.

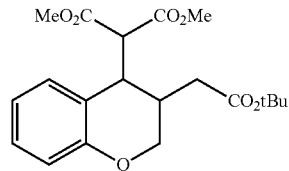 [SMILES: COC(=O)C(C(=O)OC)C1c2ccccc2OCC1CC(=O)OC(C)(C)C]

Prepared according to the general procedure in 77% yield in a 1.5:1 ratio of diastereomers 1H NMR (500 MHz, Chloroform-d) δ=7.11 (qd, J=7.9, 1.7, 1H), 6.99 (dd, J=8.0, 1.8, 1H), 6.95-6.86 (m, 1H), 6.81-6.74 (m, 2H), 4.25-4.12 (m, 2H), 4.07 (dd, J=11.1, 9.4, 1H), 3.93-3.87 (m, 1H), 3.77 (d, J=6.2, 3H), 3.64-3.55 (m, 1H), 3.55 (s, 2H), 3.42 (s, 1H), 2.71-2.61 (m, 1H), 2.39-2.15 (m, 2H), 2.07 (dd, J=15.9, 9.2, 1H), 1.43 (d, J=3.6, 9H). 13C NMR (126 MHz, CDCl3) δ 171.10, 170.46, 168.99, 168.58, 168.26, 167.98, 153.81, 153.55, 130.61, 129.03, 128.90, 128.75, 121.35, 120.37, 119.96, 119.14, 116.89, 116.45, 81.16, 80.86, 77.27, 77.02, 76.76, 66.39, 64.35, 58.80, 53.99, 52.98, 52.82, 52.53, 52.46, 38.90, 37.52, 36.76, 33.73, 32.29, 31.56, 28.10, 28.06. LRMS (ESI): Mass calcd for C20H26O7 [M+H]+: 379.1; found 379.2, HRMS (ESI): Mass calcd for C20H26O7 [M+H]+: 379.1679; found 379.1681 FTIR (neat): 3057, 2972, 2548, 1877, 1676, 1643, 1616, 1541, 1374, 1297, 1252, 1211, 1177, 1126, 1068, 1009, 955, 867, 782.

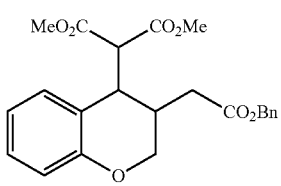 [SMILES: COC(=O)C(C(=O)OC)C1c2ccccc2OCC1CC(=O)OCc1ccccc1]

Prepared according to the general procedure in 88% yield in a 1.2:1 ratio of diastereomers 1H NMR (500 MHz, Chloroform-d) δ=7.39-7.25 (m, 5H), 7.11 (qd, J=7.1, 6.2, 1.6, 1H), 6.98 (dd, J=8.2, 1.7, 1H), 6.78 (dt, J=8.1, 5.6, 2H), 5.16-5.05 (m, 2H), 4.26-4.15 (m, 2H), 4.09 (dd, J=11.2, 8.9, 1H), 3.93 (dd, J=8.2, 4.1, 1H), 3.75 (s, 2H), 3.71 (s, 1H), 3.66-3.55 (m, 1H), 3.56 (s, 2H), 3.43 (d, J=11.2, 2H), 2.71 (tq, J=8.9, 4.2, 1H), 2.49 (dd, J=18.0, 10.1, 1H), 2.44-2.31 (m, 2H). 13C NMR (126 MHz, CDCl3) δ 171.68, 171.13, 168.20, 167.95, 153.51, 135.71, 130.64, 128.99, 128.83, 128.80, 128.62, 128.56, 128.40, 128.37, 128.28, 128.25, 121.18, 120.50, 120.08, 118.85, 116.95, 116.50, 77.27, 77.22, 77.02, 76.76, 66.76, 66.54, 66.50, 64.21, 58.80, 54.05, 53.00, 52.84, 52.61, 52.49, 38.85, 37.51, 35.58, 32.28, 32.06, 31.52. LRMS (ESI): Mass calcd for C23H24O7 [M+H]+: 413.2; found 413.2 HRMS (ESI): Mass calcd for C23H24O7 [M+H]+: 413.1522; found 413.1525 FTIR (neat): 3004, 2936, 2750, 1987, 1683, 1629, 1627, 1524, 1394, 1279, 1254, 1194, 1186, 1153, 1110, 998, 945, 849, 698.

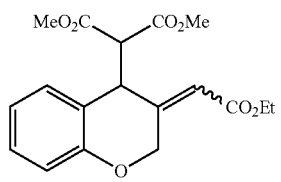 [SMILES: CCOC(=O)C=C1COc2ccccc2C1C(C(=O)OC)C(=O)OC]

Prepared according to the general procedure in 81% yield in a 1:1 ratio of Z/E isomers 1H NMR (500 MHz, Chloroform-d) δ=7.30 (dd, J=7.7, 1.7, 1H), 7.28 (s, 2H), 7.21-7.10 (m, 1H), 6.99-6.82 (m, 1H), 5.89 (p, J=0.9, 1H), 5.62 (d, J=8.4, 1H), 5.01 (dd, J=14.3, 1.9, 1H), 4.53 (dt, J=14.4, 1.2, 1H), 4.26-4.12 (m, 2H), 3.86 (d, J=8.5, 1H), 3.71 (s, 2H), 3.68 (s, 1H), 3.59 (s, 2H), 1.55 (s, 1H), 1.31 (t, J=7.1, 3H), 1.26 (t, J=9.8, 1H). 13C NMR (126 MHz, CDCl3) δ 167.77, 167.59, 165.12, 154.26, 151.22, 130.12, 129.06, 122.63, 121.66, 117.52, 117.02, 77.27, 77.22, 77.02, 76.76, 69.30, 60.52, 57.24, 52.68, 52.47, 52.39, 37.80, 28.64, 14.20. LRMS (ESI): Mass calcd for C18H20O7 [M+H]+: 349.1; found 349.1 HRMS (ESI): Mass calcd for C18H20O7 [M+H]+: 349.1209; found 349.1210 FTIR (neat): 3095, 2750, 2389, 1840, 1691, 1658, 1619, 1525, 1471, 1276, 1264, 1204, 1163, 1129, 1099, 1019, 946, 862, 727.

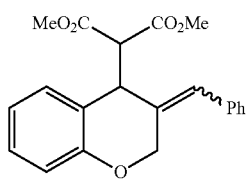 [SMILES: COC(=O)C(C(=O)OC)C1C(=Cc2ccccc2)COc2ccccc21]

Prepared according to the general procedure in 86% yield in a 1:1 ratio of Z/E isomers 1H NMR (500 MHz, Chloroform-d) δ=7.45-7.16 (m, 5H), 7.13 (s, 1H), 7.19-7.03 (m, 1H), 7.03 (d, J=8.2, 1H), 7.00-6.77 (m, 2H), 5.12-4.94 (m, 1H), 4.93 (s, 1H), 4.59 (dd, J=12.9, 1.5, 1H), 4.25 (d, J=10.8, 1H), 3.97-3.85 (m, 1H), 3.80-3.71 (m, 1H), 3.68 (s, 1H), 3.65 (s, 2H), 3.61 (d, J=13.1, 1H), 3.51 (s, 1H), 3.24 (d, J=7.7, 1H). 13C NMR (126 MHz, CDCl3) δ 169.61, 167.45, 155.83, 154.06, 135.54, 133.18, 132.08, 132.01, 131.78, 131.07, 129.45, 129.26, 129.03, 128.97, 128.71, 128.65, 128.63, 128.56, 128.53, 128.40, 128.28, 128.16, 127.55, 127.45, 126.63, 126.53, 122.30, 121.32, 121.22, 120.64, 117.19, 117.05, 112.45, 112.03, 87.15, 84.00, 77.27, 77.02, 76.76, 70.38, 65.22, 57.49, 57.41, 56.70, 52.67, 52.54, 52.41, 51.42, 45.58, 37.90, 30.29. LRMS (ESI): Mass calcd for C21H20O5 [M+H]+: 353.1; found 353.1 HRMS (ESI): Mass calcd for C21H20O5 [M+H]+: 353.1311; found 353.1312 FTIR (neat): 3080, 2843, 2561, 1773, 1672, 1655, 1618, 1552, 1486, 1295, 1268, 1215, 1187, 1134, 1062, 1017, 987, 855, 766.

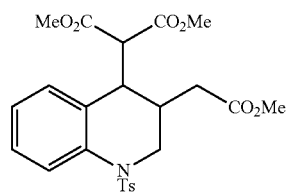 [SMILES: COC(=O)CC1CN(S(=O)(=O)c2ccc(C)cc2)c2ccccc2C1C(C(=O)OC)C(=O)OC]

Prepared according to the general procedure in 85% yield in a 1.3:1 ratio of diastereomers 1H NMR (500 MHz, Chloroform-d) δ=7.84 (ddd, J=13.3, 8.4, 1.1, 1H), 7.71-7.59 (m, 2H), 7.37-7.19 (m, 3H), 7.07 (dd, J=7.7, 1.8, 1H), 7.06-6.92 (m, 1H), 3.89-3.79 (m, 1H), 3.77 (d, J=2.6, 4H), 3.77-3.67 (m, 1H), 3.69 (s, 1H), 3.67 (s, 2H), 3.64-3.43 (m, 1H), 3.44 (s, 2H), 3.35 (s, 1H), 2.78 (d, J=11.0, 1H), 2.62 (dp, J=10.0, 3.8, 3.2, 1H), 2.42 (d, J=2.1, 3H), 2.18 (d, J=7.1, 1H). 13C NMR (126 MHz, CDCl3) δ 171.79, 167.70, 167.60, 144.08, 136.21, 135.49, 130.71, 129.80, 129.76, 128.53, 128.20, 128.12, 127.18, 127.11, 126.43, 124.08, 122.91, 122.34, 77.29, 77.03, 76.78, 56.24, 52.98, 52.85, 52.35, 52.24, 52.04, 51.96, 51.82, 47.99, 47.00, 41.79, 37.39, 34.52, 34.16, 32.78, 21.57. LRMS (ESI): Mass calcd for C24H27NO8S [M+H]+: 490.2; found 490.2 HRMS (ESI): Mass calcd for C24H27NO8S [M+H]+: 490.1457; found 490.1455 FTIR (neat): 3029, 2819, 2633, 2317, 1706, 1632, 1604, 1546, 1331, 1304, 1247, 1192, 1168, 1141, 1072, 1008, 957, 886, 713.

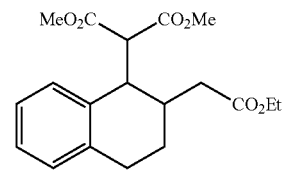 [SMILES: CCOC(=O)CC1CCc2ccccc2C1C(C(=O)OC)C(=O)OC]

Prepared according to the general procedure in 82% yield in a 1.2:1 ratio of diastereomers 1H NMR (500 MHz, Chloroform-d) δ=7.31-7.19 (m, 4H), 7.12 (dt, J=15.7, 6.8, 1H), 4.34-4.19 (m, 2H), 3.80 (s, 6H), 3.85-3.72 (m, 1H), 3.35 (d, J=7.7, 2H), 2.95-2.85 (m, 2H), 2.60 (dtd, J=8.1, 6.7, 1.6, 2H), 1.43-1.31 (m, 3H). 13C NMR (126 MHz, CDCl3) δ 169.23, 166.52, 147.76, 138.99, 135.40, 129.92, 129.59, 129.50, 129.38, 129.30, 127.21, 127.16, 126.55, 122.00, 77.28, 77.23, 77.03, 76.78, 60.38, 60.25, 52.71, 52.63, 52.57, 38.06, 35.69, 33.37, 31.25, 30.89, 30.73, 29.71, 28.46, 14.28. LRMS (ESI): Mass calcd for C19H24O6 [M+H]+: 349.1; found 349.1 HRMS (ESI): Mass calcd for C19H24O6 [M+H]+: 349.1573; found 349.1573 FTIR (neat): 3090, 2759, 2533, 2099, 1660, 1630, 1623, 1531, 1475, 1302, 1259, 1209, 1178, 1133, 1075, 1000, 968, 904, 804.

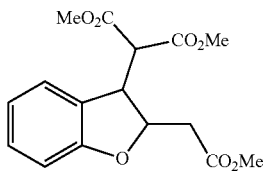 [SMILES: COC(=O)CC1Oc2ccccc2C1C(C(=O)OC)C(=O)OC]

Prepared according to the general procedure in 72% yield in a 1.1:1 ratio of diastereomers 1H NMR (500 MHz, Chloroform-d) δ=7.24-7.00 (m, 2H), 6.86-6.76 (m, 2H), 5.07-5.00 (m, 1H), 3.86-3.79 (m, 1H), 3.82-3.72 (m, 1H), 3.75-3.64 (m, 8H), 3.67-3.56 (m, 1H), 2.85-2.67 (m, 2H) 13C NMR (126 MHz, CDCl3) δ 170.68, 168.08, 168.02, 158.81, 129.62, 125.35, 125.08, 120.83, 110.43, 82.41, 77.27, 77.02, 76.76, 56.01, 52.86, 52.65, 51.91, 46.42, 40.28. LRMS (ESI): Mass calcd for C16H18O7 [M+H]+: 323.1; found 323.1 HRMS (ESI): Mass calcd for C16H18O7 [M+H]+: 323.1053; found 323.1051 FTIR (neat): 3016, 2953, 2588, 1766, 1667, 1633, 1628, 1580, 1446, 1306, 1250, 1212, 1178, 1138, 1107, 991, 990, 906, 798.

Procedure for Krapcho Decarboxylation and Dieckmann Condensation

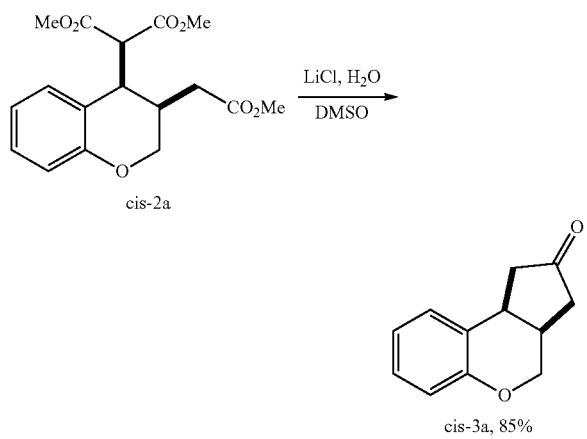

To a 0.5-2 mL Biotage microwave vial outfitted with a magnetic stir bar was added 2a (1 equiv) and LiCl (4.1 equiv). Water (3 equiv) was then added, followed by DMSO (0.5 M). The vial was then sealed and heated in an oil bath at 140° C. for 18 hours. Upon observation of complete conversion, the vial was removed from oil bath and allowed to cool to room temperature. The solution was diluted with water (15 mL) and extracted with EtOAc (3×10 mL). The organic extracts were then pooled and washed with water (4×15 mL) and saturated brine solution (4×15 mL). The organic extracts were then concentrated under reduced pressure onto silica gel and loaded onto a column of silica gel. 3a was then isolated via flash chromatography (5-40% ethyl acetate/hexanes) as a thick, clear oil (85%).

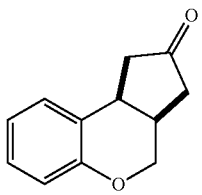

1H NMR (500 MHz, Chloroform-d) δ=7.17-7.07 (m, 2H), 7.00-6.89 (m, 1H), 6.86 (d, J=8.2, 1H), 4.21-4.11 (m, 1H), 3.95 (dd, J=11.2, 7.5, 1H), 3.61 (dt, J=8.7, 6.7, 1H), 2.86-2.75 (m, 2H), 2.56-2.42 (m, 2H), 2.25 (ddd, J=19.1, 6.4, 1.5, 1H). 13C NMR (126 MHz, CDCl3) δ 217.18, 153.87, 129.97, 127.93, 121.45, 117.30, 77.28, 77.03, 76.77, 65.58, 45.81, 39.53, 34.68, 34.62, 33.89, 22.66. LRM(ESI): Mass calcd for C12H21O2 [M+H]+: 189.1; found 189.1 HRMS (ESI): Mass calcd for C12H21O2 [M+H]+: 189.0837; found 189.0835 FTIR (neat): 3095, 1720, 1472, 1325, 1241, 1170, 1111, 1032, 968, 904, 804.

Procedure for Determination of Quantum Yield

The photon flux of the fluorimeter was determined using a ferrioxolate Hatchard-Parker actinometer as described by Yoon et al.3 Based on the average of three experiments, the photon flux at 420 nm (10 nm slit width) was determined to be 5.27712E-09 einsteins s−1. UV/Vis absorbance spectra of DPAIPN in MeCN (0.1 M) indicated that essentially all light was absorbed at 420 nm (f=0.99148). A screw-top quartz cuvette with Teflon septa was charged with 1a (0.2 mmol, 1 equiv), DPAIPN (1 mol %), scandium triflate (10 mol %), HEH (1.5 equiv), and a small Teflon coated magnetic stirbar in a glovebox. The cuvette was sealed and removed from glovebox. The cuvette was then capped with a PTFE stopper, and 2 mL sparged MeCN added. The solution was stirred until homogenous. The sample was placed in the fluorimeter and irradiated (k=420 nm, slit width=10.0 nm) for 5400 s (3 hours). 1 H NMR based on a trimethoxybenzene standard determined the yield of product formed was 30%. The average quantum yield of the two experiments was determined to be 1.0.

Procedure for Light/Dark Experiment

To verify the necessity of light to maintain the conversion of 1a to 2a, a "light/dark" experiment was performed. A J-Young NMR tube was charged with 1a (0.2 mmol, 1 equiv), DPAIPN (1 mol %), scandium triflate (10 mol %), and HEH (1.5 equiv) in a glovebox. Upon removal from the glovebox, the reaction mixture was irradiated with 456 nm Kessil blue LEDs for periods of 1 hour, followed by 2 hours of no irradiation (3 cycles of 3 hours, 9 hours total). Notably, the reaction progressed steadily during periods of irradiation, while no conversion was observed during periods without irradiation. This is indicative that propagation is likely not a operational mechanistic process over the course of the reaction.

Procedure for UV-Vis Experiments

A 1 dram vial equipped with a rubber septum and a stir bar was charged with 1a (0.1 mmol, 1 equiv), scandium triflate (0 or 100 mol %), and tertiary amine (0 or 150 mol %) in a glovebox. Upon removal from the glovebox, the reaction mixture was stirred for 2 hours, followed by measurement of the UV-Vis spectra using a Thermo Fisher Nanodrop One Spectrophotometer.

A single crystal of trans-2a was grown by evaporative diffusion in dichloromethane with hexanes as the antisolvent at room temperature. This crystal structure was deposited in the Cambridge Crystallographic Data Centre and assigned as CCDC 1835356.

REFERENCES

1. Jung, M. E. Tetrahedron 1976, 32, 3
2. (a) Curran, D. P.; van Elburg, P. A. Tetrahedron Lett. 1989, 30, 2501; (b) Curran, D. P.; Seong, C. M. Tetrahedron 1992, 48, 2175; (c) Stork, G.; Mook, R.; Biller, S. A.; Rychnovsky, S. D. J. Am. Chem. Soc. 1983, 105, 3741; (d) Stork, G.; Suh, H. S.; Kim, G. J. Am. Chem. Soc. 1991, 113, 7054
3. (a) Studer, A.; Curran, D. P. Nature Chemistry 2014, 6, 765; (b) Studer, A.; Curran, D. P. Angew. Chem. Int. Ed. 2016, 55, 58
4. (a) Prier, C. K.; Rankic, D. A.; MacMillan, D. W. C. Chem. Rev. 2013, 113, 5322; (b) Shaw, M. H.; Twilton, J.; MacMillan, D. W. C. J. Org. Chem. 2016, 81, 6898
5. (a) Petronijevid, F. R.; Nappi, M.; MacMillan, D. W. C. J. Am. Chem. Soc. 2013, 135, 18323; (b) Terrett, J. A.; Clift, M. D.; MacMillan, D. W. C. J. Am. Chem. Soc. 2014, 136, 6858; (c) Jeffrey, J. L.; Petronijevid, F. R.; MacMillan, D. W. C. J. Am. Chem. Soc. 2015, 137, 8404; (d) Fava, E.; Millet, A.; Nakajima, M.; Loescher, S.; Rueping, M. Angew. Chem. Int. Ed. 2016, 55, 6776; (e) Fuentes de Arriba, A. L.; Urbitsch, F.; Dixon, D. J. Chem. Commun. 2016, 52, 14434; (f) Wang, R.; Ma, M.; Gong, X.; Panetti, G. B.; Fan, X.; Walsh, P. J. Org. Lett. 2018, 20, 2433; (g) Xu, W.; Ma, J.; Yuan, X.-A.; Dai, J.; Xie, J.; Zhu, C. Angew. Chem. Int. Ed. 2018, 57, 10357
6. (a) Qi, L.; Chen, Y. Angew. Chem. Int. Ed. 2016, 55, 13312; (b) Lee, K. N.; Lei, Z.; Ngai, M.-Y. J. Am. Chem. Soc. 2017, 139, 5003; (c) Zhang, H.-H.; Yu, S. J. Org. Chem. 2017, 82, 9995; (d) Chen, M.; Zhao, X.; Yang, C.; Xia, W. Org. Lett. 2017, 19, 3807; (e) Leitch, J. A.; Fuentes de Arriba, Angel L.; Tan, J.; Hoff, O.; Martinez, C. M.; Dixon, D. J. Chem. Sci. 2018, 9, 6653
7. Ishitani, O.; Yanagida, S.; Takamuku, S.; Pac, C. J. Org. Chem. 1987, 52, 2790
8. (a) Tarantino, K. T.; Liu, P.; Knowles, R. R. J. Am. Chem. Soc. 2013, 135, 10022; (b) Hopkinson, M. N.; Sahoo, B.; Li, J. L.; Glorius, F. Chemistry—A European Journal 2014, 20, 3874; (c) Yayla, H. G.; Knowles, R. R. Synlett 2014, 25, 2819; (d) Nakajima, M.; Fava, E.; Loescher, S.; Jiang, Z.; Rueping, M. Angew. Chem. Int. Ed. 2015, 54, 8828; (e) Fava, E.; Nakajima, M.; Nguyen, A. L. P.; Rueping, M. J. Org. Chem. 2016, 81, 6959; (f) Gentry, E. C.; Knowles, R. R. Acc. Chem. Res. 2016, 49, 1546; (g) Miller, D. C.; Tarantino, K. T.; Knowles, R. R. Top. Curr. Chem. 2016, 374, 30; (h) Skubi, K. L.; Blum, T. R.; Yoon, T. P. Chem. Rev. 2016, 116, 10035; (i) Yoon, T. P. Acc. Chem. Res. 2016, 49, 2307
9. (a) Neumann, M.; Zeitler, K. Chemistry—A European Journal 2013, 19, 6950; (b) Pandey, G.; Hajra, S.; Ghorai, M. K.; Kumar, K. R. J. Am. Chem. Soc. 1997, 119, 8777; (c) Crimmins, M. T. Chem. Rev. 1988, 88, 1453; (d) Schuster, D. I.; Lem, G.; Kaprinidis, N. A. Chem. Rev. 1993, 93, 3; (e) Streuff, J.; Gansauer, A. Angew. Chem. Int. Ed. 2015, 54, 14232; (f) Larraufie, M.-H.; Pellet, R.; Fensterbank, L.; Goddard, J.-P.; Lacôte, E.; Malacria, M.; Ollivier, C. Angew. Chem. Int. Ed. 2011, 50, 4463
10. (a) Ischay, M. A.; Anzovino, M. E.; Du, J.; Yoon, T. P. J. Am. Chem. Soc. 2008, 130, 12886; (b) Ischay, M. A.; Lu, Z.; Yoon, T. P. J. Am. Chem. Soc. 2010, 132, 8572; (c) Du, J.; Espelt, L. R.; Guzei, I. A.; Yoon, T. P. Chem. Sci. 2011, 2, 2115; (d) Hurtley, A. E.; Cismesia, M. A.; Ischay, M. A.; Yoon, T. P. Tetrahedron 2011, 67, 4442; (e) Lu, Z.; Shen, M.; Yoon, T. P. J. Am. Chem. Soc. 2011, 133, 1162; (f) Yoon, T. P. ACS Catalysis 2013, 3, 895; (g) Du, J.; Yoon, T. P. J. Am. Chem. Soc. 2009, 131, 14604; (h) Tyson, E. L.; Famey, E. P.; Yoon, T. P. Org. Lett. 2012, 14, 1110
11. (a) Murphy, J. J.; Bastida, D.; Paria, S.; Fagnoni, M.; Melchiorre, P. Nature 2016, 532, 218; (b) Dell'Amico, L.; Fernández-Alvarez, V. M.; Maseras, F.; Melchiorre, P. Angew. Chem. Int. Ed. 2017, 56, 3304; (c) Silvi, M.; Verrier, C.; Rey, Y. P.; Buzzetti, L.; Melchiorre, P. Nature Chemistry 2017, 9, 868; (d) Mazzarella, D.; Crisenza, G. E. M.; Melchiorre, P. J. Am. Chem. Soc. 2018, 140, 8439; (e) Verrier, C.; Alandini, N.; Pezzetta, C.; Molitemo, M.; Buzzetti, L.; Hepburn, H. B.; Vega-Peñaloza, A.; Silvi, M.; Melchiorre, P. ACS Catalysis 2018, 8, 1062; (f) de Assis, F. F.; Huang, X.; Akiyama, M.; Pilli, R. A.; Meggers, E. J. Org. Chem. 2018; (g) Lin, S.-X.; Sun, G.-J.; Kang, Q. Chem. Commun. 2017, 53, 7665; (h) Bonilla, P.; Rey, Y. P.; Holden, C. M.; Melchiorre, P. Angew. Chem. Int. Ed. 2018, 57, 12819; (i) Goti, G.; Bieszczad, B.; Vega-Peñaloza, A.; Melchiorre, P. Angew. Chem. Int. Ed. 0,
12. McDonald, B. R.; Scheidt, K. A. Org. Lett. 2018, 20, 6877
13. (a) Shono, T.; Nishiguchi, I.; Ohmizu, H. J. Am. Chem. Soc. 1977, 99, 7396; (b) Zhao, G.; Yang, C.; Guo, L.; Sun, H.; Lin, R.; Xia, W. J. Org. Chem. 2012, 77, 6302
14. Gang, D.; Jun, Y.; Xiao-ping, Y.; Hui-jun, X. Tetrahedron 1990, 46, 5967
15. (a) Farmer, R. L.; Scheidt, K. A. Chem. Sci. 2013, 4, 3304; (b) Farmer, R. L.; Biddle, M. M.; Nibbs, A. E.; Huang, X.; Bergan, R. C.; Scheidt, K. A. ACS Medicinal Chemistry Letters 2010, 1, 400; (c) Biddle, M. M.; Lin, M.; Scheidt, K. A. J. Am. Chem. Soc. 2007, 129, 3830; (d) Nibbs, A. E.; Baize, A.-L.; Herter, R. M.; Scheidt, K. A. Org. Lett. 2009, 11, 4010; (e) McDonald, B. R.; Nibbs, A. E.; Scheidt, K. A. Org. Lett. 2015, 17, 98; (f) Xu, L.; Gordon, R.; Farmer, R.; Pattanayak, A.; Binkowski, A.; Huang, X.; Avram, M.; Krishna, S.; Voll, E.; Pavese, J.; Chavez, J.; Bruce, J.; Mazar, A.; Nibbs, A.; Anderson, W.; Li, L.; Jovanovic, B.; Pruell, S.; Valsecchi, M.; Francia, G.; Betori, R.; Scheidt, K.; Bergan, R. Nature Communications 2018, 9, 2454; (g) Nibbs, A. E.; Scheidt, K. A. Eur. J. Org. Chem. 2012, 2012, 449
16. (a) Luo, J.; Zhang, J. ACS Catalysis 2016, 6, 873; (b) Romero, N. A.; Nicewicz, D. A. Chem. Rev. 2016, 116, 10075
17. Humbel, S.; Côte, I.; Hoffmann, N.; Bouquant, J. J. Am. Chem. Soc. 1999, 121, 5507
18. Akalay, D.; Dumer, G.; Bats, J. W.; Bolte, M.; Gobel, M. W. J. Org. Chem. 2007, 72, 5618
19. Foy, N. J.; Forbes, K. C.; Crooke, A. M.; Gruber, M. D.; Cannon, J. S. Org. Lett. 2018,
20. Cismesia, M. A.; Yoon, T. P. Chem. Sci. 2015, 6, 5426
21. (a) Miyake, Y.; Nakajima, K.; Nishibayashi, Y. J. Am. Chem. Soc. 2012, 134, 3338; (b) Wallentin, C.-J.; Nguyen, J. D.; Finkbeiner, P.; Stephenson, C. R. J. J. Am. Chem. Soc. 2012, 134, 8875; (c) Sahoo, B.; Hopkinson, M. N.; Glorius, F. J. Am. Chem. Soc. 2013, 135, 5505; (d) Mizuta, S.; Engle, K. M.; Verhoog, S.; Galicia-López, O.; O'Duill, M.; Médebielle, M.; Wheelhouse, K.; Rassias, G.; Thompson, A. L.; Gouverneur, V. Org. Lett. 2013, 15, 1250; (e) Oh, S. H.; Malpani, Y. R.; Ha, N.; Jung, Y.-S.; Han, S. B. Org. Lett. 2014, 16, 1310
22. (a) Burnett, G. M.; Melville, H. W. Chem. Rev. 1954, 54, 225; (b) McIntosh, R. G.; Eager, R. L.; Spinks, J. W. T.

Science 1960, 131, 992; (c) McIntosh, R. G.; Eager, R. L.; Spinks, J. W. T. Can. J. Chem. 1965, 43, 3490
23. (a) Pitre, S. P.; McTiernan, C. D.; Scaiano, J. C. Acc. Chem. Res. 2016, 49, 1320; (b) Arias-Rotondo, D. M.; McCusker, J. K. Chem. Soc. Rev. 2016, 45, 5803
24. Vrabel et al., Acta Chimica Slvaca, Vol. 11, No. 1, 2018, pp. 1-5, DIO: 10.2478/acs-2018-0001
25. Akhtar T, Hameed S, Al-Masoudi N A, Loddo R, La Colla P (2008) Acta Pharm. 58: 135-149.
26. Allen F H, Johnson O, Shields G P, Smith B R, Towler M (2004) J. Appl. Cryst. 37: 335-338.
27. Bernstein J, Davis R E, Shimoni L, Chang N L (1995) Angew. Chem. Int. Ed. Engl. 34: 1555-1573.
28. Brandenburg K (2001) DIAMOND. Crystal Impact GbR, Bonn, Germany. Cremer D, Pople J A (1975) J. Am. Chem. Soc. 97: 1354-1362.
29. Ellis G P, Lockhart I M, Meedemycz D, Schweizer E E (1977) Chromenes, Chromanones and Chromones, edited by GP, Ellis. New York: John Wiley and Sons, Inc.
30. Ellis G P, Lockhart I M (2007). The Chemistry of Heterocyclic Compounds, hromenes, Chromanones and Chromones 31: edited by G. P. Ellis 1-119. New York: Wiley-VCH.
31. Farrugia L J (1999) J. Appl. Cryst. 30: 565. Horton D A, Boume G T, Smythe M L (2003) Chem. Rev. 103: 893-930.
32. Hussain M I, Amir M (1986) J. Indian Chem. Soc. 63: 317-320.
33. Chenera P, West M L, Finkelstein J A, Dreyer G B J (1993) J. Org. Chem. 58: 5605-5606.
34. Choi S J, Park H J, Lee S K, Kim S W, Han G, Choo H Y P (2006) Bioorg. Med. Chem. 14: 1229-1235.
35. Jin L, Song B, Zhang G, Xu R, Zhang S, Gao X, Hu D, Yang S (2006) Bioorg. Med. Chem. Lett. 16: 1537-1543.
36. Koojiman H, Spek A L, Kleijin H, Van Maanen H L, Jastrzelski J T, Van Kozrkowski A P (1984) Acc. Chem. Res. 17: 410-416.
37. Kwak J H, Kim B H, Jung J K, Kim Y, Cho J, Lee H (2007). Arch. Pharm. Res. 30: 1210-1215.
38. Lampronti I, Martello D, Bianchi N, Borgatti M, Lambertini E, Piva R, Jabbar S, Shahabuddin Kabir Choudhuri M, Tareq Hassan Khan M, Gambari R (2003) Phytomedicine 10: 300-308.
39. Lang F, Zewge D, Song Z J, Biba M, Dormer P, Tschaen D, Volanteb R P, Reiderb P J (2003) Tetrahedron Lett. 44: 5285-5288.
40. Ma T, Liu L, Xue H, Li L, Han C, Wang L, Chen Z, Liu G (2008) J. Med. Chem. 51: 1432-1446.
41. Mortimer C G, Wells G, Crochard J P, Stone E L, Bradshaw T D, Stevens M F G, Westwell A D (2006) J. Med. Chem. 49: 179-185.
42. Nicolaou K C, Pfefferkorn J A, Roecker A J, Cao G Q, Barluenga S, Mitchell H J (2000) J. Am. Chem. Soc. 122: 9939-9953.
43. O'Brien S E, Browne H L, Bradshaw T D, Westwell A D, Stevens M F G, Laughton C A (2003) Org. Biomol. Chem. 1: 493-497.
44. Oxford Diffraction (2009). CrysAlisPro. Oxford Diffraction Ltd, Abingdon, Oxfordshire, England.
46. Pecchio M, Solis P N, López-Pérez J L, Vasquez Y, Rodriguez N, Olmedo D, Correa M, San Feliciano A, Gupta M P (2006) J. Nat. Prod. 69: 410-413. Prado S, Janin Y L, Saint-Joanis B, Brodin P, Michel S, Koch M, Cole S T, Tillequin F, Bost P E (2007) Bioorg. Med. Chem. 15: 2177-2186.
47. Sheldrick G M (2008) Acta Cryst. A64: 112-122.
48. Spek A L (2009) Acta Cryst. D65: 148-155.
49. Svetlik J, Prónayová N, Svorc L', Frecer V (2014) Tetrahedron 70: 8354-8360.
50. Tanaka N, Takaish, Y, Shikishima Y, Nakanishi Y, Bastow K, Lee K H, Honda G, Ito M, Takeda Y, Kodzhimatov O K, Ashurmetov O (2004) J. Nat. Prod. 67: 1870-1875.
51. Zou Y S, Hou A J, Zhu G F (2005) Chem. Biodivers. 2: 131-138.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method of synthesizing a compound of formula,

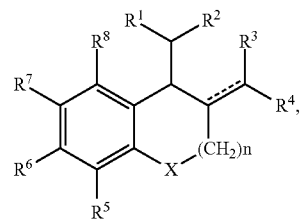

or a salt or hydrate thereof,
the method comprising irradiating reagents comprising:
(a) a compound having a formula selected from

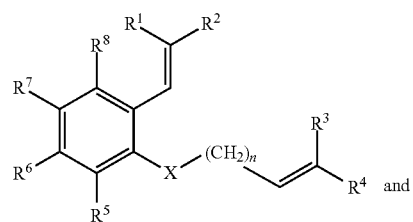

and

-continued

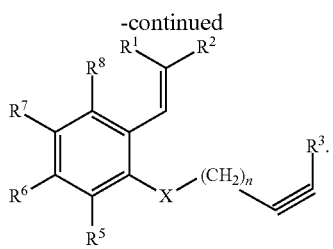

wherein:
$R^1$ and $R^2$ are independently selected from hydrogen, alkyl, alkoxy, carboxy, and carboxyalkyl;

$R^3$ and $R^4$ are independently selected from hydrogen, alkyl, alkoxy, carboxy, carboxyalkyl, aryl, carboxyalkylaryl (e.g., carboxybenzyl ester), and cyano;

Optionally, wherein at least one of $R^1$, $R^2$, $R^3$, and $R^4$, is not hydrogen;

$R^5$, $R^6$, $R^7$, and $R^8$ are independently selected from hydrogen, alkyl, alkoxy, halo and optionally $R^7$ and $R^8$ form an aryl group;

X is selected from oxygen, nitrogen (NH), and carbon ($CH_2$); and n is an integer selected from 0-1;

(b) a photocatalyst selected from the group consisting of

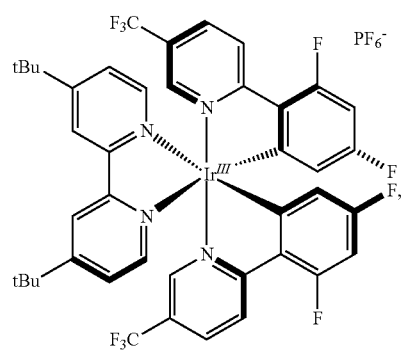

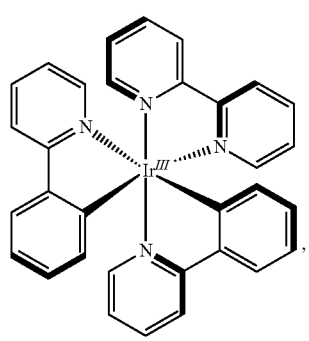

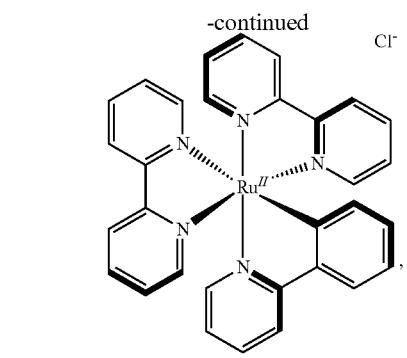

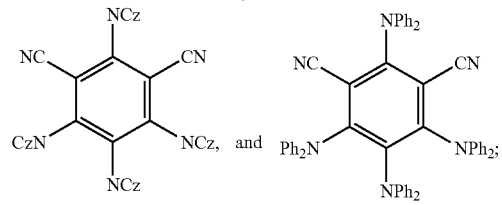

(c) a Lewis acid selected from the group consisting of $Sc(OTf)_3$, $M(OTf)_2$, $La(OTf)_3$, and LiCl; and (d) a reducing agent, wherein the reducing agent is a Hantzsch ester of formula

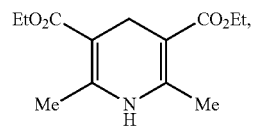

or

N,N-diisopropylethylamine (DIPEA), triethylamine ($NEt_3$), tributylamine 2 ($NBu_3$), or 2-phenyl-dihydrobenzothaizoline (BT).

2. The method of claim 1, wherein the reagents are irradiated with blue light.

3. The method of claim 1, wherein $R^1$ and/or $R^2$ is carboxyalkyl.

4. The method of claim 3, wherein the carboxyalkyl is a branched or unbranched carboxy-$C_{1-6}$-alkyl.

5. The method of claim 3, wherein the carboxyalkyl is carboxymethyl.

6. The method of claim 3, wherein the carboxyalkyl is carboxyethyl.

7. The method of claim 3, wherein the carboxyalkyl is carboxyisopropyl.

8. The method of claim 1, wherein at least one of $R^5$, $R^6$, and $R^7$ is bromo.

9. The method of claim 1, wherein at least one of $R^5$, $R^6$, and $R^7$ is fluoro.

10. The method of claim 1, wherein at least one of $R^5$, $R^6$, and $R^7$ is chloro.

11. The method of claim 1, wherein at least one of $R^5$, $R^6$, and $R^7$ is a branched or unbranched $C_{1-6}$-alkyl.

12. The method of claim 1, wherein at least one of $R^5$, $R^6$, and $R^7$ is methyl.

13. The method of claim 1, wherein at least one of $R^5$, $R^6$, and $R^7$ is tert-butyl.

14. The method of claim 1, wherein $R^7$ and $R^8$ join together to form an aryl group.

15. The method of claim 1, wherein $R^3$ or $R^4$ is hydrogen.
16. The method of claim 1, wherein $R^3$ is hydrogen and $R^4$ is selected from the group consisting of phenyl, branched or unbranched carboxy-$C_{1-6}$-alkyl, cyano, and carboxyalkylaryl.
17. The method of claim 1, wherein the synthesized compound has a formula selected from:
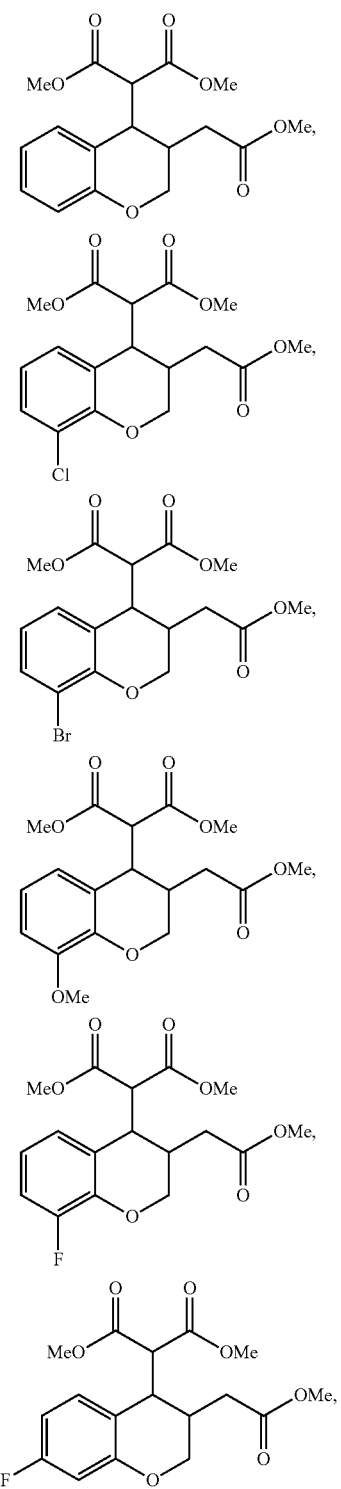
-continued
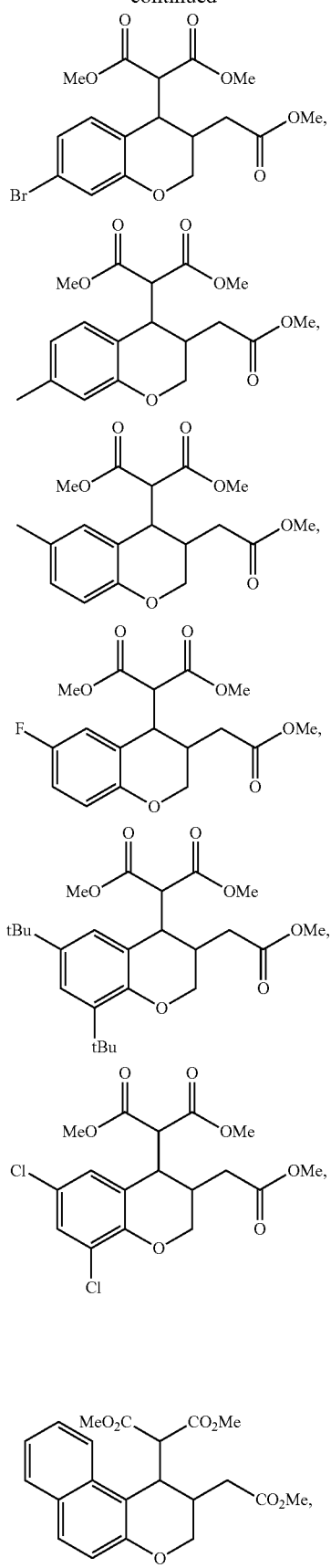

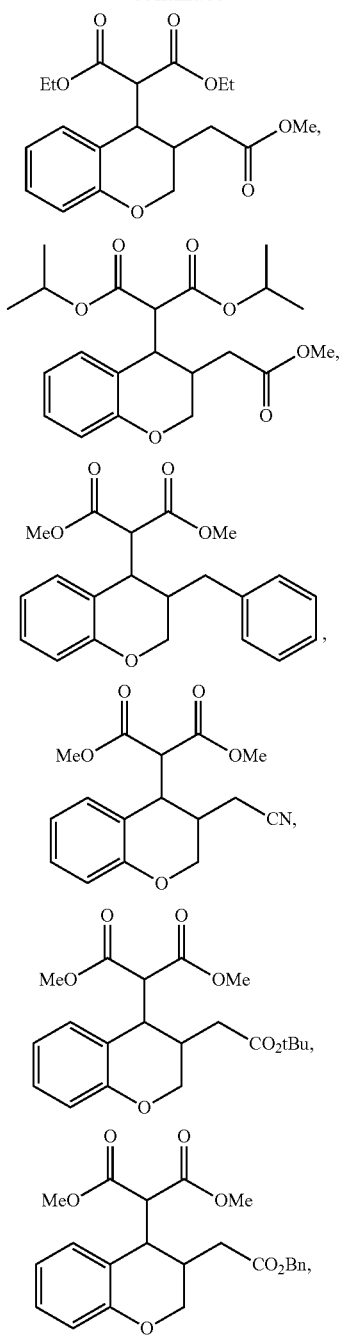
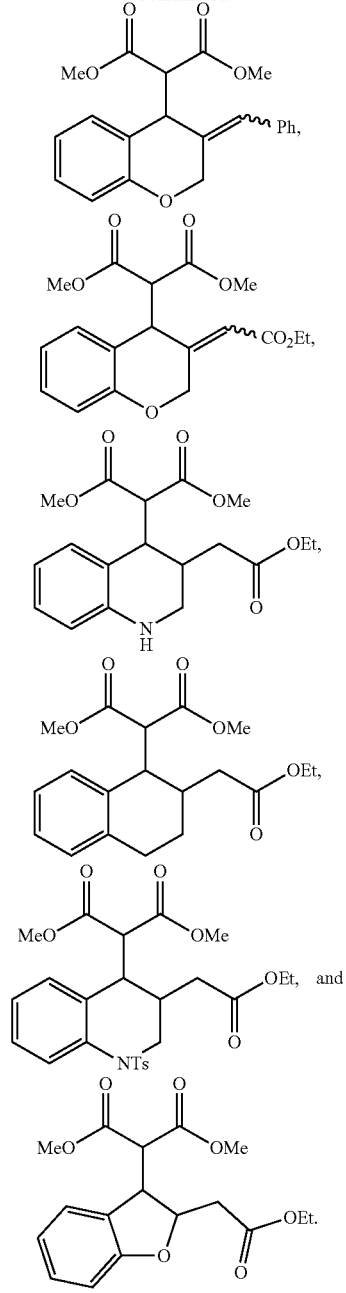
* * * * *